US010329252B2

(12) United States Patent
Aoki et al.

(10) Patent No.: US 10,329,252 B2
(45) Date of Patent: Jun. 25, 2019

(54) STABILIZER COMPOUND, LIQUID CRYSTAL COMPOSITION, AND DISPLAY ELEMENT

(71) Applicant: DIC CORPORATION, Tokyo (JP)

(72) Inventors: Yoshio Aoki, Kita-adachi-gun (JP); Ayaki Hosono, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/751,380

(22) PCT Filed: Aug. 23, 2016

(86) PCT No.: PCT/JP2016/074474
§ 371 (c)(1),
(2) Date: Feb. 8, 2018

(87) PCT Pub. No.: WO2017/038552
PCT Pub. Date: Mar. 9, 2017

(65) Prior Publication Data
US 2018/0230094 A1  Aug. 16, 2018

(30) Foreign Application Priority Data

Sep. 4, 2015  (JP) .............................. 2015-174809

(51) Int. Cl.
| | | |
|---|---|---|
| C07D 207/08 | (2006.01) | |
| C07D 207/16 | (2006.01) | |
| C07D 207/46 | (2006.01) | |
| C09K 19/54 | (2006.01) | |
| C09K 19/34 | (2006.01) | |

(52) U.S. Cl.
CPC ......... *C07D 207/08* (2013.01); *C07D 207/16* (2013.01); *C07D 207/46* (2013.01); *C09K 19/3483* (2013.01); *C09K 19/54* (2013.01)

(58) Field of Classification Search
USPC .................. 548/572; 546/279.1; 544/335
See application file for complete search history.

(56) References Cited

U.S. PATENT DOCUMENTS

| | | | |
|---|---|---|---|
| 3,020,288 A | 2/1962 | Wragg et al. | |
| 3,838,059 A | 9/1974 | Wong | |
| 4,111,901 A | 9/1978 | Hechenbleikner | |
| 4,731,376 A | 3/1988 | Hideg et al. | |
| 5,032,600 A | 7/1991 | Hideg et al. | |
| 5,264,204 A | 11/1993 | Cacheris et al. | |
| 5,567,411 A | 10/1996 | Keana et al. | |
| 5,714,510 A * | 2/1998 | Proctor .................. | A61K 8/46 514/423 |
| 6,441,088 B1 | 8/2002 | Kaul et al. | |
| 9,604,932 B2 * | 3/2017 | Salzman .............. | C07D 223/04 |
| 2003/0215390 A1 | 11/2003 | Rosen | |
| 2006/0011886 A1 | 1/2006 | Li et al. | |
| 2013/0037745 A1 | 2/2013 | Hung et al. | |
| 2013/0248763 A1 | 9/2013 | Goebel et al. | |
| 2013/0258268 A1 | 10/2013 | Goebel et al. | |
| 2015/0192852 A1 | 7/2015 | Sato et al. | |
| 2015/0273087 A1 | 10/2015 | Rosen | |
| 2015/0376203 A1 | 12/2015 | Zhao et al. | |
| 2016/0208172 A1 * | 7/2016 | Gotoh ................... | C09K 19/32 |
| 2018/0230383 A1 * | 8/2018 | Yamamoto ............. | C09K 19/54 |

FOREIGN PATENT DOCUMENTS

| | | | | |
|---|---|---|---|---|
| EP | 2894476 A1 * | 7/2015 | ............... | C12N 9/93 |
| JP | 48-97780 B2 | 12/1973 | | |
| JP | 57-10663 A | 1/1982 | | |
| JP | 60-67587 A | 4/1985 | | |
| JP | 60-500668 A | 5/1985 | | |

(Continued)

OTHER PUBLICATIONS

Nakatsuji et al. Journal of Physical Organic Chemistry 19:333-340 (2006) (Year: 2006).*
Caproiu et al., "Synthesis and characterisation of several di-, tri-, and tetra-radicals linked by flexible or rigid linkers", ARKIVOC, 2008, No. 14, pp. 158-165, cited in ISR and Japanese Notification of Reasons for Refusal (8 pages).
Matsumoto et al., "Modification of nitroxyl contrast agents with multiple spins and their proton TI relaxivity", Magnetic Resonance Imaging, 2008, vol. 26, No. 1, pp. 117-121, cited in ISR and Japanese Notification of Reasons for Refusal (5 pages).

(Continued)

*Primary Examiner* — Nyeemah A Grazier
(74) *Attorney, Agent, or Firm* — Westerman, Hattori, Daniels & Adrian, LLP

(57) ABSTRACT

The present invention provides a compound represented by General Formula (I). The compound according to the present invention prevents the liquid crystal composition from being deteriorated due to light, has high compatibility with the liquid crystal composition, and does not impair the storage stability of the liquid crystal composition, thus the compound is useful as a constituent member of a liquid crystal composition. Since the liquid crystal composition and the liquid crystal display element containing the compound of the present invention exhibit UV resistance and have a high VHR, it is possible to obtain a liquid crystal display element with excellent display quality in which display defects such as burn-in and display unevenness do not occur or are suppressed.

(I)

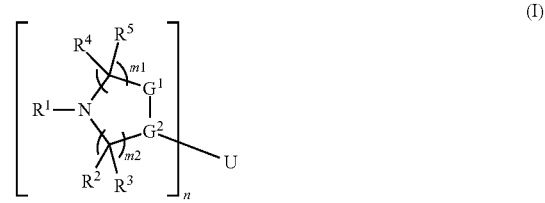

6 Claims, No Drawings

(56) References Cited

FOREIGN PATENT DOCUMENTS

| | | | | |
|---|---|---|---|---|
| JP | 60-500669 A | 5/1985 | | |
| JP | 60-190786 A | 9/1985 | | |
| JP | 2-265966 A | 10/1990 | | |
| JP | 5-117324 A | 5/1993 | | |
| JP | 9-291282 A | 11/1997 | | |
| JP | 2002-256267 A | 9/2002 | | |
| JP | 2004-507607 A | 3/2004 | | |
| JP | 2004-524259 A | 8/2004 | | |
| JP | 2012-515206 A | 7/2012 | | |
| JP | 2013-36038 A | 2/2013 | | |
| JP | 2014-505745 A | 3/2014 | | |
| JP | 2014-505746 A | 3/2014 | | |
| JP | 2016-132678 A | 7/2016 | | |
| WO | 93/22662 A1 | 11/1993 | | |
| WO | 2014/045783 A1 | 3/2014 | | |
| WO | 2014/066230 A1 | 5/2014 | | |
| WO | WO-2014136059 A2 * | 9/2014 | ............ | C07D 223/04 |
| WO | WO-2015107071 A1 * | 7/2015 | ............... | C12N 9/93 |
| WO | 2017/038617 A1 | 3/2017 | | |

OTHER PUBLICATIONS

Bosman et al., "Five Generations of Nitroxyl-Functionalized Dendrimers", Macromolecules, 1997, vol. 30, No. 12, pp. 3606-3611, cited in ISR and Japanese Notification of Reasons for Refusal (6 pages).
Gallez et al., "Evaluation of Nonionic Nitroxyl Lipids as Potential Organ-Specific Contrast Agents for Magnetic Resonance Imaging", Magnetic Resonance Imaging, 1992, vol. 10, No. 3, pp. 445-455, cited in ISR and Japanese Notification of Reasons for Refusal (11 pages).
Valera et al., "A Modular Approach for the Synthesis of Nanometer-Sized Polynitroxide Multi-Spin Systems", Journal of Organic Chemistry, 2014, vol. 79, No. 17, pp. 8313-8323, cited in ISR and Japanese Notification of Reasons for Refusal (11 pages).
Schuetz et al., "4,4',4"-(Methanetriyl)triphenyl tris-(2,2,5,5-tetramethyl-1-oxyl-3-pyrroline-3-carboxylate) benzene trisolvate", Acta Crystallographica Section E: Structure Reports Online, 2010, vol. 66, No. 4, pp. o729-o730, cited in ISR and Japanese Notification of Reasons for Refusal (18 pages).
Sen' et al., "Synthesis and Structure of Products of Hydroxylamine Acylation with 3-Carboxy-2,2,5,5-tetramethylpyrrolinoxyl Derivatives", Russian Journal of Organic Chemistry, 2009, vol. 45, No. 8, pp. 1189-1199, cited in ISR and Japanese Notification of Reasons for Refusal (11 pages).
Jaszberenyi et al., "Synthesis, Equilibrium and Kinetic Properties of Gd3+ Complexes of Three DTPA-Bis(Amide) Derivatives Containing Stable Nitroxide Free Radical Substituents", European Journal of Inorganic Chemistry, 2003, No. 19, pp. 3601-3608, cited in ISR and Japanese Notification of Reasons for Refusal (8 pages).
Martin et al., "Novel pH-Sensitive Nitroxide Di- and Tri-radical Spin Labels", Journal of the Chemical Society, Chemical Communications, 1995, No. 7, pp. 723-724, cited in ISR and Japanese Notification of Reasons for Refusal (2 pages).
Brik, "Synthesis of Di and Polynitroxides by Favorskii Rearrangement of Polyamines on Cis-3,5-Dibromo-4-Oxo-2,2,6,6-Tetramethylpiperidin-1-Oxyl", Synthetic Communications, 1990, vol. 20, No. 10, pp. 1487-1495, cited in ISR and Japanese Notification of Reasons for Refusal (9 pages).
Brik et al., "Evaluation of MRI contrast by using polynitroxides: application to magnetic resonance imaging of lungs and liver" in French, Analusis, 1990, vol. 18, No. 3, pp. 179-184, cited in ISR and Japanese Notification of Reasons for Refusal (6 pages).
Shapiro et al., "Iminoxyl biradicals with polyene bridges, Izvestiya Akademii Nauk SSSR" in Russian, Seriya Khimicheskaya, 1976, No. 9, pp. 2124-2127, cited in ISR and Japanese Notification of Reasons for Refusal (4 pages).
Ferruti et al., "Synthesis of Mono-, Di-, and Polynitroxides. Classification of Electron Spin Resonance Spectra of Flexible Dinitroxides Dissolved in Liquids and Glasses", Journal of the American Chemical Society, 1970, vol. 92, No. 12, pp. 3704-3713, cited in ISR and Japanese Notification of Reasons for Refusal (10 pages).
Krinitskaya,L. A. et al, Individual iminoxyl polyradicals of hydrogenated pyrrole, Zhurnal Organicheskoi Khimii in Russian, 1966, vol. 2, No. 7, pp. 1301-1305, cited in ISR and Japanese Notification of Reasons for Refusal (5 pages).
Corvaja et al., "Electron Spin Resonance Studies of Nitroxide Radicals and Biradicals in Nematic Solvents", Journal of the American Chemical Society, 1970, vol. 92, No. 13, pp. 3919-3924, cited in ISR and Japanese Notification of Reasons for Refusal (6 pages).
Yamaoka et al., "Spin-Labeled Metachromatic Dyes. I. ESR and Some Optical Properties of Spin-Labeled Proflavine in Solution, Liquid Crystal, and Stretched Film", Chemistry Letters, 1976, No. 12, pp. 1351-1354, cited in ISR and Japanese Notification of Reasons for Refusal (4 pages).
Setaka et al., "Orientation of Some Nitroxide Spin Labels in the Lamellar Mesophases of Aerosol-OT-Water and Decanol-Decanoate-Water Systems", Journal of the American Chemical Society, 1975, vol. 97, No. 21, pp. 6013-6018, cited in ISR and Japanese Notification of Reasons for Refusal (6 pages).
Hatano et al., "Facile Synthesis of 3-Methoxycarbonyl-2,2,5,5-Tetra-Methylpyrrolidine-1-Oxyl and Derivatives", Heterocycles, 2010, vol. 81, No. 2, pp. 349-356, cited in ISR and Japanese Notification of Reasons for Refusal (8 pages).
Chemical Abstract, 1987, vol. 107, p. 672, 107:39524b, Kyazimov et. al., "Liquid-phase catalytic oxidation of dimethyl phthalate and allyl chloride", Neftekhimiya, 1986, vol. 26, No. 4, pp. 549-553, cited in ISR and Japanese Notification of Reasons for Refusal (1 page).
International Search Report dated Nov. 15, 2016, issued in counterpart International Application No. PCT/JP2016/074474 (8 pages).
Notification of Reasons for Refusal dated Aug. 3, 2017, issued in counterpart Japanese Patent Application No. 2017-529113, w/English machine translation (12 pages).

* cited by examiner

STABILIZER COMPOUND, LIQUID CRYSTAL COMPOSITION, AND DISPLAY ELEMENT

TECHNICAL FIELD

The present invention relates to a stabilizer compound.

BACKGROUND ART

Liquid crystal display elements are used for not only watches and calculators, but also various electrical equipment for foods, various measuring instruments, automobile panels, word processors, electronic notebooks, printers, computers, televisions, clocks, advertisement display boards, and the like. Typical examples of liquid crystal display systems include twisted nematic (TN) type systems, super twisted nematic (STN) type systems, dynamic light scattering (DS) type systems, guest and host (GH) type systems, in-plane switching (IPS) type systems, optically compensated birefringence (OCB) type systems, electrically controlled birefringence (ECB) type systems, vertically aligned (VA) type systems, color super homeotropic (CSH) type systems, and the like. In addition, examples of driving systems include static driving, multiplex driving, simple matrix systems, and active matrix (AM) systems driven by thin film transistors (TFT), thin film diodes (TFD), and the like.

Among these, in particular, display systems such as IFS type systems and VA type systems, using AM driving are used for display elements which are melted at a high speed and a high viewing angle, for example, televisions, or the like.

Nematic liquid crystal compositions used for these display systems are required to be driven at a low voltage and to have high speed responsiveness and a wide operating temperature range. That is, it is required that the absolute value of $\Delta\varepsilon$ be large, the viscosity ($\eta$) be low, and the nematic phase-isotropic liquid phase transition temperature ($T_{ni}$) be high. In addition, from the setting of $\Delta n \times d$ which is the product of the refractive index anisotropy ($\Delta n$) and the cell gap (d), it is necessary to adjust $\Delta n$ of the liquid crystal composition to an appropriate range in accordance with the cell gap. In addition, in the case of applying the liquid crystal display element to a television or the like, since high-speed responsiveness is emphasized, a liquid crystal composition having a low viscosity ($\eta$) and small $\gamma_1$ is required.

In addition to the requirements for the physical properties of these liquid crystal compositions, liquid crystal compositions used for liquid crystal display elements are required to be stable against external stimuli such as moisture, air, heat, and light. When the stability against external stimulation is impaired, display defects such as burn-in and display unevenness occur in the liquid crystal display element. In order to obtain a liquid crystal composition and a liquid crystal display element which do not cause or are unlikely to cause display defects such as burn-in and display unevenness, it is considered that a high voltage holding ratio (VHR) is indispensable and, for that purpose, it is known that a high VHR can be maintained by adding an antioxidant, an ultraviolet absorber, or a light stabilizer to the liquid crystal composition (refer to PTLs 1 to 3).

From the above, there is a need for a liquid crystal composition which achieves a high VHR while satisfying the requirements of the physical properties of the liquid crystal composition and, to fulfill this need, there is a demand for novel antioxidants, ultraviolet absorbers, or light stabilizers which suppress decreases in the VHR.

CITATION LIST

Patent Literature

[PTL 1] JP-A-2002-256267
[PTL 2] JP-A-2014-505745
[PTL 3] JP-A-2014-505746

SUMMARY OF INVENTION

Technical Problem

The problem to be solved by the present invention is to provide a compound which prevents deterioration of a liquid crystal composition by being added to the liquid crystal composition, which has high compatibility with the liquid crystal composition, and which does not impair the storage stability of the liquid crystal composition.

Solution to Problem

The present inventors conducted intensive studies to solve the problems described above, and as a result, completed the present invention. That is, the present invention provides a compound represented by General Formula (I):

[Chem. 1]

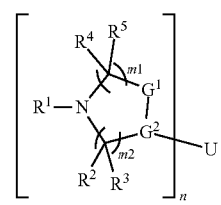

(in the formula, $R^1$ represents a hydrogen atom, a hydroxyl group, —O—, or an alkyl group having 1 to 20 carbon atoms; and one —$CH_2$— or two or more non-adjacent (—$CH_2$—)'s present in the alkyl group, except for —$CH_2$— directly bonded to a nitrogen atom adjacent to $R^1$, may each independently be substituted with —O—, —S—, —CO—, —CO—O—, —O—CO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —C≡C—, —Si(CH)$_2$—, a trans 1,4-cyclohexylene group, a 1,4-phenylene group, or a naphthalene-2,6-diyl group, and one or two or more hydrogen atoms in $R^1$ may each independently be substituted with a fluorine atom, a chlorine atom, or a cyano group, $R^2$, $R^3$, $R^4$, and $R^5$ each independently represent a hydrogen atom or an alkyl group having 1 to 8 carbon atoms; provided that $R^2$, $R^3$, $R^4$, and $R^5$ bonded to a carbon atom directly bonded to the nitrogen atom present in a ring structure represent an alkyl group, and when $R^2$ and $R^3$ and/or $R^4$ and $R^5$ represent an alkyl group, $R^2$ and $R^3$ and/or $R^4$ and $R^5$ may be bonded to each other to form a ring, -G$^1$-G$^2$- is a group represented by:

[Chem. 2]

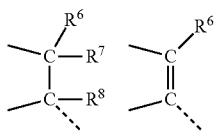

[Chem. 3]

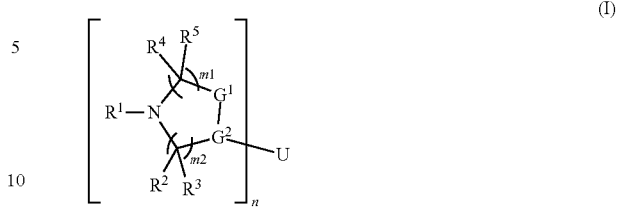

(I)

(in the formula, the broken lines represent a bond to U in General Formula (I), R$^6$, R$^7$, and R$^8$ each independently represent a hydrogen atom, a hydroxyl group, or an alkyl group having 1 to 20 carbon atoms, one —CH$_2$— or two or more non-adjacent (—CH$_2$—)'s present in the alkyl group may each independently be substituted with —O—, —S—, —CO—, —CO—O—, —O—CO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —C≡C—, —Si(CH$_3$)$_2$—, a trans 1,4-cyclohexylene group, a 1,4-phenylene group, or a naphthalene-2,6-diyl group, and one or two or more hydrogen atoms in the alkyl group may each independently be substituted with a fluorine atom, a chlorine atom, or a cyano group), U represents a hydrogen atom, a fluorine atom, a chlorine atom, a bromine atom, an iodine atom, a pentafluorosulfuranyl group, a nitro group, an amino group, a hydroxyl group, a mercapto group, or a monovalent to decavalent organic group, provided that a valency of U is the same as a number represented by n, m1 and m2 each independently represent an integer of 0 to 3, provided that m1+m2 represents an integer of 1, 2, or 4 to 6, and n represents an integer of 1 to 10, provided that plural R$^1$'s may be the same or different, plural R$^2$'s may be the same or different, plural R$^3$'s may be the same or different, plural R$^4$'s may be the same or different, plural R$^5$'s may be the same or different, plural n's may be the same or different, plural m$^2$'s may be the same or different, and plural -G$^1$-G$^2$-'s may be the same or different, and also provides a composition containing the compound and a display element.

Advantageous Effects of Invention

The compound according to the present invention prevents the liquid crystal composition from being deteriorated due to light, has high compatibility with the liquid crystal composition, and does not impair the storage stability of the liquid crystal composition, thus the compound is useful as a constituent member of a liquid crystal composition. Since the liquid crystal composition and the liquid crystal display element containing the compound of the present invention exhibit UV resistance and have a high VHR, it is possible to obtain a liquid crystal display element with excellent display quality in which display defects such as burn-in and display unevenness do not occur or are suppressed.

DESCRIPTION OF EMBODIMENTS

The liquid crystal composition of the present invention contains one or two or more of compounds represented by General Formula (I).

From the viewpoint of compatibility with the liquid crystal composition, R$^1$ in General Formula (I) is preferably a hydrogen atom, an alkyl group having 1 to 20 carbon atoms, an alkoxy group having 1 to 20 carbon atoms, or an alkenyl group having 2 to 20 carbon atoms, more preferably an alkyl group having 1 to 12 carbon atoms, an alkoxy group having 1 to 12 carbon atoms or an alkenyl group having 3 to 12 carbon atoms. The alkyl group, alkoxy group or alkenyl group is preferably linear or molecular, and is preferably linear. From the viewpoint of ease of production, a hydrogen atom or a linear alkyl group having 1 to 5 carbon atoms is particularly preferable. In addition, in order to increase the ability to prevent deterioration due to light, a hydrogen atom or a hydroxyl group is preferable, and a hydrogen atom is particularly preferable.

Among R$^2$, R$^3$, R$^4$, and R$^5$, R$^2$, R$^3$, R$^4$, and R$^5$ bonded to the carbon atom directly bonded to the nitrogen atom present in the ring structure are preferably each independently an alkyl group having 1 to 4 carbon atoms, and particularly preferably a methyl group from the viewpoints of ease of availability of raw materials and stability of the compound. In addition, in order to facilitate the removal of polar impurities mixed therein during production, R$^2$ and R$^3$ and/or R$^4$ and R$^5$ are preferably bonded to each other to form a ring structure. In the case where m1 and/or m2 represents 2 or 3, R$^2$, R$^3$, R$^4$, and R$^5$ directly bonded to a carbon atom not directly bonded to the nitrogen atom present in the ring structure are preferably each independently a hydrogen atom or an alkyl group having 1 to 8 carbon atoms, preferably a hydrogen atom or an alkyl group having 1 to 4 carbon atoms, and, from the viewpoints of ease of availability of raw materials and stability of the compound, particularly preferably a hydrogen atom or a methyl group.

G$^1$-G$^2$ are groups represented by:

[Chem. 4]

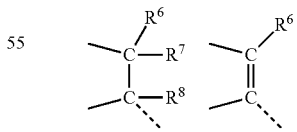

R$^6$, R$^7$, and R$^8$ in the group are preferably each independently a hydrogen atom or an alkyl group having 1 to 12 carbon atoms, preferably a hydrogen atom or an alkyl group having 1 to 8 carbon atoms, preferably a hydrogen atom or an alkyl group having 1 to 4 carbon atoms, and particularly preferably a hydrogen atom from the viewpoint of ease of production. The alkyl group is preferably linear or molecular, and is preferably linear. From the viewpoint of ease of production, $G^1$-$G^2$ is preferably —$CH_2$—CH—, or —CH=C—, and from the viewpoint of stability of the compound, particularly preferably —$CH_2$—CH—. In the case of m1=0 and m2=1, $R^6$, $R^7$, and $R^8$ are preferably each independently an alkyl group having 1 to 8 carbon atoms, more preferably an alkyl group having 1 to 4 carbon atoms, and, from the viewpoints of ease of availability of raw materials and stability of the compound, particularly preferably a methyl group. m1 and m2 each independently preferably represent an integer of 1 to 3, and preferably represent 1. m1+m2 preferably represents 2, or 4 to 6, preferably 2, 4, or 5, and more preferably 2. In the case where m1+m2 represents 1, it is preferable that m1 represents 0 and m2 represents 1. In the case where m1+m2 represents 2, it is preferable that m1 represents 1 and m2 represents 1. In the case where m1+m2 represents 4, it is preferable that m1 represents 2 and m2 represents 2. In the case where m1+m2 represents 5, it is preferable that m1 represents 2 and m2 represents 3. In the case where m1+m2 represents 6, it is preferable that m1 represents 3 and m2 represents 3. From the viewpoint of compatibility with the liquid crystal composition, n is preferably an integer of 1 to 4. In order to increase the storage stability of the liquid crystal composition, n is preferably 1 or 2. In addition, in order to increase the ability to prevent deterioration due to light, n is preferably 3 or 4 since the number of hindered amine structures per unit of weight increases.

U preferably represents a hydrogen atom or a monovalent to tetravalent organic group.

The compound represented by General Formula (I) is preferably a compound represented by General Formula (I-a) to General Formula (I-g).

[Chem. 5]

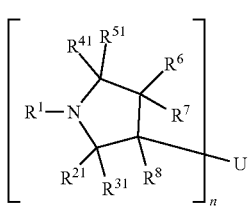
(I-a)

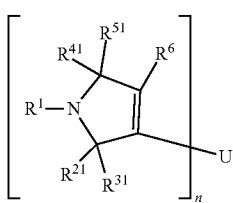
(I-b)

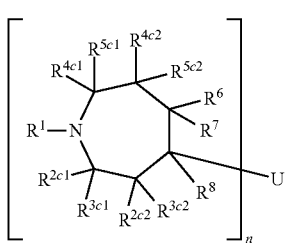
(I-c)

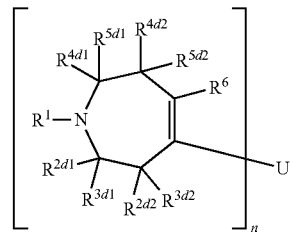
(I-d)

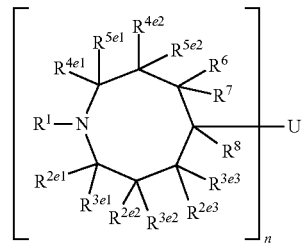
(I-e)

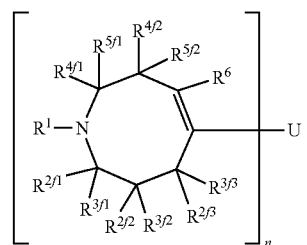
(I-f)

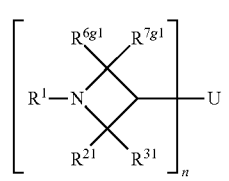
(I-g)

In the formulas, $R^1$, $R^6$ to $R^8$, n, and U each independently represent the same meanings as $R^1$, $R^6$ to $R^8$, n, and U in General Formula (I), $R^{21}$, $R^{31}$, $R^{41}$, $R^{51}$, $R^{2c1}$ to $R^{4/1}$, $R^{3c1}$ to $R^{3/1}$, $R^{4c1}$ to $R^{4/1}$, $R^{5c1}$ to $R^{5/1}$, $R^{6g1}$, and $R^{7g1}$ each independently represent an alkyl group having 1 to 8 carbon atoms, and $R^{2c2}$ to $R^{2/2}$, $R^{3c2}$ to $R^{3/2}$, $R^{4c2}$ to $R^{4/2}$, $R^{5c2}$ to $R^{5/2}$, $R^{2e3}$, $R^{2/3}$, $R^{3e3}$, and $R^{3/3}$ each independently represent a hydrogen atom or an alkyl group having 1 to 8 carbon atoms.

In General Formula (I), U is preferably a group represented by General Formula (U-1).

[Chem. 6]

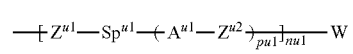
(U-1)

In the formula, $Z^{u1}$ and $Z^{u2}$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —SCF=, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—, —N=CH—, —CH=N—N=CH—, —CF=CF—, —C≡C—, or a single bond, $A^{u1}$ represents a group selected from the group consisting of (a) a 1,4-cyclohexylene group (one —$CH_2$— or two or more non-adjacent —$CH_2$— present in this group may be substituted with —O—), (b) a 1,4-phenylene group (one —CH= or two or more non-adjacent —CH= present in this group may be substituted with —N=), (c) a naphthalene-2,6-diyl group, a 1,2,3,4-tetrahydronaphthalene-2,6-diyl group, or a decahydronaphthalene-2,6-diyl group (one —CH= or two or more non-adjacent —CH= present in the naphthalene-2,6-diyl group or the 1,2,3,4-tetrahydronaphthalene-2,6-diyl group may be substituted with —N=), the group (a), the group (b), and the group (c) may each independently be substituted with a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, one —$CH_2$— or two or more non-adjacent (—$CH_2$—)'s present in the alkyl group may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —$OCF_2$—, —$CF_2O$—, or —C≡C—, $Sp^{u1}$ represents a single bond or an alkylene group having 1 to 10 carbon atoms and, in one —$CH_2$— or two or more non-adjacent (—$CH_2$—)'s present in the alkylene group, except for —$CH_2$— directly bonded to $Z^{u1}$ adjacent to $Sp^{u1}$, may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —$OCF_2$—, —$CF_2O$—, or —C≡C—, W represents a hydrogen atom, a fluorine atom, a chlorine atom, a bromine atom, an iodine atom, a pentafluorosulfuranyl group, a nitro group, an amino group, a hydroxyl group, a mercapto group, or a monovalent to decavalent organic group, provided that the valency of W is the same as a number represented by n in General Formula (I), pu1 represents an integer from 0 to 8, nu1 represents an integer of 1 to 10, provided that nu1 and n in General Formula (I) are the same number, and if any, plural $Z^{u1}$'s may be the same or different, plural $Z^{u2}$'s may be the same or different, plural $Sp^{u1}$'s may be the same or different, and plural $A^{u1}$'s may be the same or different.

In General Formula (U-1), from the viewpoint of ease of production, $Z^{u1}$ and $Z^{u2}$ are preferably —$CH_2O$—, —COO—, —OCO—, —CO—NH—, —COO—CH=CH—, —COO—$CH_2CH_2$—, —COO—$CH_2$—, —$CH_2$—OCO—, —CH=CH—, —C≡C—, or a single bond, and more preferably —$CH_2O$—, —COO—, —CO—NH—, or a single bond. $Sp^{u1}$ is preferably a single bond or an alkylene group having 1 to 8 carbon atoms, more preferably a single bond or an alkylene group having 1 to 6 carbon atoms, provided that one —$CH_2$— or two or more non-adjacent (—$CH_2$—)'s present in the alkylene group, except for —$CH_2$— directly bonded to $Z^{u1}$ adjacent to $Sp^{u1}$, may each independently be substituted with —O—, —COO—, —OCO—, —CH=CH—, or —C≡C—. From the ease of availability of raw materials and ease of synthesis, $Sp^{u1}$ is preferably a single bond.

$A^{u1}$ preferably represents a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and these groups are each independently preferably unsubstituted or may be substituted with a cyano group, a fluorine atom, a chlorine atom, a methyl group, or a methoxy group.

From the viewpoint of compatibility with the liquid crystal composition and ease of production, pu1 is preferably an integer of 0 to 3, and preferably an integer of 1 to 3. nu1 represents the same number as n in General Formula (I). W preferably represents a hydrogen atom or a monovalent to tetravalent organic group, provided that the valency of W is the same as a number represented by n in General Formula (I). For example, in the case where n in General Formula (I) represents 1, that is, in the case where nu1 in General Formula (U-1) is 1 and the valency of W is 1, General Formula (U-1) represents:

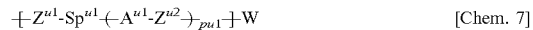 [Chem. 7]

Further, General Formula (U-1) represents:

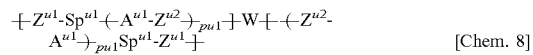 [Chem. 8]

in the case where n in General Formula (I) represents 2, that is, when nu1 in General Formula (U-1) is 2 and the valency of W is 2.

$Z^{u1}$ in General Formula (U-1) is bonded to $G^2$ in General Formula (I). Here, in the case where $Z^{u1}$ is a single bond, $Sp^{u1}$ is a single bond, and pu1 represents 0, a structure in which $G^2$ in General Formula (I) and W in General Formula (U-1) are bonded is formed, and in the case where $Z^{u1}$ is a single bond, $Sp^{u1}$ is a single bond, and pu1 represents an integer of 1 to 3, a structure in which $G^2$ in General Formula (I) and $A^{u1}$ in General Formula (U-1) are bonded is formed. In addition, in General Formula (U-1), a structure including —O—O—, —NH—O—, —O—NH—, —O—S—, and —S—O— groups is not formed.

In General Formula (I), in the case where n in General Formula (I) represents 1, that is, in the case where nu1 in General Formula (U-1) is 1 and the valency of W is 1, W in General Formula (U-1) preferably represents a hydrogen atom, a fluorine atom, a chlorine atom, a bromine atom, an iodine atom, a pentafluorosulfuranyl group, a nitro group, an amino group, a hydroxyl group, a mercapto group, or an alkyl group having 1 to 12 carbon atoms, and one —$CH_2$— or two or more non-adjacent (—$CH_2$—)'s present in the alkyl group may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —$OCF_2$—, —$CF_2O$—, or —C≡C—. From the viewpoint of ease of production, W preferably represents an alkyl group having 1 to 8 carbon atoms, and the alkyl group may be linear or branched, but is preferably linear.

Specifically, compounds in which n in General Formula (I) represents 1 are preferably compounds represented by Formulas (I-1-1) to (I-1-109).

[Chem. 9]

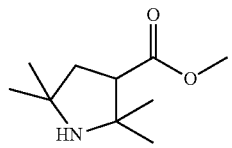

(I-1-1)

-continued
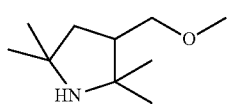
(I-1-2)
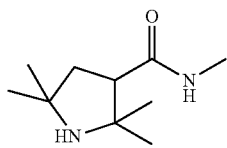
(I-1-3)
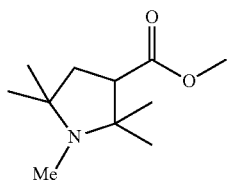
(I-1-4)
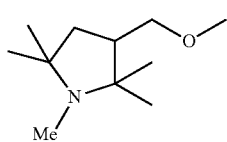
(I-1-5)
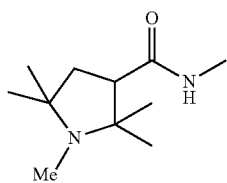
(I-1-6)
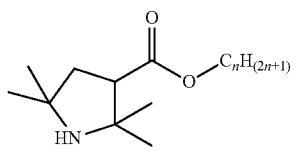
(I-1-7)
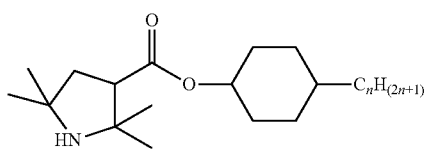
(I-1-8)
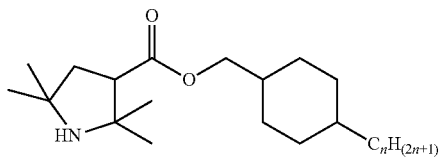
(I-1-9)
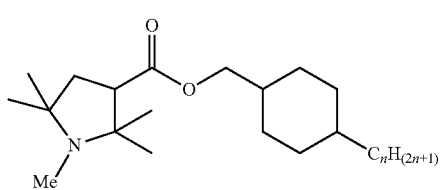
(I-1-10)
-continued
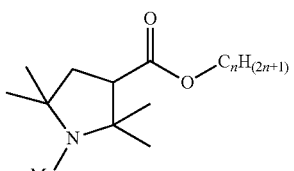
(I-1-11)
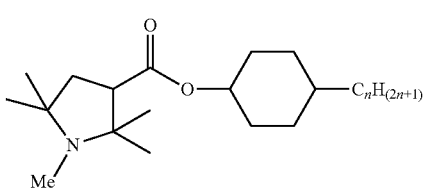
(I-1-12)
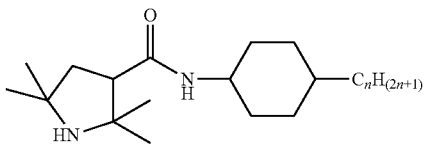
(I-1-13)
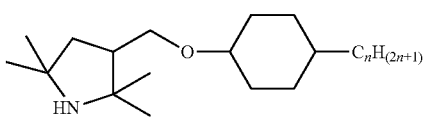
(I-1-14)
[Chem. 10]
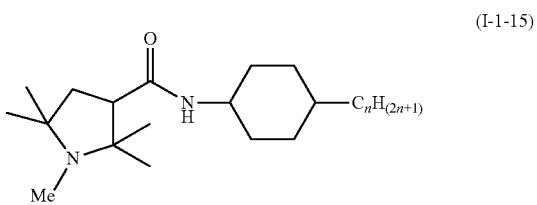
(I-1-15)
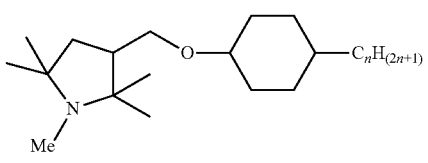
(I-1-16)
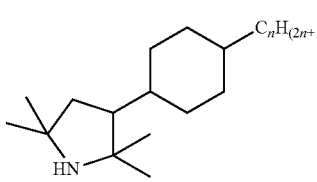
(I-1-17)
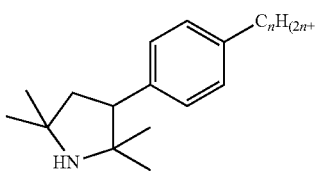
(I-1-18)
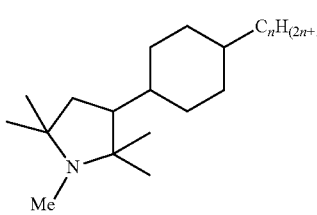
(I-1-19)

-continued
(I-1-20)
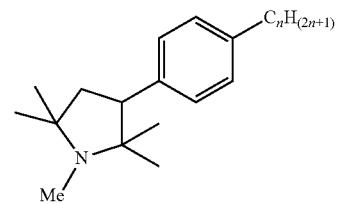
(I-1-21)
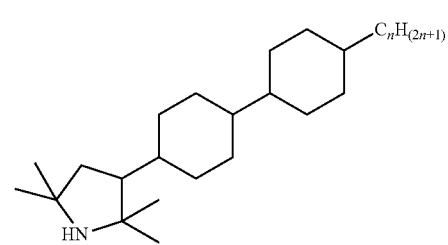
(I-1-22)
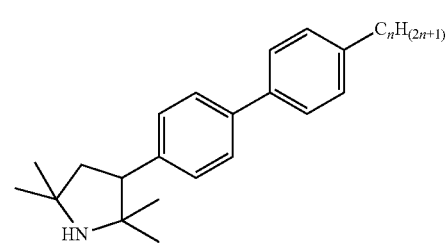
(I-1-23)
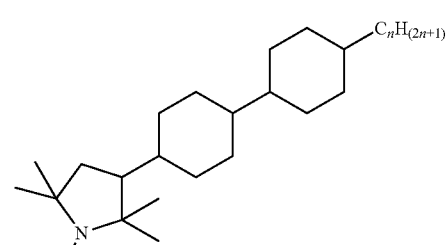
(I-1-24)
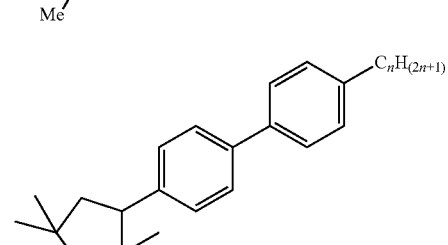
(I-1-25)
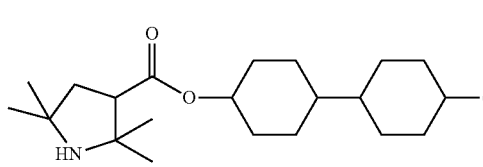
(I-1-26)
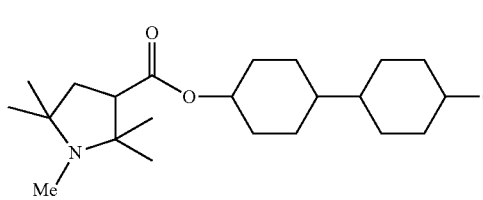
-continued
[Chem. 11]
(I-1-27)
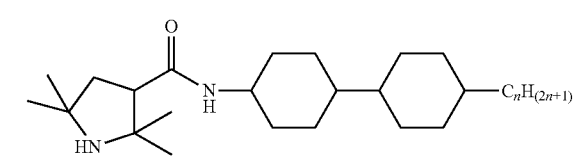
(I-1-28)
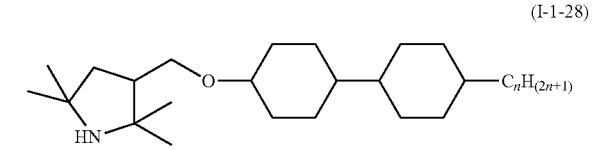
(I-1-29)
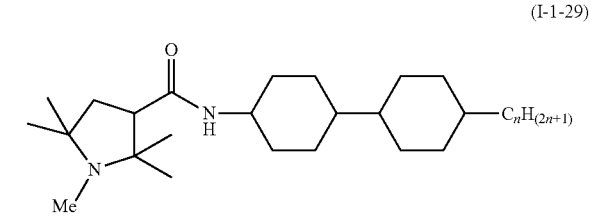
(I-1-30)
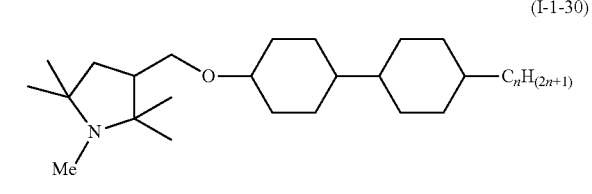
(I-1-31)
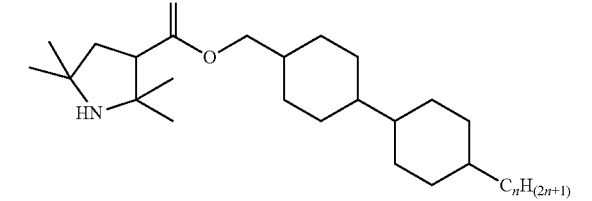
(I-1-32)
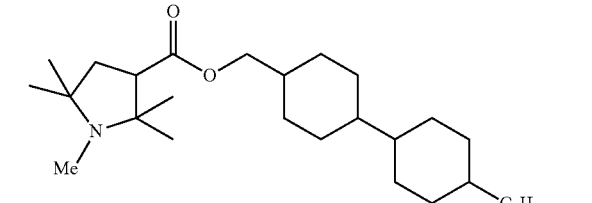
(I-1-33)
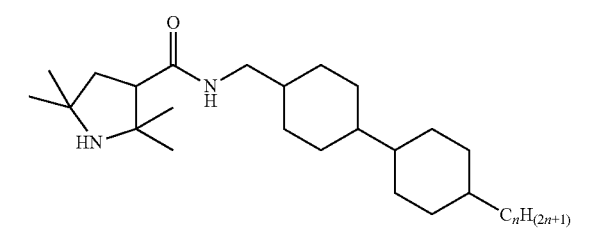

(I-1-34)
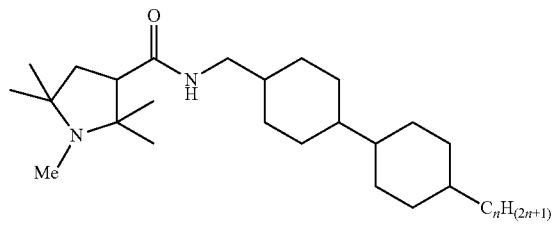
(I-1-35)
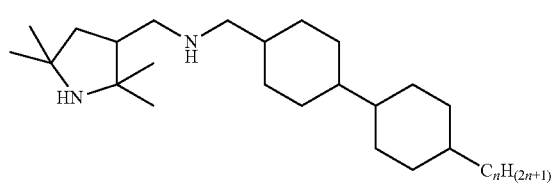
(I-1-36)
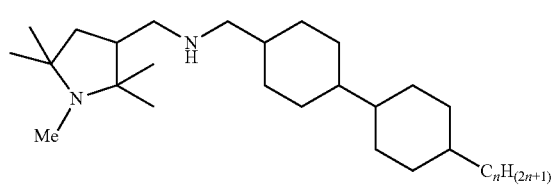
(I-1-37)
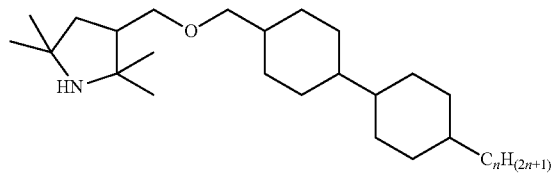
(I-1-38)
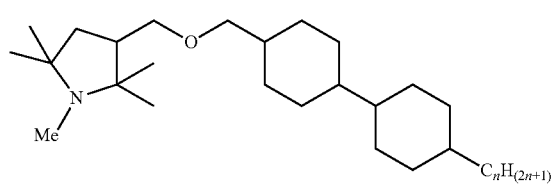
(I-1-39)
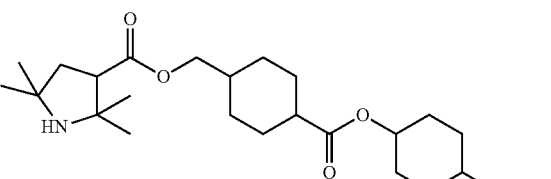
(I-1-40)
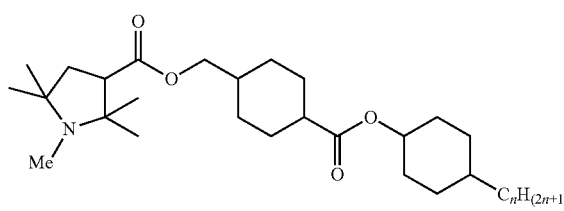
(I-1-41)
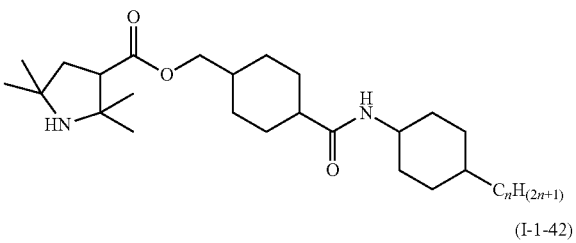
(I-1-42)
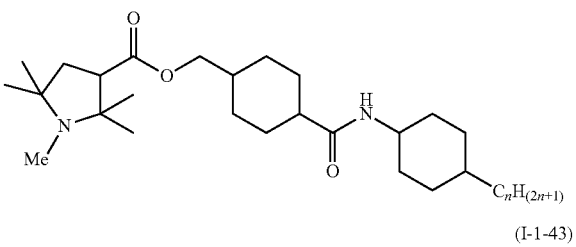
(I-1-43)
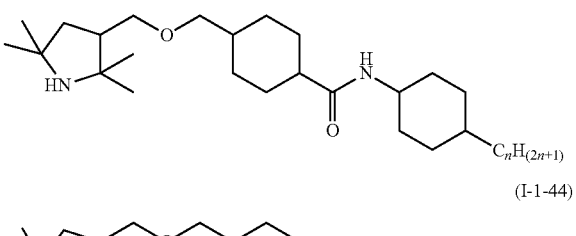
(I-1-44)
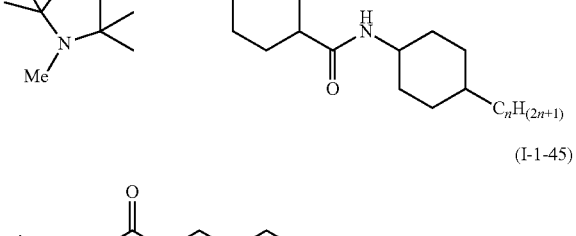
(I-1-45)
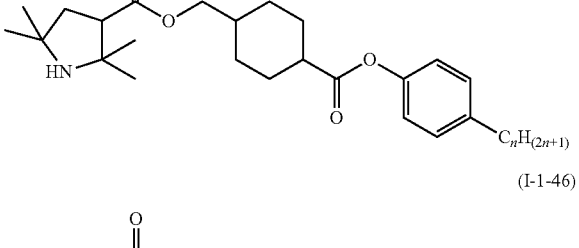
(I-1-46)
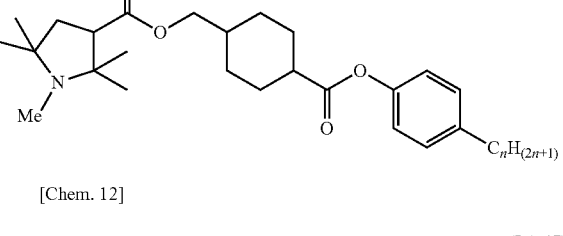
[Chem. 12]
(I-1-47)
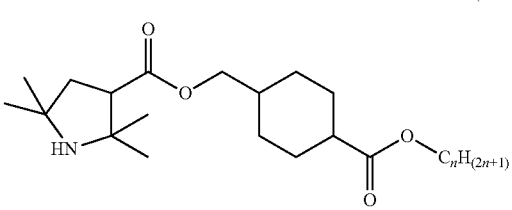

(I-1-48)
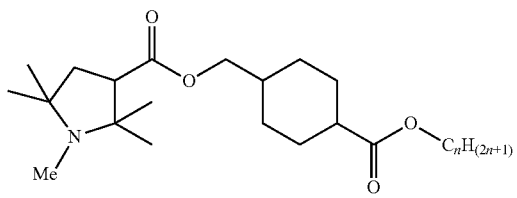
(I-1-49)
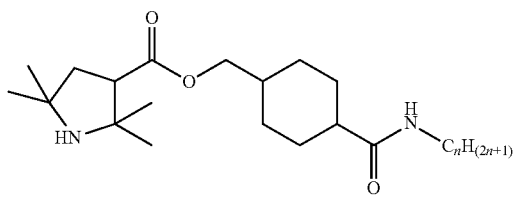
(I-1-50)
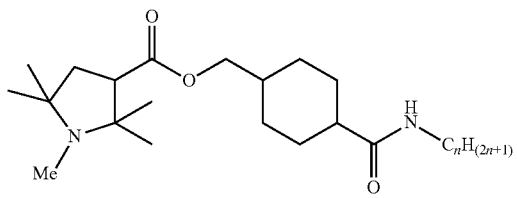
(I-1-51)
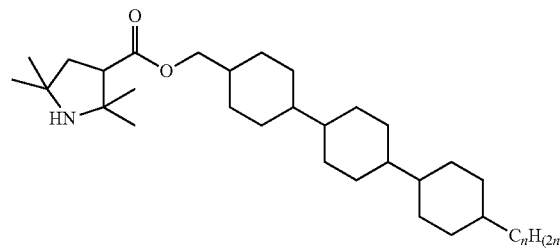
(I-1-52)
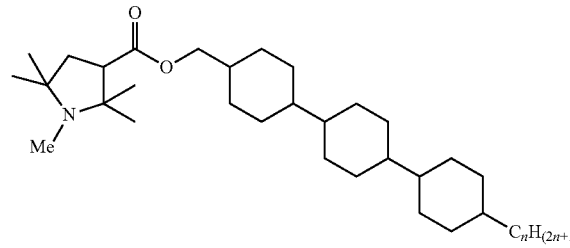
(I-1-53)
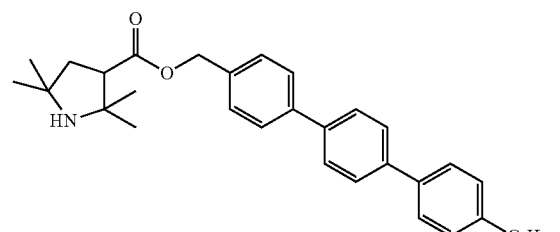
(I-1-54)
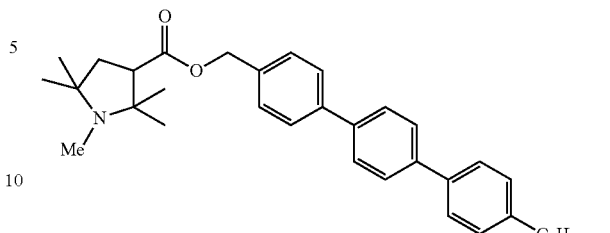
(I-1-55)
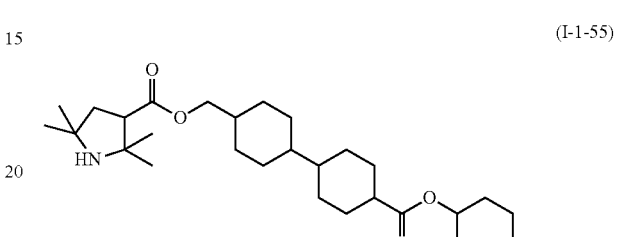
(I-1-56)
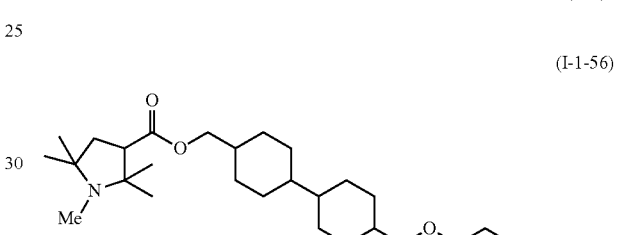
(I-1-57)
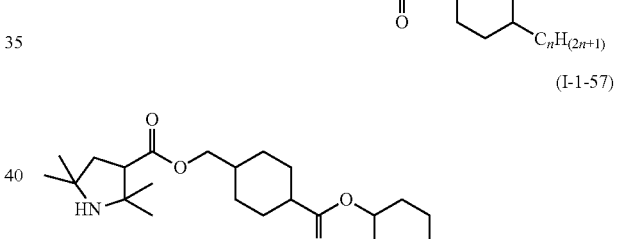
(I-1-58)
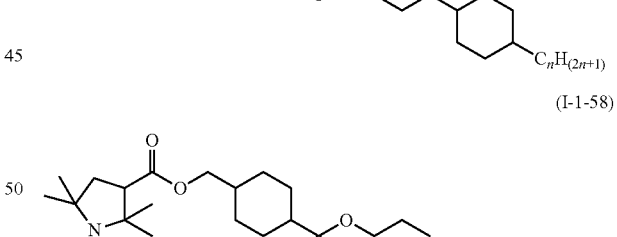
(I-1-59)
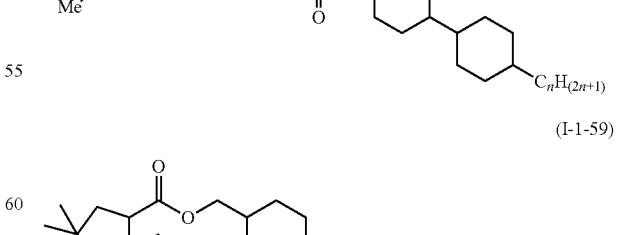
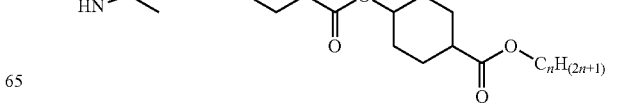

(I-1-60) 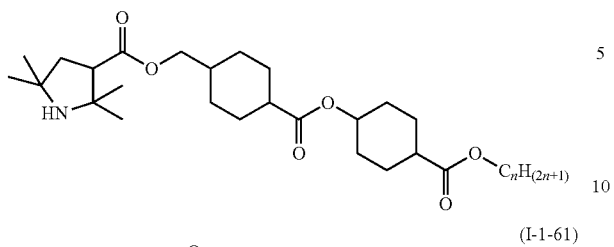
(I-1-61) 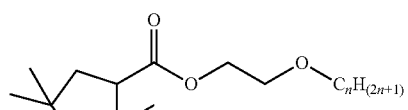
(I-1-62) 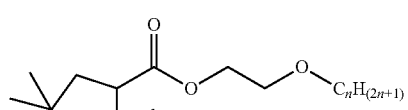
(I-1-63) 
(I-1-64) 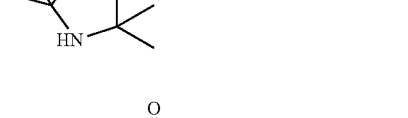
[Chem. 13]
(I-1-65) 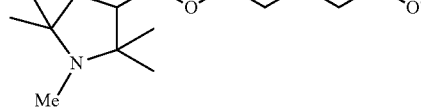
(I-1-66) 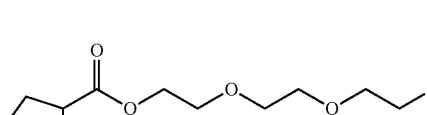
(I-1-67) 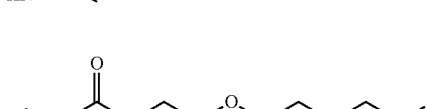
(I-1-68) 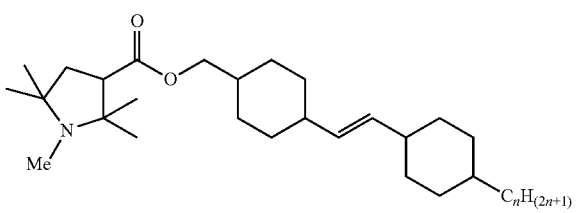
(I-1-69) 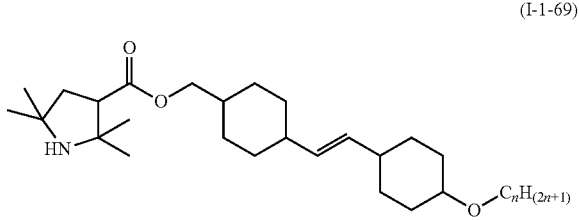
(I-1-70) 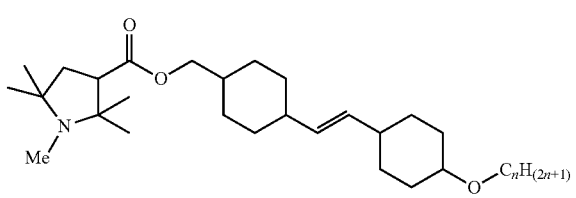
(I-1-71) 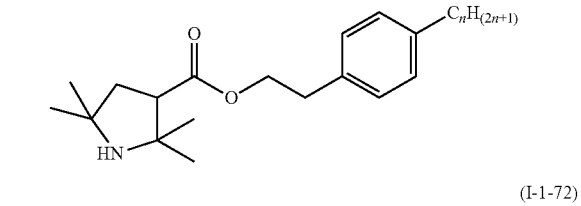
(I-1-72) 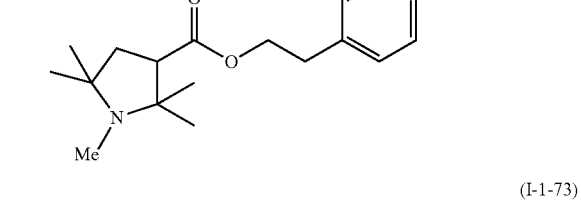
(I-1-73) 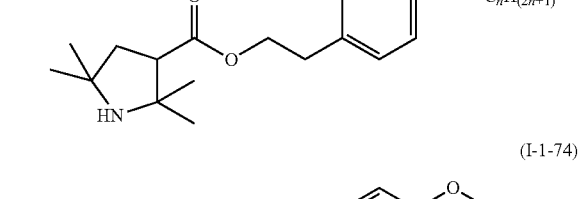
(I-1-74)

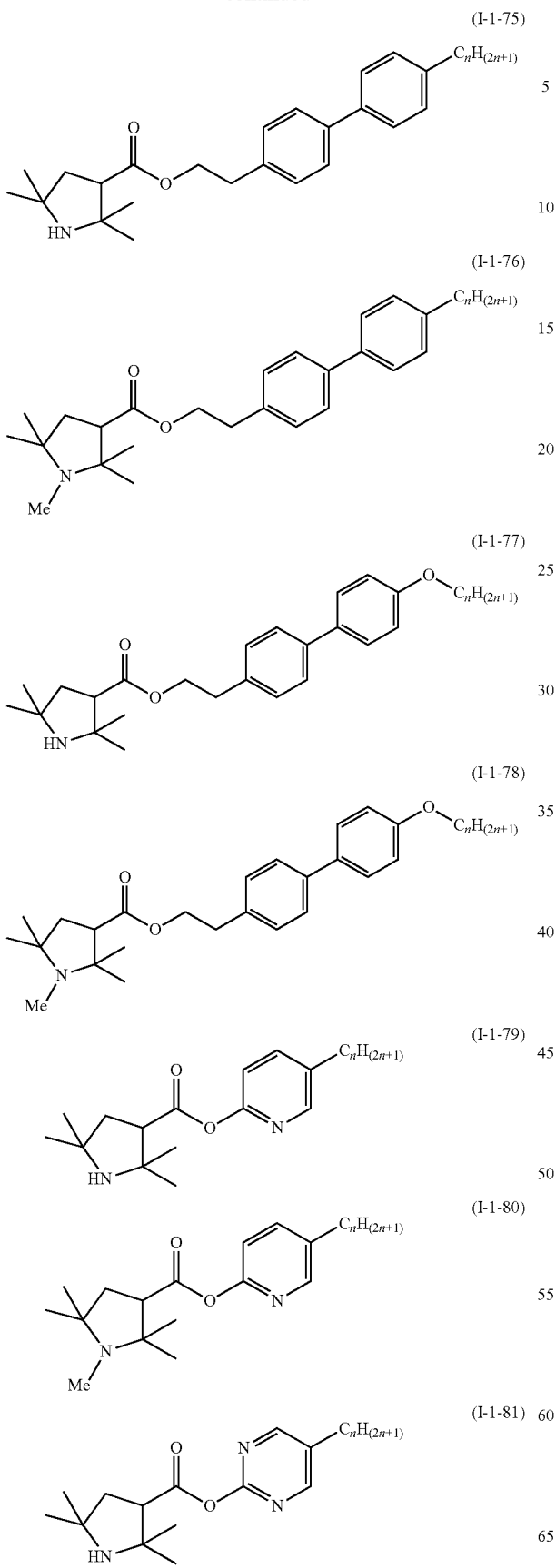
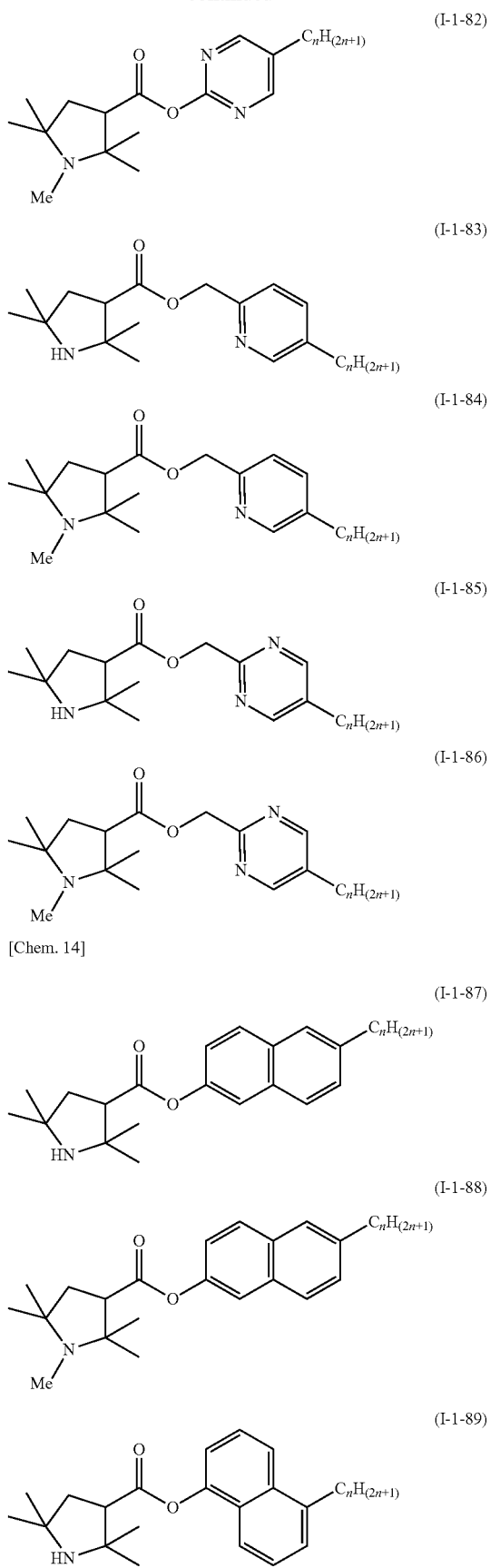

-continued (I-1-90)
(I-1-91)
(I-1-92)
(I-1-93)
(I-1-94)
(I-1-95)
(I-1-96)
(I-1-97)
(I-1-98)
(I-1-99)
(I-1-100)
(I-1-101)
(I-1-102)
(I-1-103)
(I-1-104)

-continued (I-1-105)

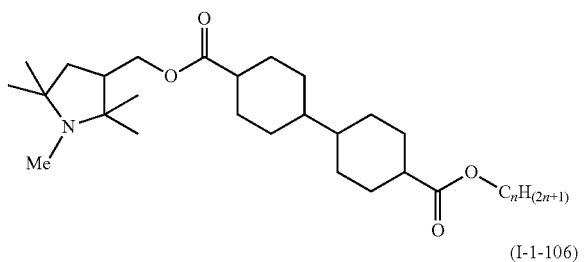

(I-1-106)

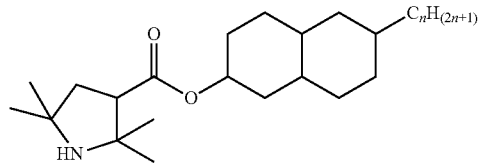

(I-1-107)

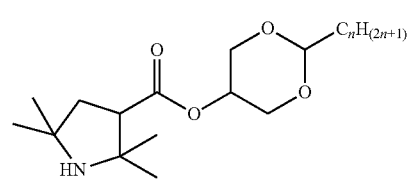

(I-1-108)

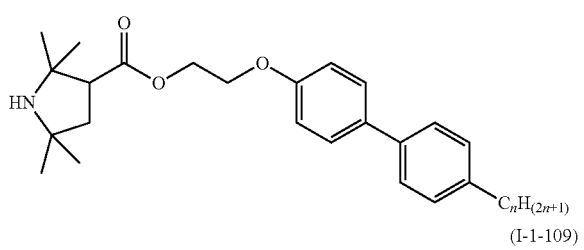

(I-1-109)

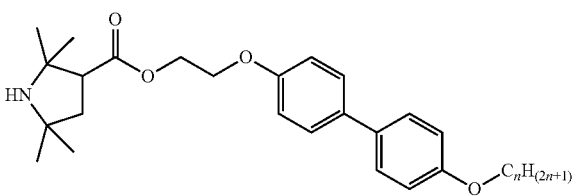

In the formulas, Me represents a methyl group and n in $C_nC_{(2n+1)}$ represents an integer of 1 to 8.

$C_nC_{(2n+1)}$ in the above formulas may be linear or branched.

In General Formula (I), in the case where n in General Formula (I) represents 2, that is, in the case where nu1 in General Formula (U-1) is 2 and the valency of W is 2, W in General Formula (U-1) preferably represents an alkylene group having 1 to 10 carbon atoms, and one —CH$_2$— or two or more non-adjacent (—CH$_2$—)'s present in the alkylene group may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, —OCF$_2$—, —CF$_2$O—, or —C≡C—.

In addition, W preferably represents a group selected from the group consisting of (a) a 1,4-cyclohexylene group (one —CH$_2$— or two or more non-adjacent (—CH$_2$—)'s present in this group may be substituted with —O—), (b) a 1,4-phenylene group (one —CH═ or two or more non-adjacent —CH═ present in this group may be substituted with —N═), (c) a naphthalene-2,6-diyl group, a 1,2,3,4-tetrahydronaphthalene-2,6-diyl group, or a decahydronaphthalene-2,6-diyl group (one —CH═ or two or more non-adjacent —CH═ present in the naphthalene-2,6-diyl group or the 1,2,3,4-tetrahydronaphthalene-2,6-diyl group may be substituted with —N═), the group (a), the group (b), and the group (c) may each independently be substituted with a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, and one —CH$_2$— or two or more non-adjacent (—CH$_2$—)'s present in the alkyl group may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, —OCF$_2$—, —CF$_2$O—, or —C≡C—.

In the case where the valency of W is 2, W in General Formula (U-1) preferably represents an alkylene group having 1 to 8 carbon atoms, more preferably an alkylene group having 1 to 6 carbon atoms, and the alkylene group may be linear or branched, but is preferably linear. In addition, one —CH$_2$— or two or more non-adjacent (—CH$_2$—)'s present in the alkylene group may each independently be substituted with —O—, —COO—, —OCO—, —CH═CH—, or —C≡C—. In addition, W preferably represents a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and these groups are each independently preferably unsubstituted, or may be substituted with a cyano group, a fluorine atom, a chlorine atom, a methyl group, or a methoxy group.

As the compound in which n represents 2 in General Formula (I), the compound represented by General Formula (I-2-a) is preferable.

[Chem. 15]

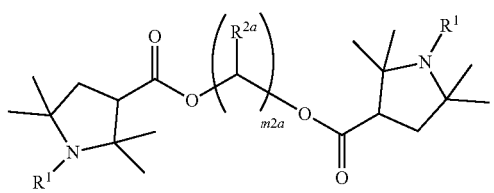

(I-2-a)

In the formula, $R^1$ represents the same meaning as $R^1$ in Formula (I), $R^{2a}$ represents a hydrogen atom or an alkyl group having 1 to 10 carbon atoms, $m^{2a}$ represents an integer of 0 to 10, and, in the case where $m^{2a}$ represents 2 to 10, plural $R^{2a}$'s each independently may be the same or different.

In General Formula (I-2-a), $R^{2a}$ preferably represents a hydrogen atom, a methyl group, or an ethyl group.

$m^{2a}$ preferably represents an integer of 1 to 7.

General Formula (I-2-a) more preferably represents General Formula (I-2-a1).

[Chem. 16]

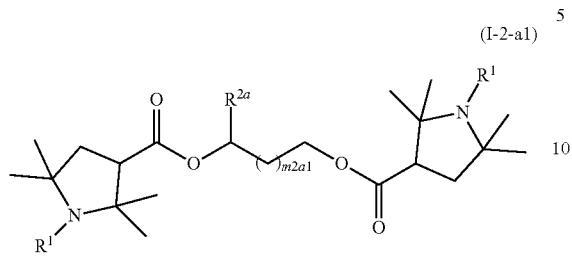

(I-2-a1)

In the formula, $R^1$ represents the same meaning as $R^1$ in General Formula (I), $R^{2a}$ represents the same meaning as $R^{2a}$ in General Formula (I-2-a), and $m^{2a1}$ represents an integer of 0 to 9.

Specifically, as the compound in which n in General Formula (I) represents 2, compounds represented by Formulas (I-2-1) to (I-2-129) are preferable.

[Chem. 17]

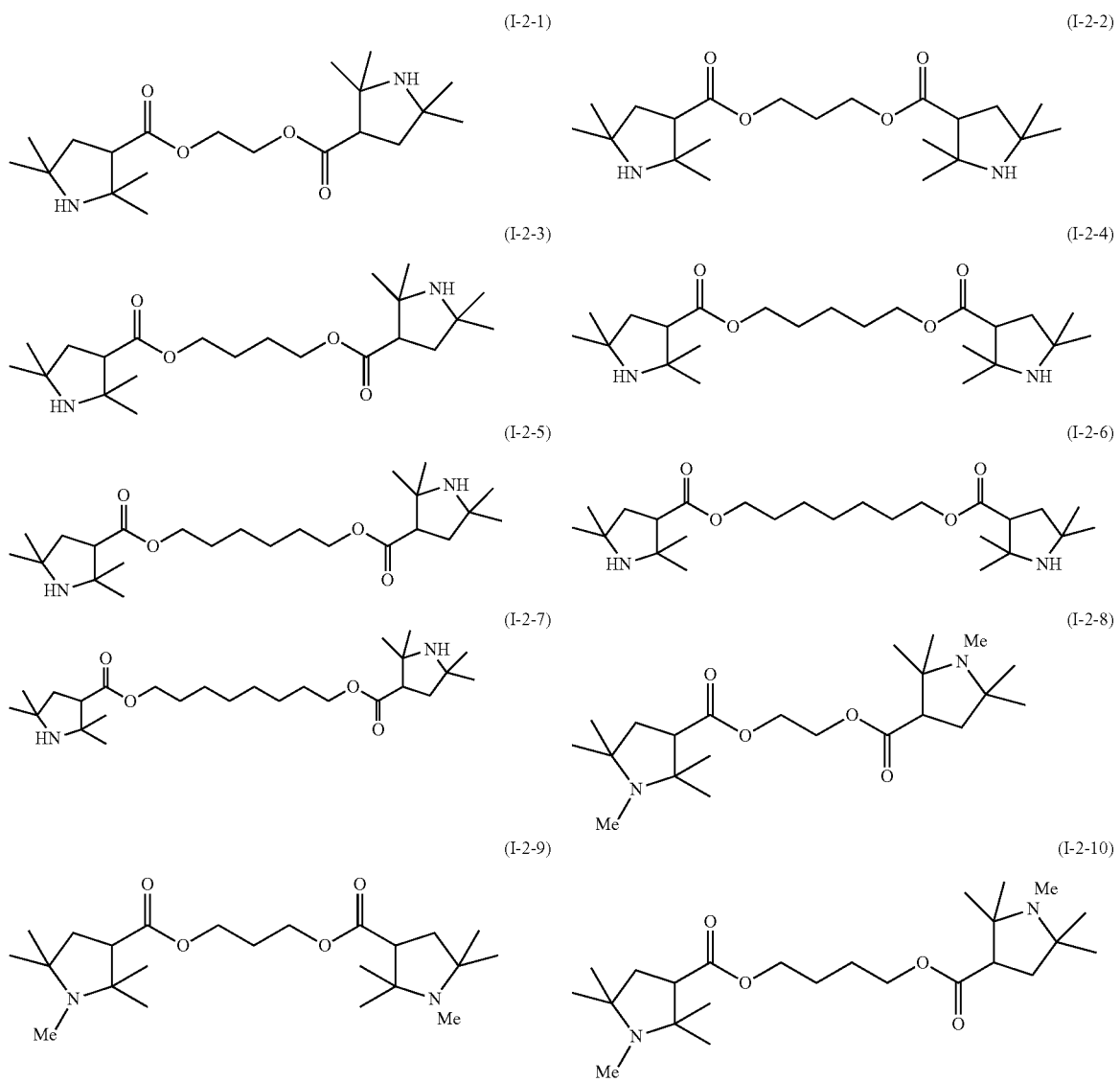

-continued
(I-2-11)
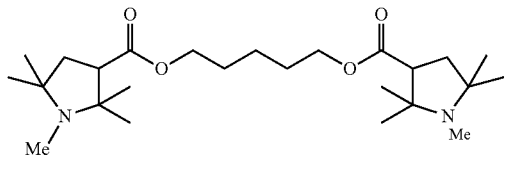
(I-2-13)
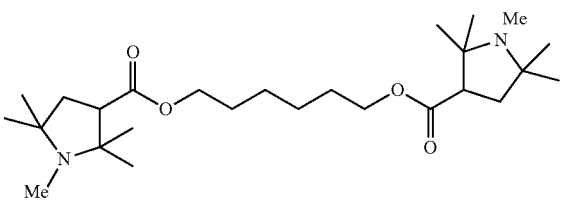
(I-2-14)
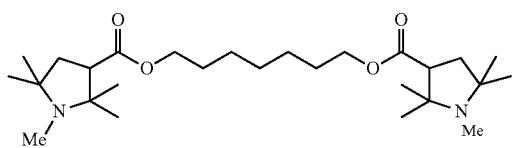
(I-2-15)
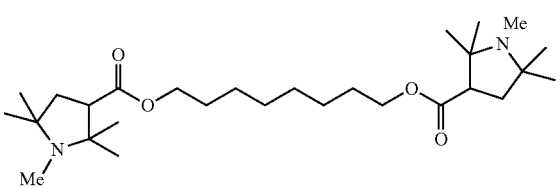
(I-2-16)
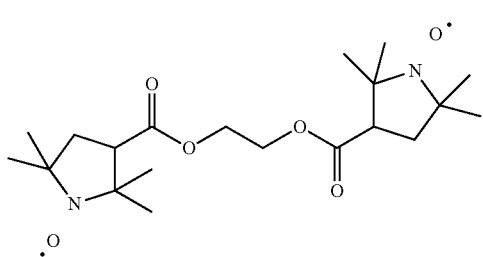
(I-2-17)
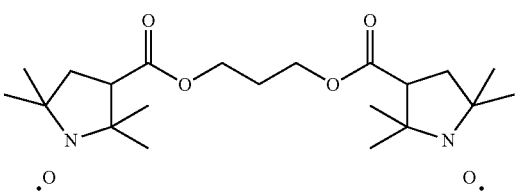
(I-2-18)
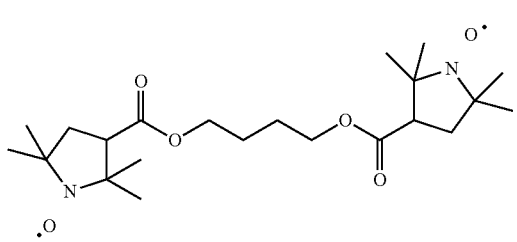
(I-2-19)
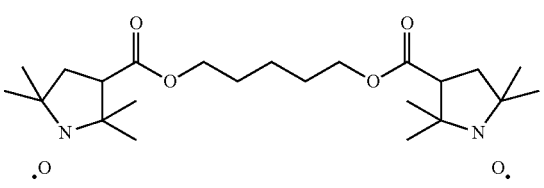
(I-2-20)
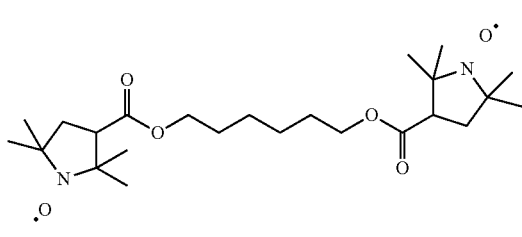
(I-2-21)
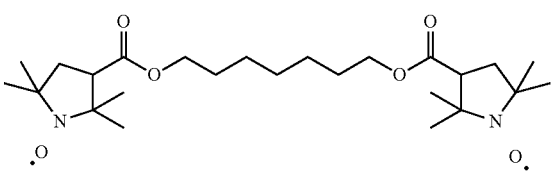
(I-2-22)
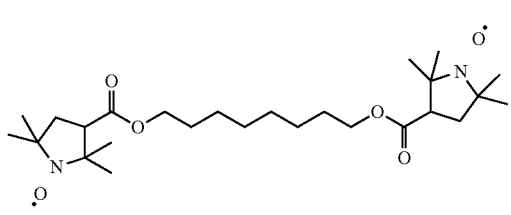
(I-2-23)
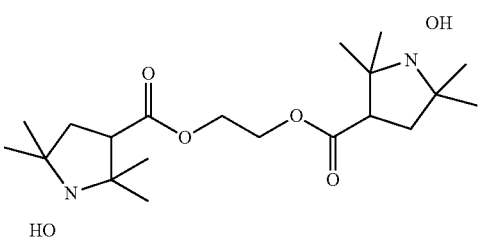

-continued
(I-2-24)
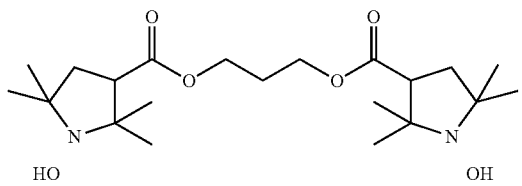
(I-2-25)
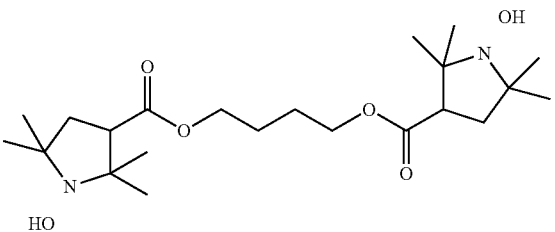
(I-2-26)
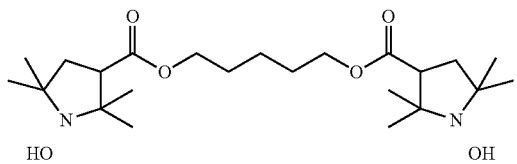
(I-2-27)
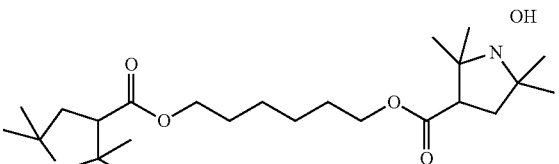
(I-2-28)
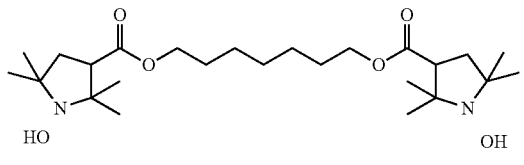
(I-2-29)
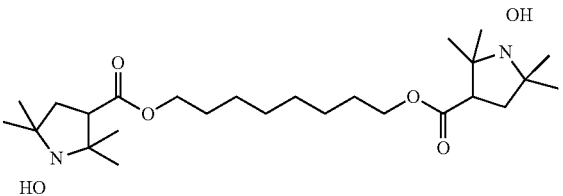
[Chem. 18]
(I-2-30)
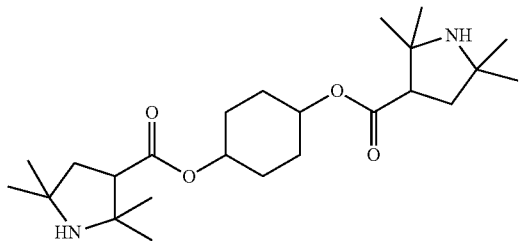
(I-2-31)
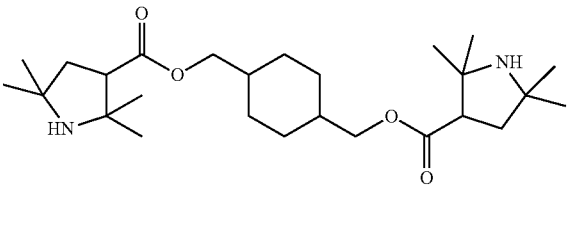
(I-2-32)
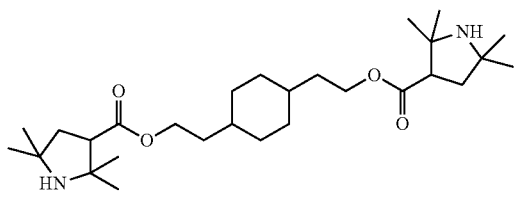
(I-2-33)
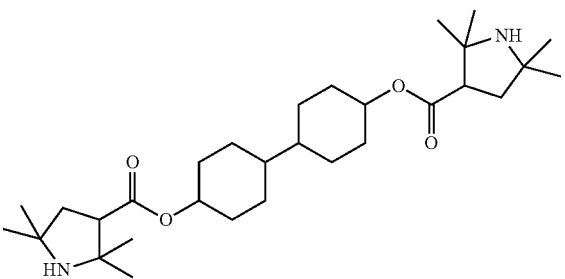
(I-2-34)
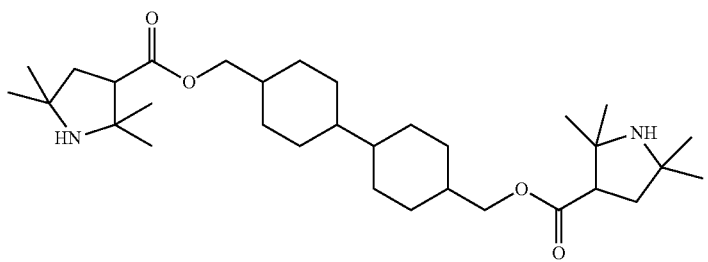

(I-2-35)
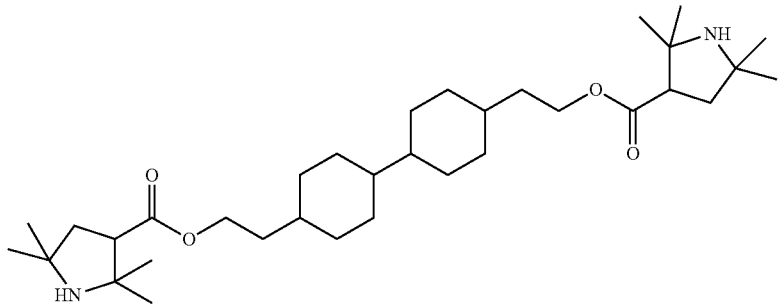
(I-2-36)
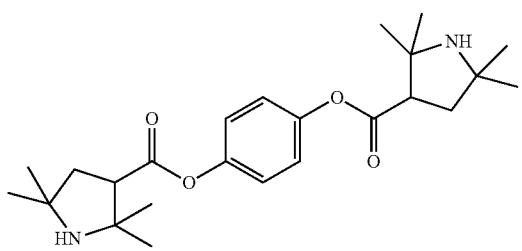
(I-2-37)
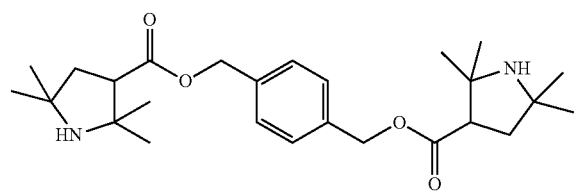
(I-2-38)
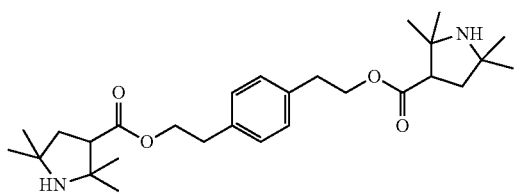
(I-2-39)
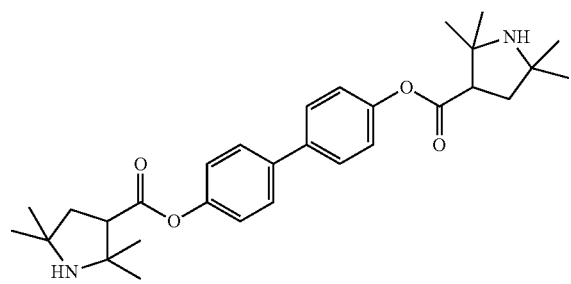
(I-2-40)
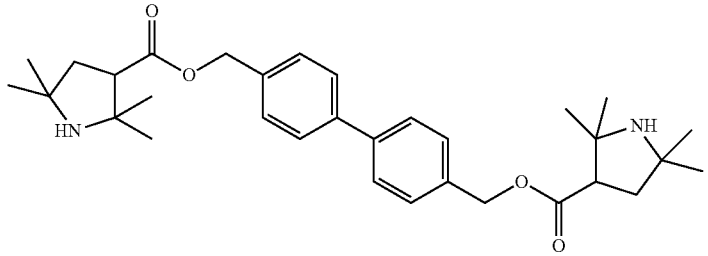
(I-2-41)
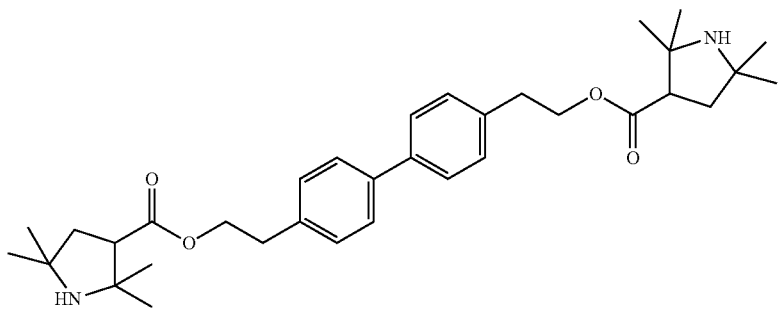

-continued
(I-2-42)
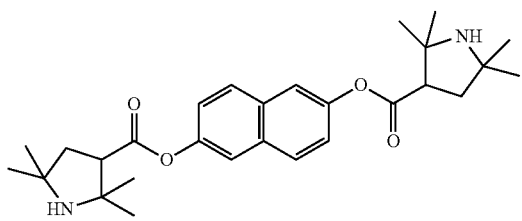
(I-2-43)
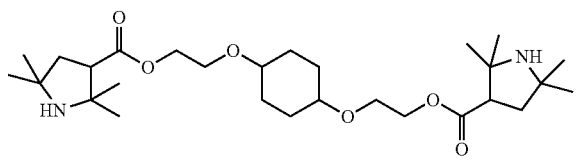
(I-2-44)
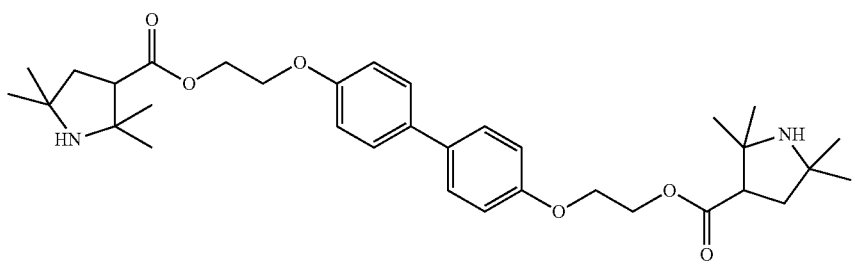
[Chem. 19]
(I-2-45)
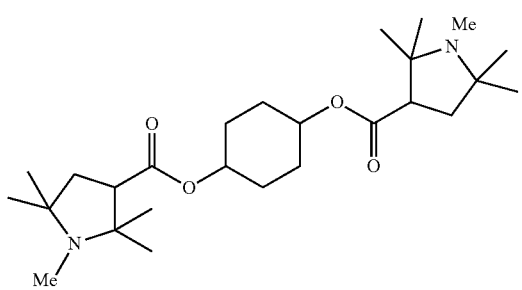
(I-2-46)
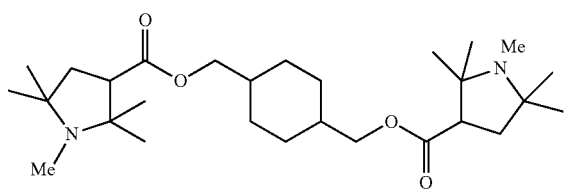
(I-2-47)
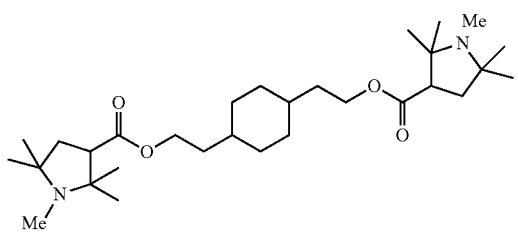
(I-2-48)
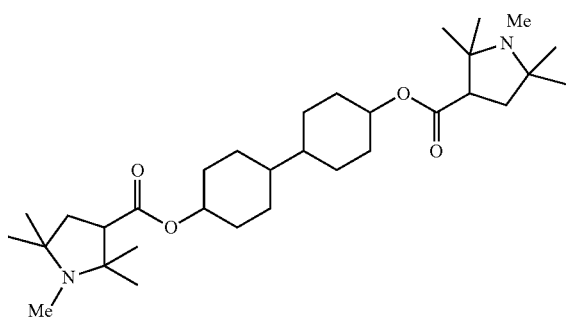
(I-2-49)
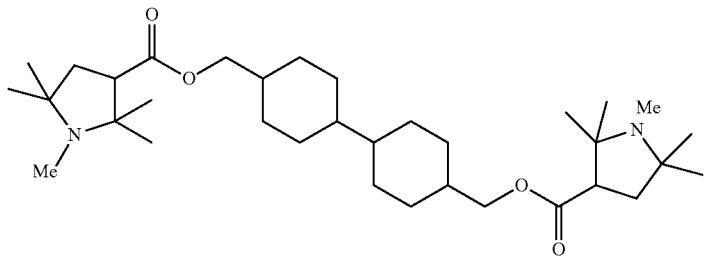

-continued
(I-2-50)
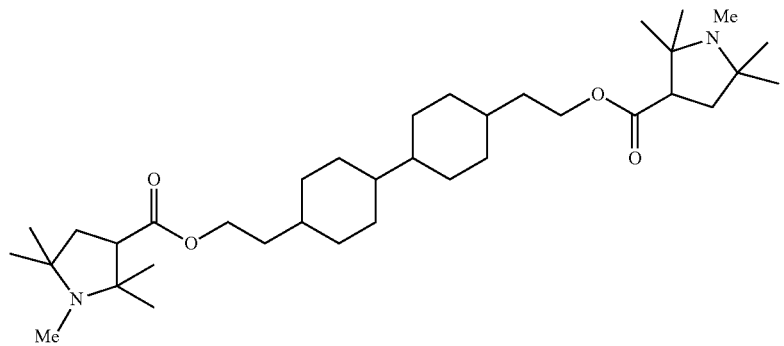
(I-2-51) (I-2-52)
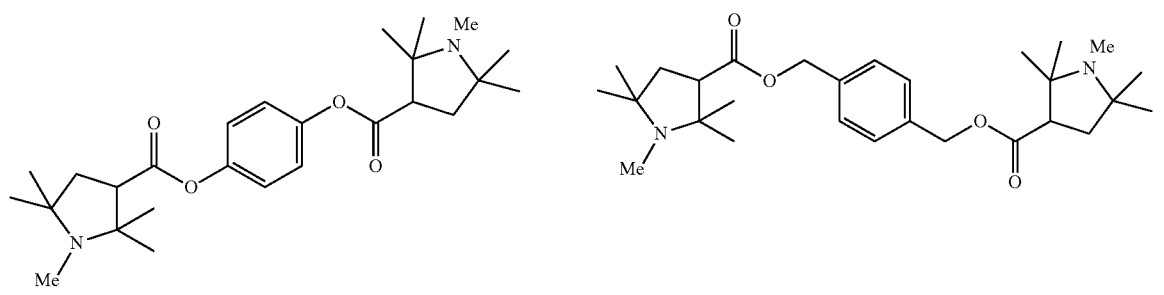
(I-2-53) (I-2-54)
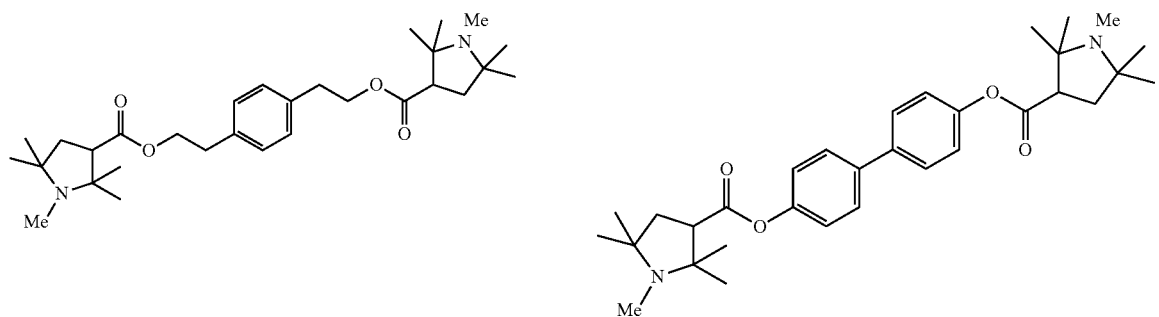
(I-2-55)
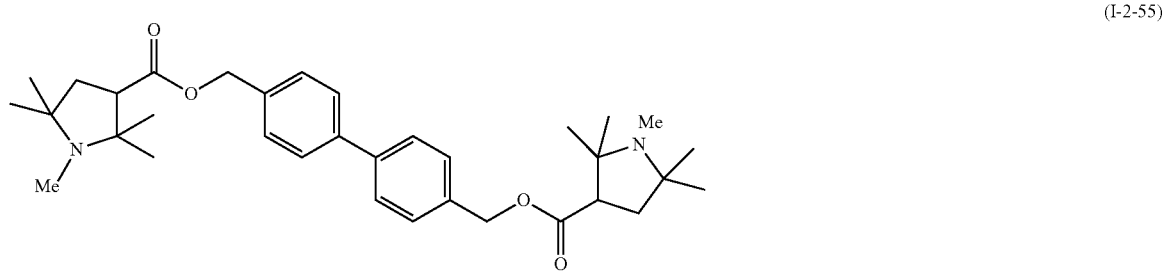
(I-2-56)
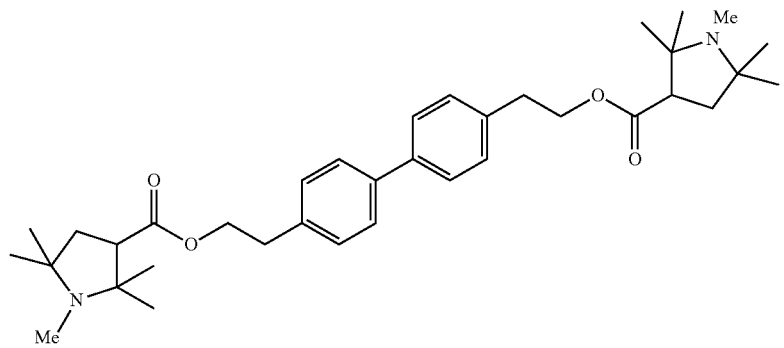

[Chem. 20]
(I-2-57)
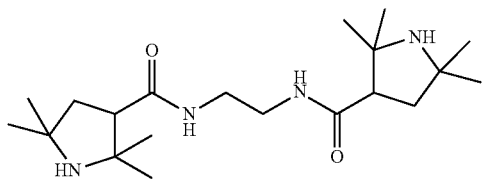
(I-2-58)
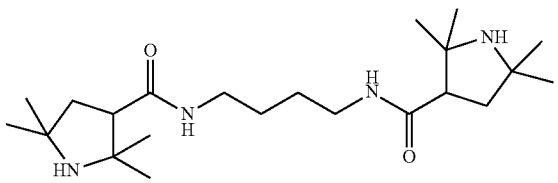
(I-2-59)
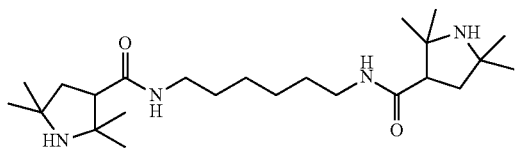
(I-2-60)
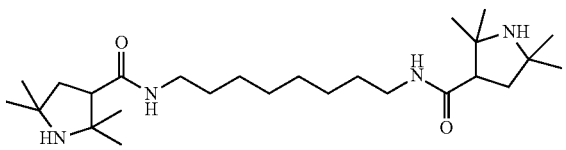
(I-2-61)
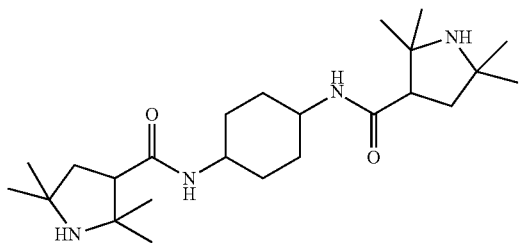
(I-2-62)
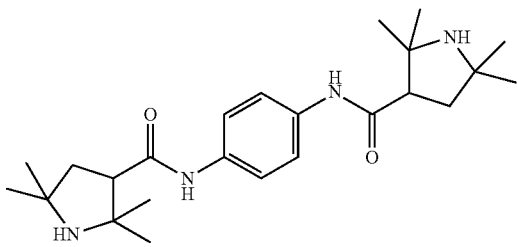
(I-2-63)
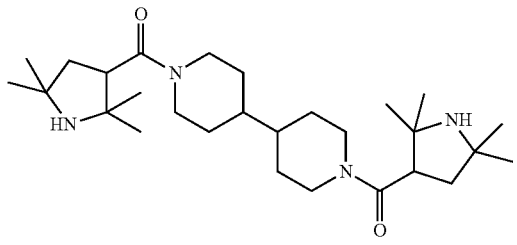
(I-2-64)
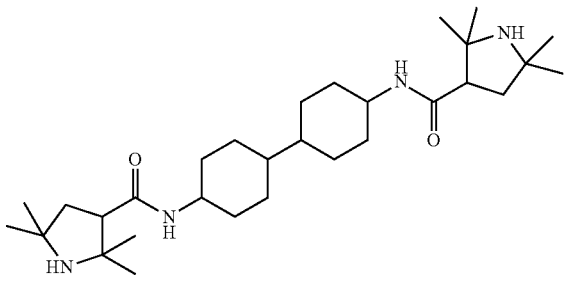
(I-2-65)
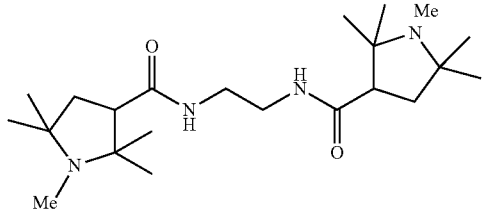
(I-2-66)
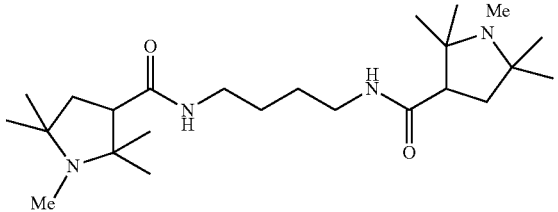
(I-2-67)
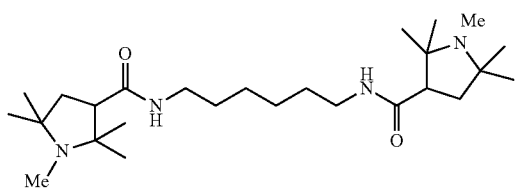
(I-2-68)
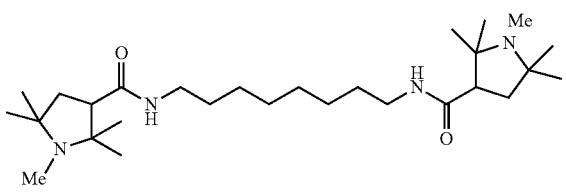

-continued
(I-2-69)
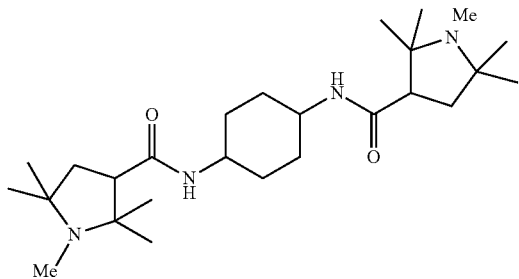
(I-2-70)
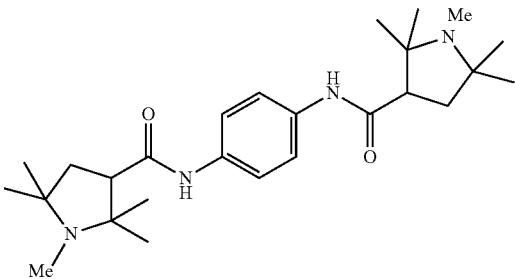
(I-2-71)
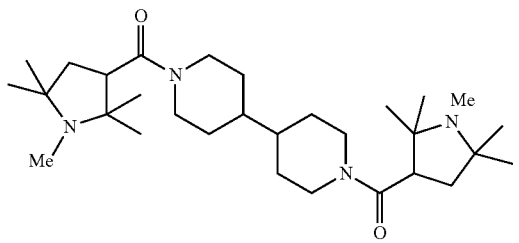
(I-2-72)
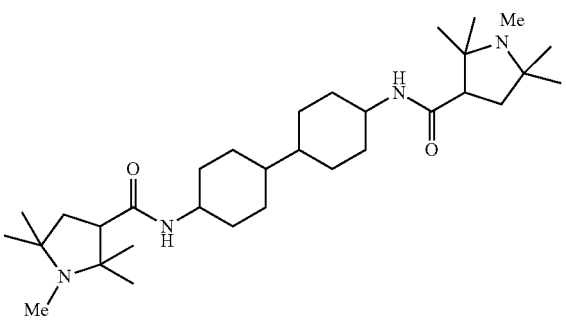
(I-2-73)
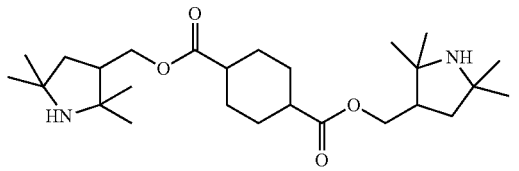
(I-2-74)
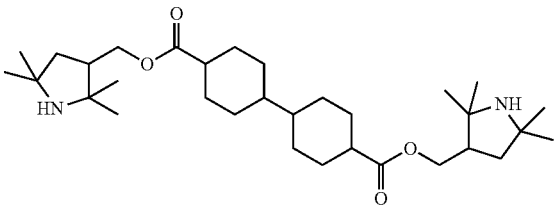
(I-2-75)
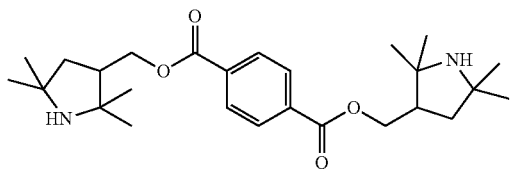
(I-2-76)
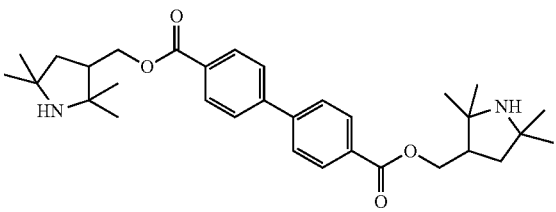
(I-2-77)
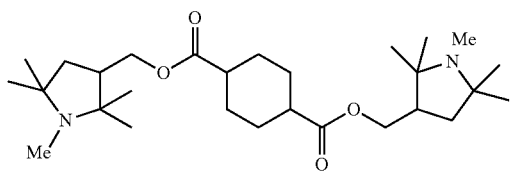
(I-2-78)
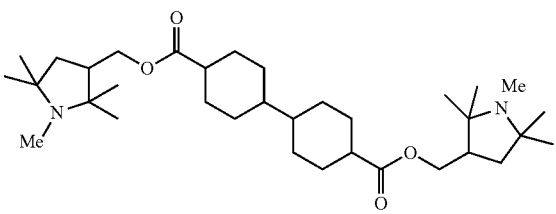
(I-2-79)
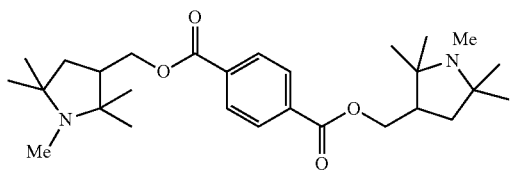
(I-2-80)
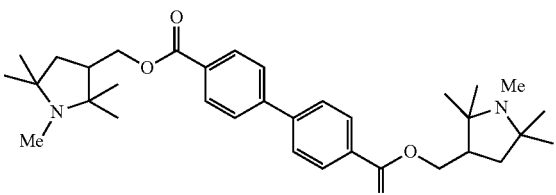

[Chem. 21]
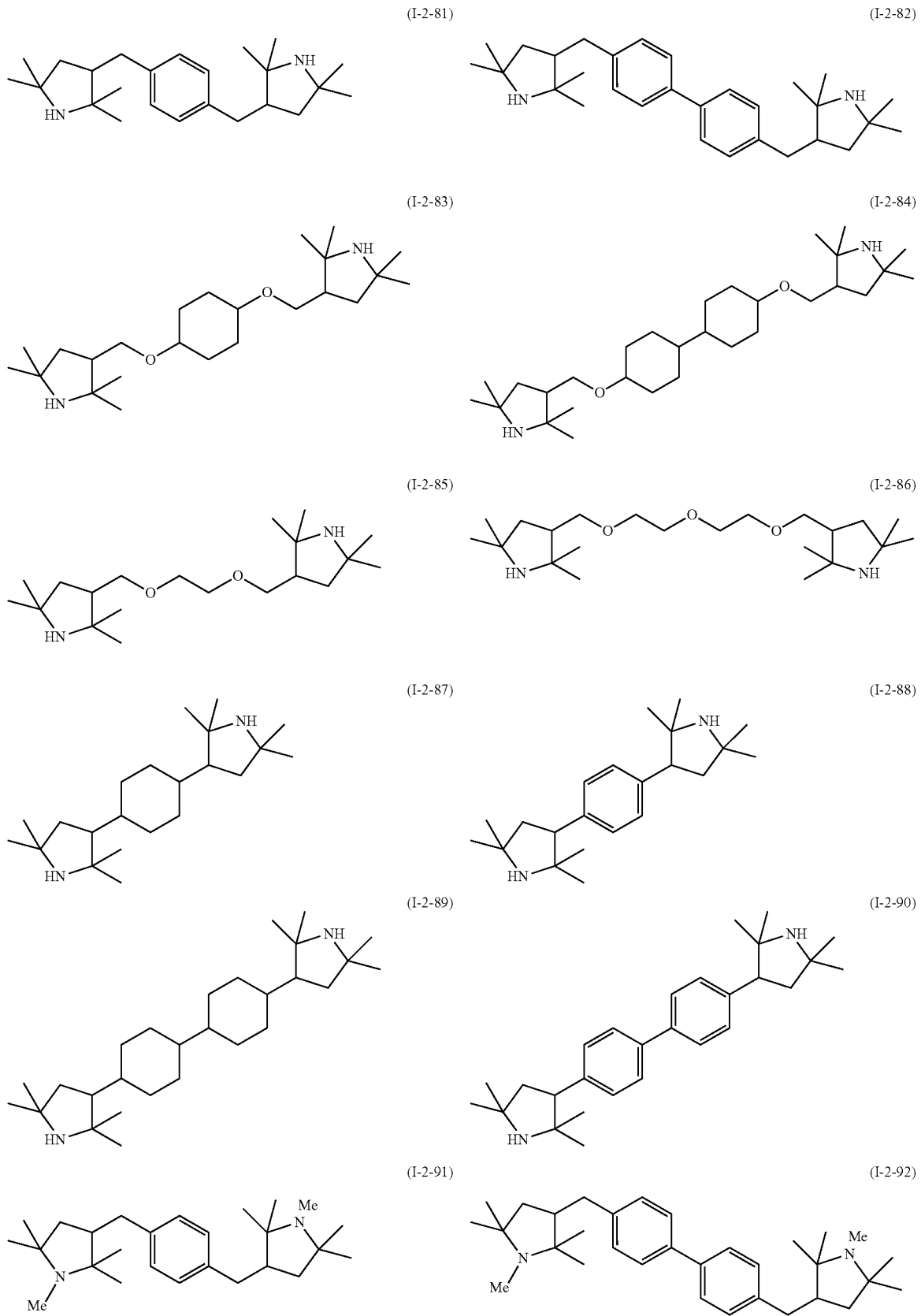

(I-2-93)
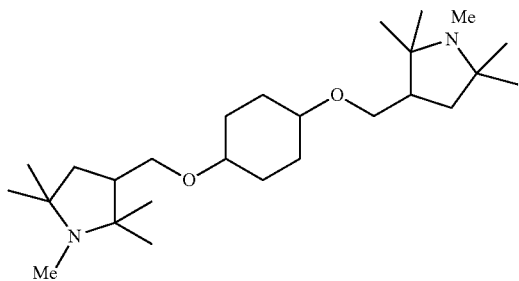
(I-2-94)
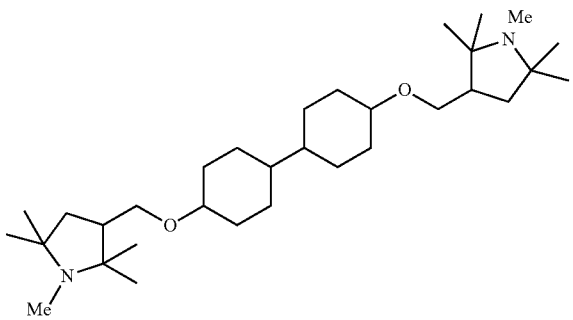
(I-2-95)
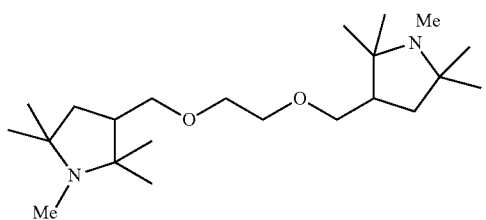
(I-2-96)
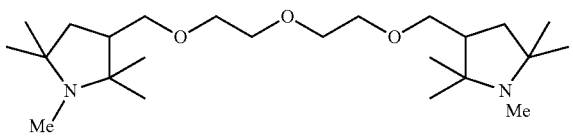
(I-2-97)
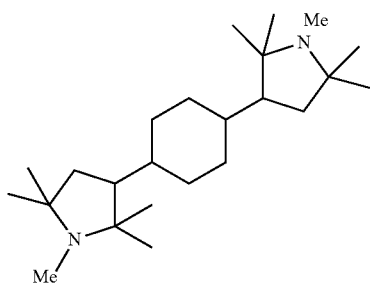
(I-2-98)
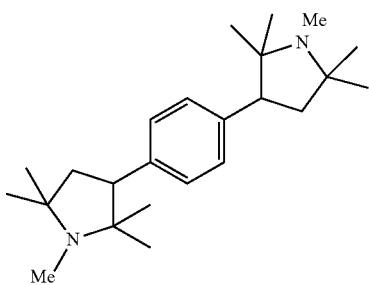
(I-2-99)
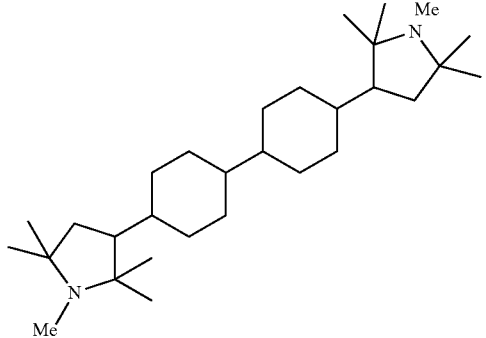
(I-2-100)
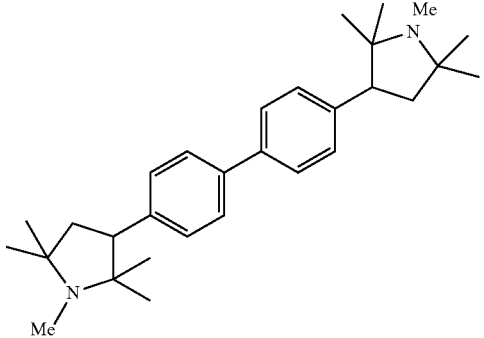
[Chem. 22]
(I-2-101)
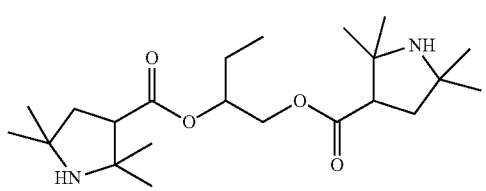
(I-2-102)
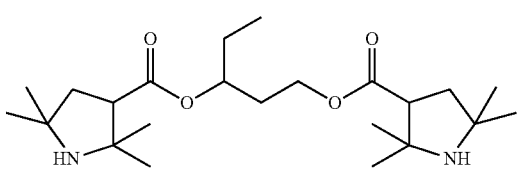

-continued
(I-2-103)
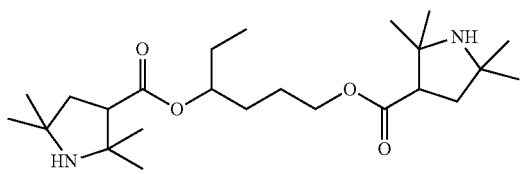
(I-2-104)
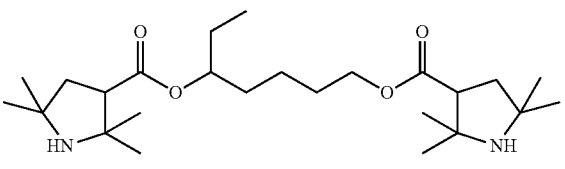
(I-2-105)
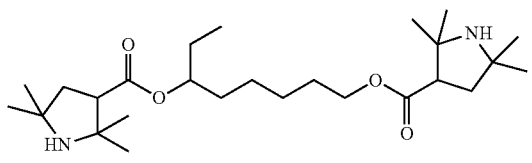
(I-2-106)
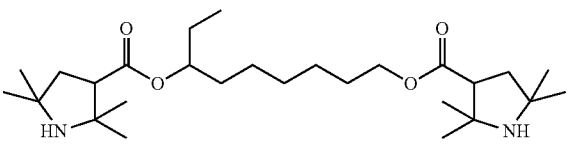
(I-2-107)
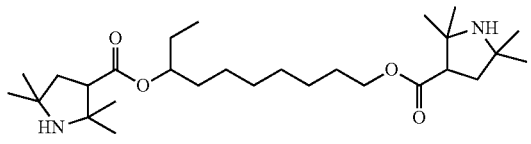
(I-2-108)
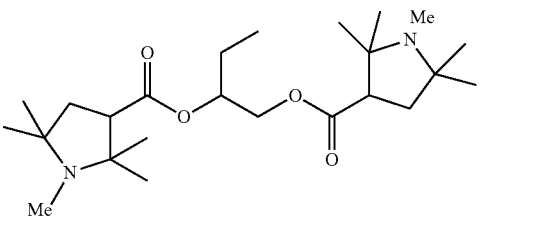
(I-2-109)
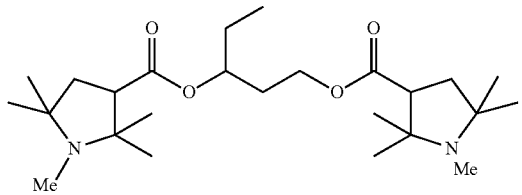
(I-2-110)
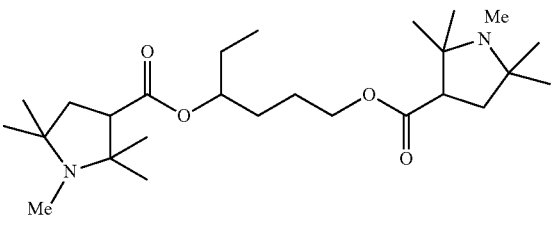
(I-2-111)
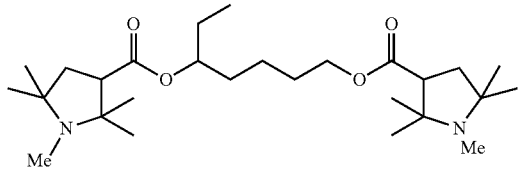
(I-2-113)
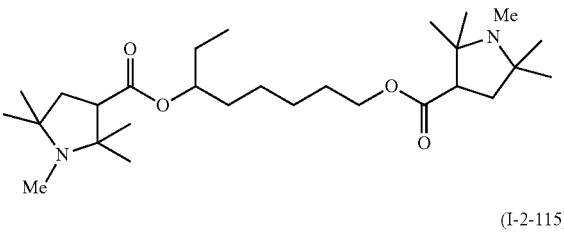
(I-2-114)
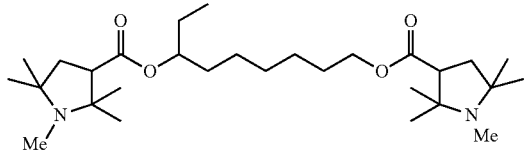
(I-2-115)
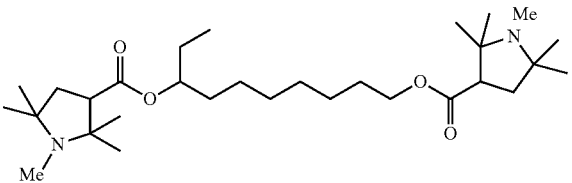
(I-2-116)
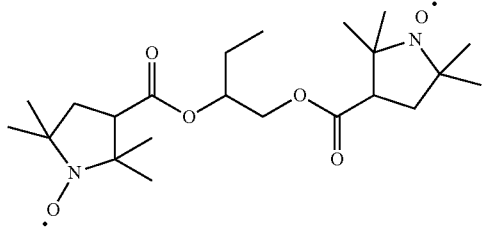
(I-2-117)
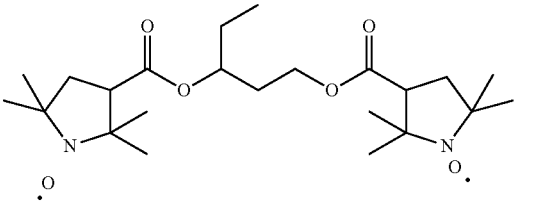

-continued
(I-2-118)
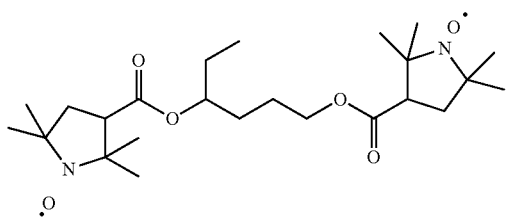
(I-2-119)
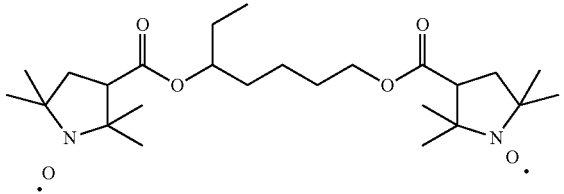
(I-2-120)
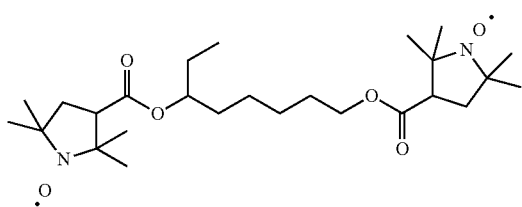
(I-2-121)
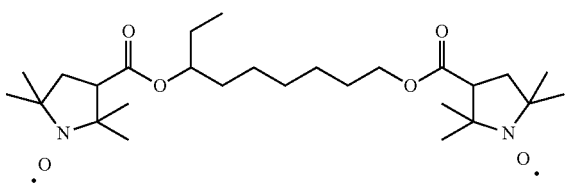
(I-2-122)
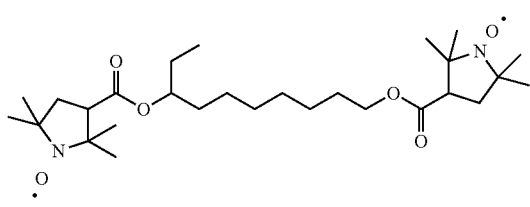
(I-2-123)
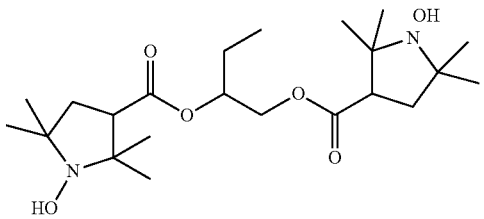
(I-2-124)
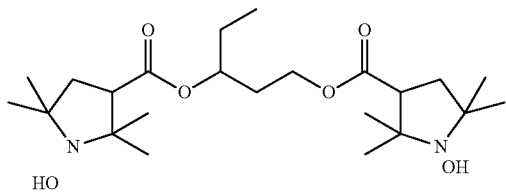
(I-2-125)
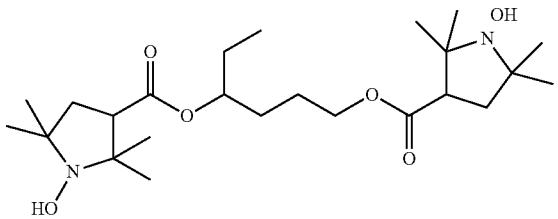
(I-2-126)
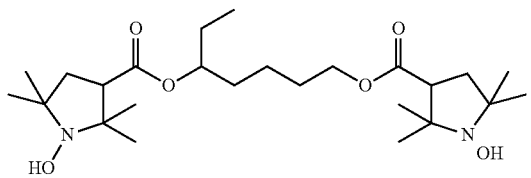
(I-2-127)
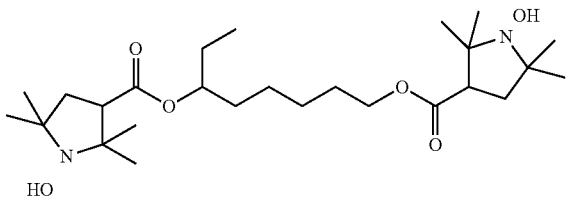
(I-2-128)
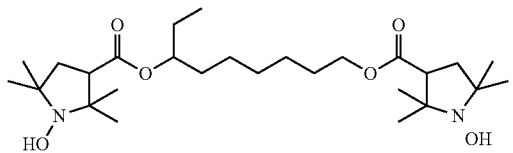
(I-2-129)
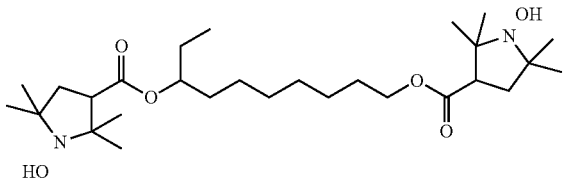

In the formulas, Me represents a methyl group.

In General Formula (I), in the case where n in General Formula (I) represents 3, that is, in the case where nu1 in General Formula (U-1) is 3 and the valency of W is 3, W in General Formula (U-1) preferably represents a hydrocarbon group having 1 to 15 carbon atoms, and one —CH$_2$— or two or more non-adjacent (—CH$_2$—)'s present in the carbon atoms in the hydrocarbon group may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, —OCF$_2$—, —CF$_2$O—, or —C≡C—. W is more preferably a group selected from the group represented by Formula (W3-1) to Formula (W3-12).

[Chem. 23]

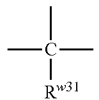
(W3-1)

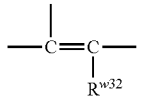
(W3-2)

(W3-3)

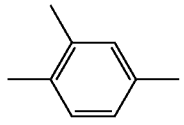
(W3-4)

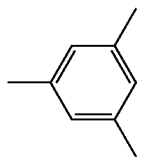
(W3-5)

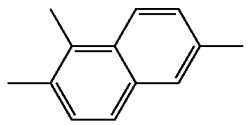
(W3-6)

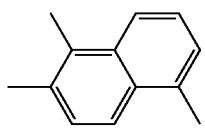
(W3-7)

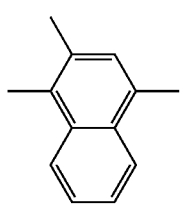
(W3-8)

-continued

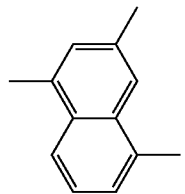
(W3-9)

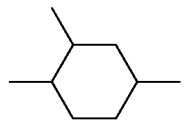
(W3-10)

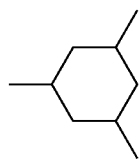
(W3-11)

(W3-12)

In the formulas, R$^{w31}$ and R$^{w32}$ represent a hydrogen atom, a hydroxyl group, or an alkyl group having 1 to 10 carbon atoms, and one —CH$_2$— or two or more (—CH$_2$—)'s present in the alkyl group may each independently be substituted with —O—, —S—, —CH═CH—, —C≡C—, —CO—O—, or —O—CO—. In addition, any arbitrary hydrogen atom in a cyclic structure may be substituted with a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, and one —CH$_2$— or two or more non-adjacent (—CH$_2$—)'s present in the alkyl group may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, CH═CH—, —CF═CF—, —OCF$_2$—, —CF$_2$O—, or —C≡C—.

R$^{w31}$ and R$^{w32}$ preferably represent a hydrogen atom, a hydroxyl group, or an alkyl group having 1 to 8 carbon atoms, and are preferably linear. In addition, Formulas (W3-4) to (W3-12) are preferably each independently unsubstituted, or the hydrogen atoms in Formulas (W3-4) to (W3-12) may be substituted with a cyano group, a fluorine atom, a chlorine atom, a methyl group, or a methoxy group.

From the viewpoint of ease of availability of raw materials and ease of production, R$^{w31}$ and R$^{w32}$ particularly preferably represent a group selected from Formula (W3-1), Formula (W 3-2), and unsubstituted Formulas (W3-3) to (W3-12).

Specifically, as the compound in which n represents 3 in General Formula (I), compounds represented by Formula (I-3-1) to Formula (I-3-69) are preferable.

[Chem. 24]
(I-3-1)
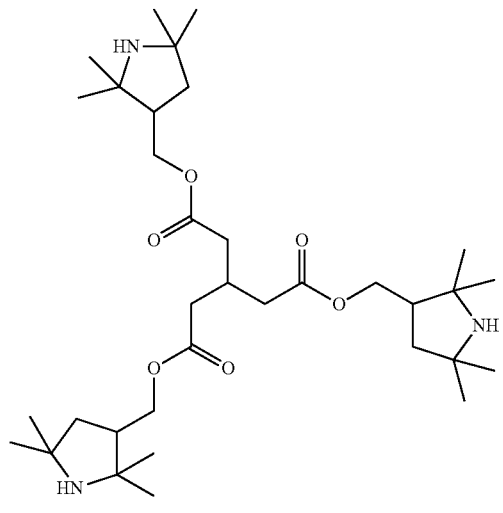
(I-3-2)
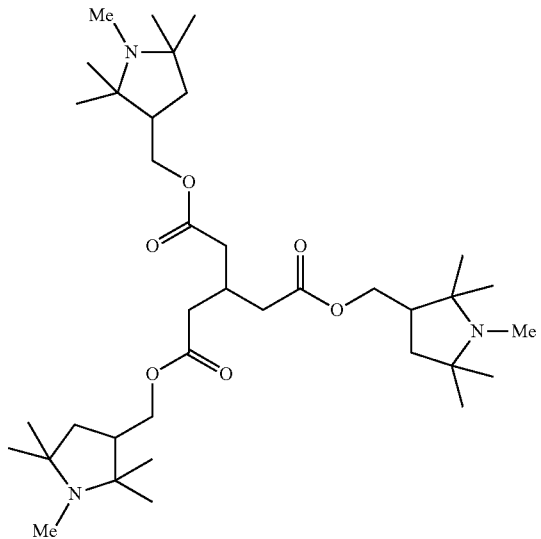
(I-3-3)
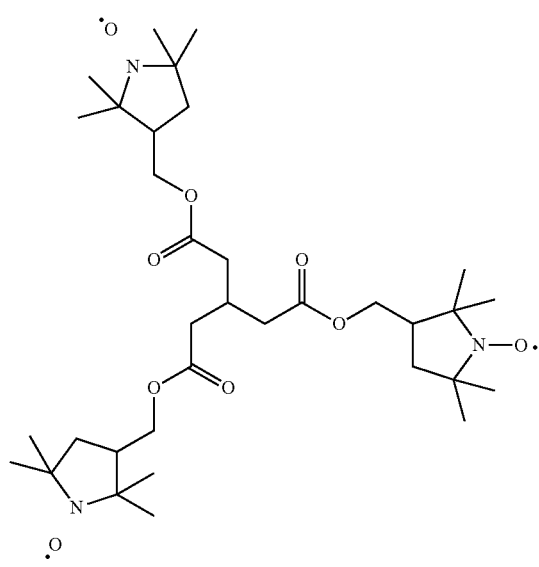
(I-3-4)
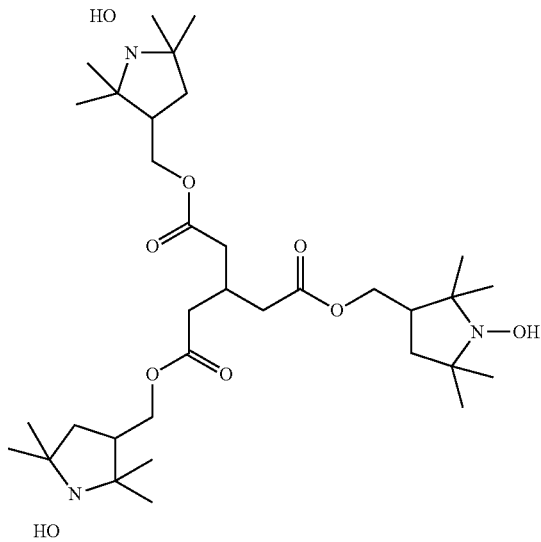

-continued
(I-3-5)
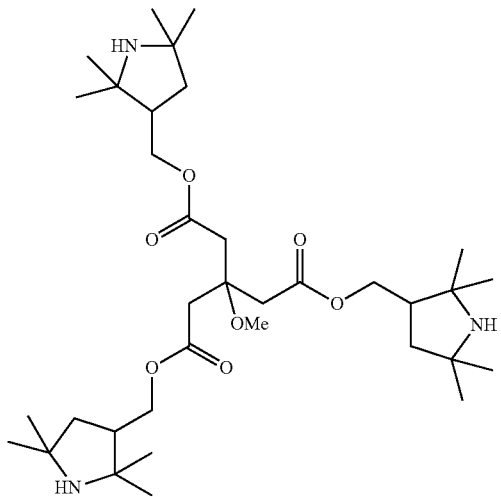
(I-3-6)
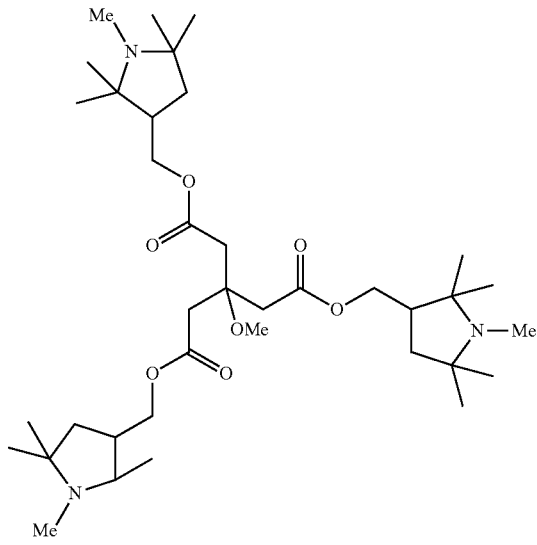
(I-3-7)
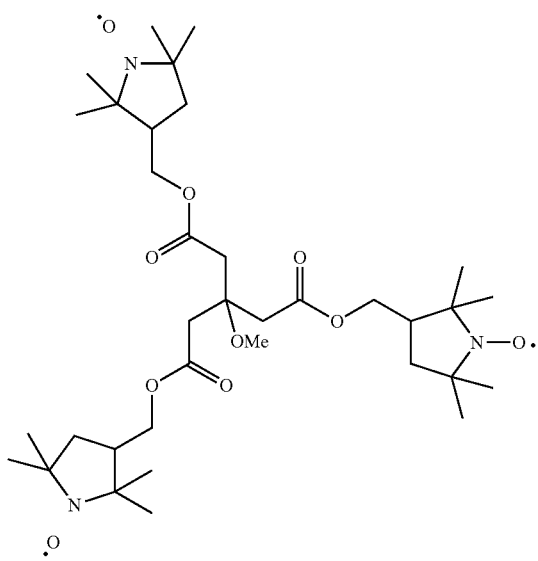
(I-3-8)
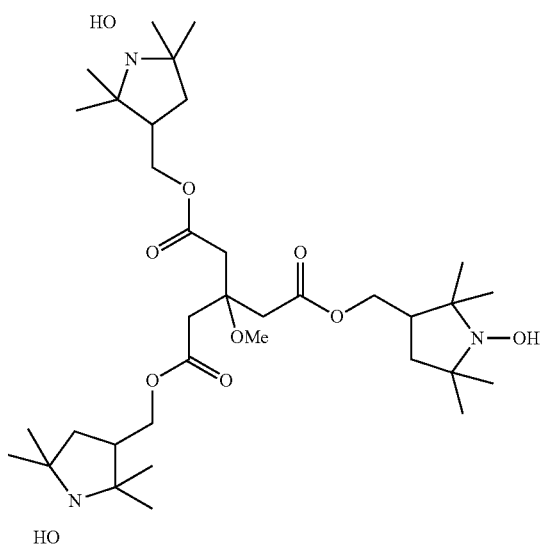
(I-3-9)
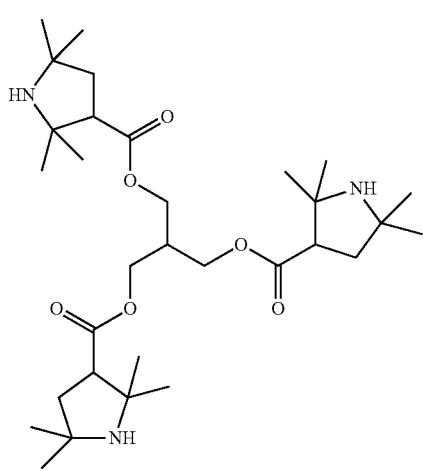
(I-3-10)
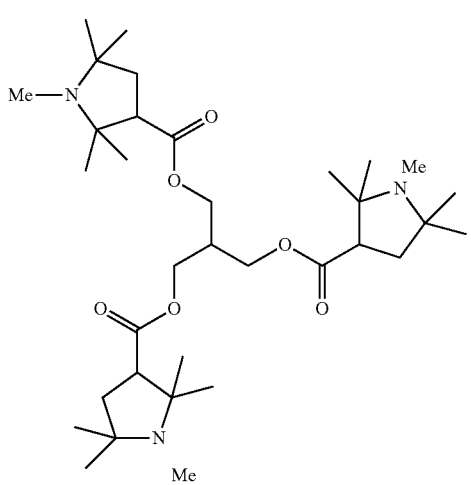

-continued
(I-3-11)
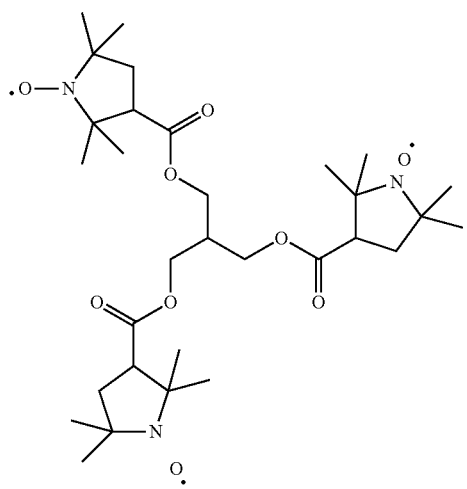
(I-3-12)
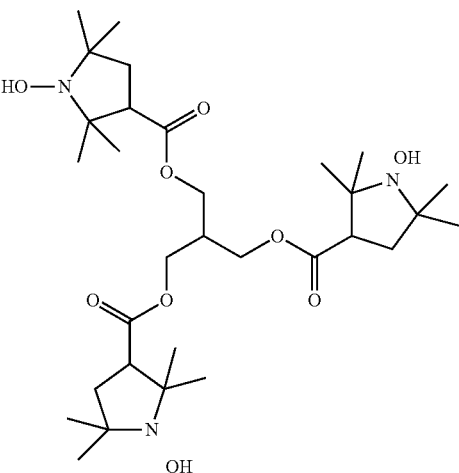
(I-3-13)
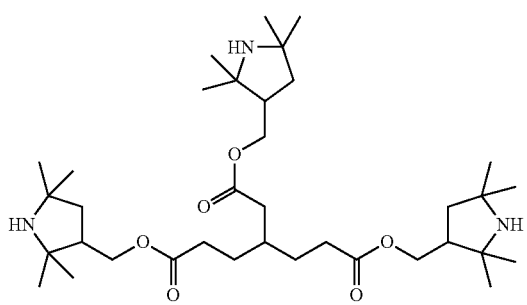
(I-3-14)
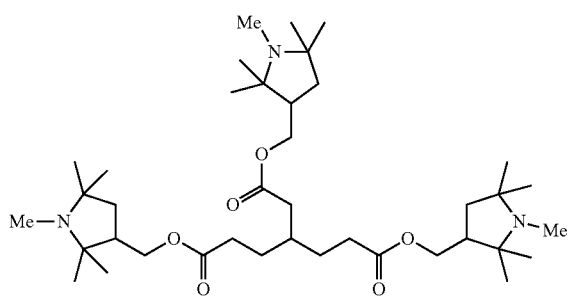
(I-3-15)
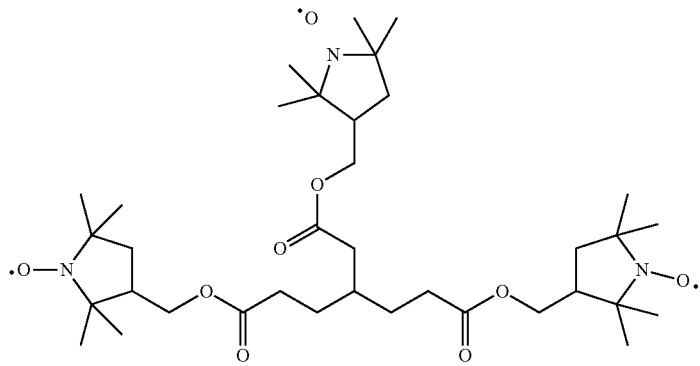
[Chem. 25]
(I-3-16)
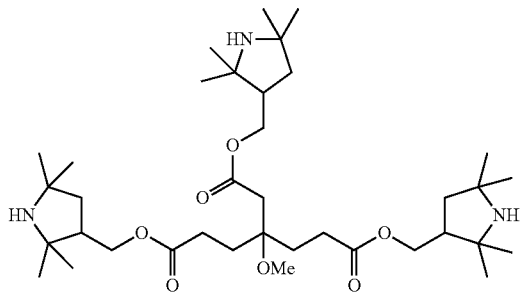
(I-3-17)
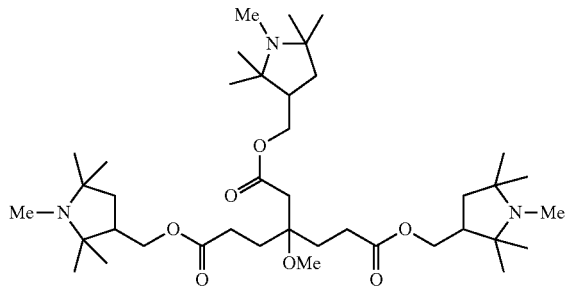

-continued
(I-3-18)
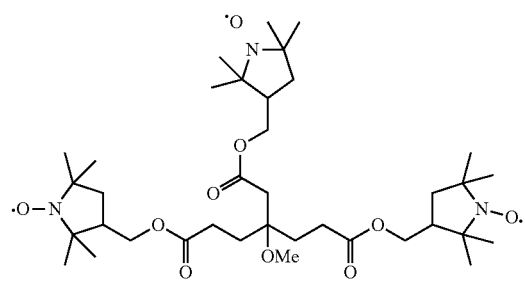
(I-3-19)
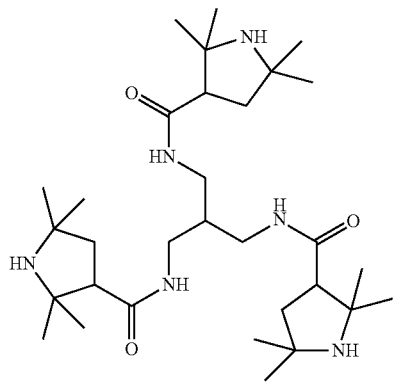
(I-3-20)
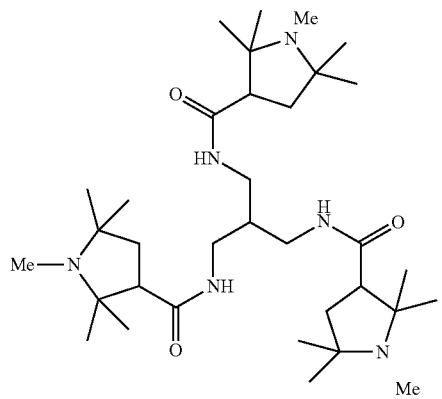
(I-3-21)
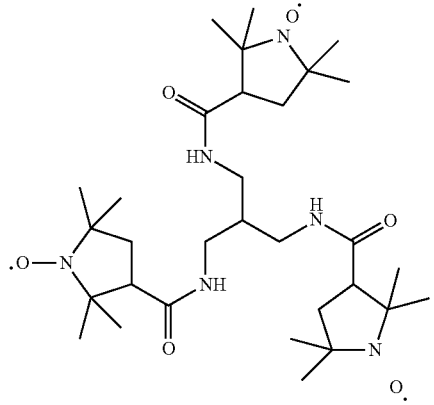
(I-3-22)
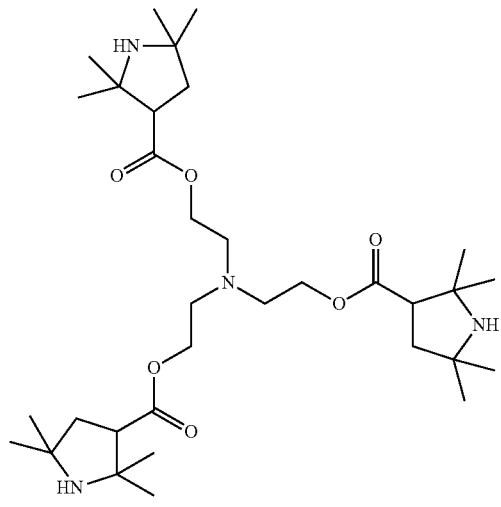
(I-3-23)
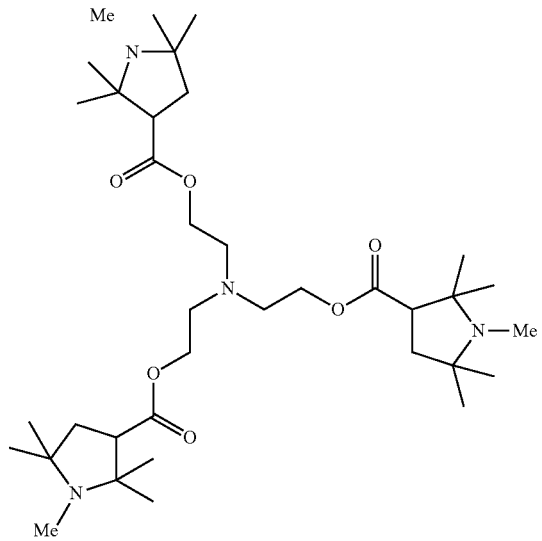

-continued
(I-3-24)
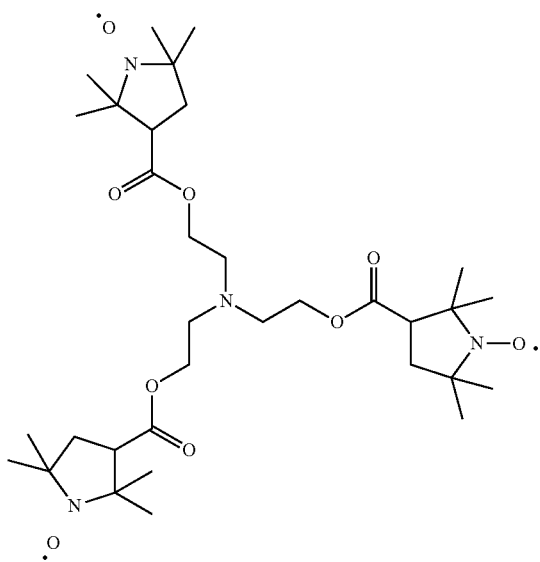
(I-3-25)
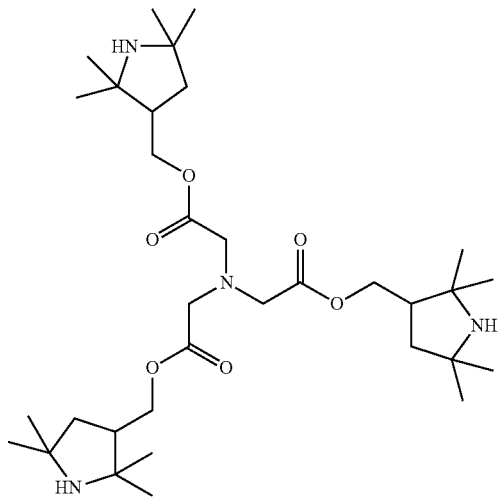
(I-3-26)
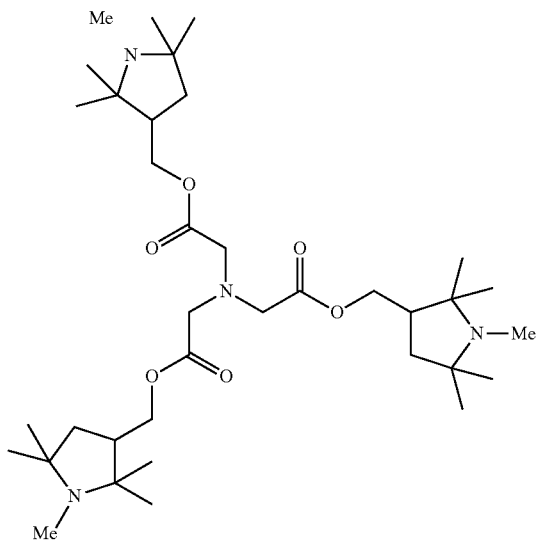
(I-3-27)
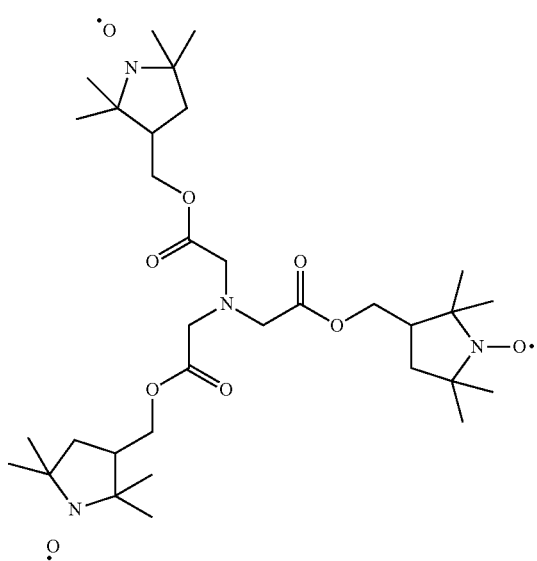

(I-3-28)
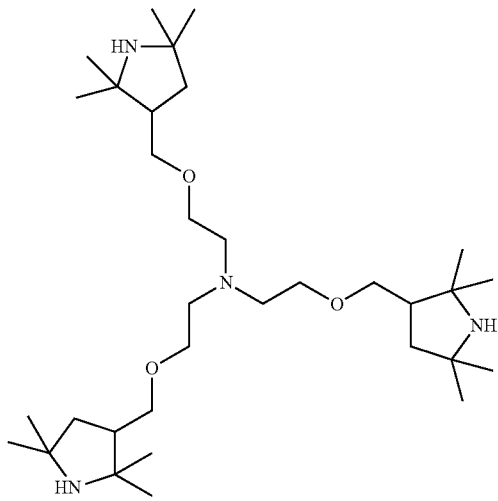
(I-3-29)
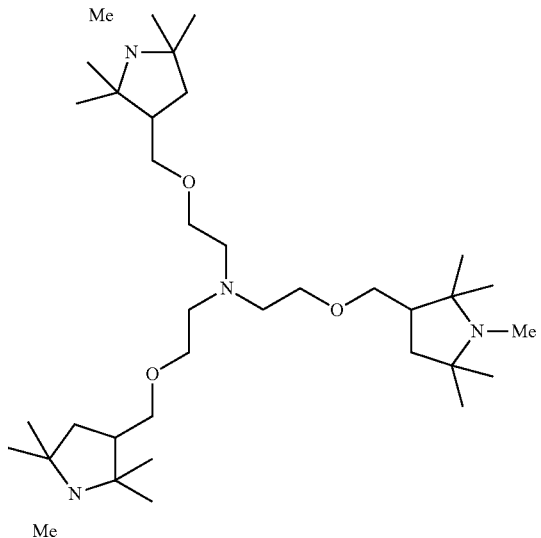
(I-3-30)
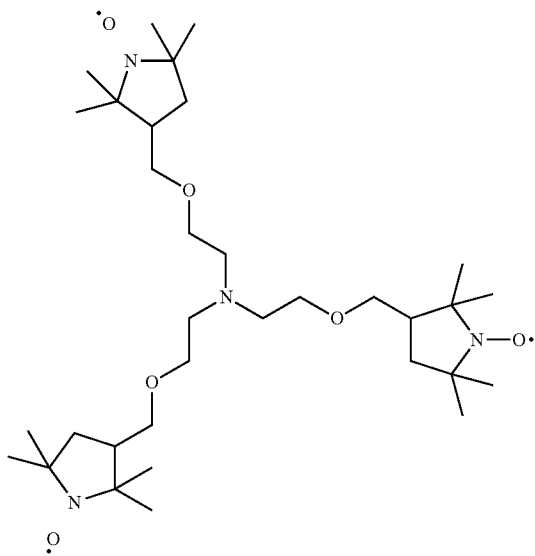

[Chem. 26]
(I-3-31)
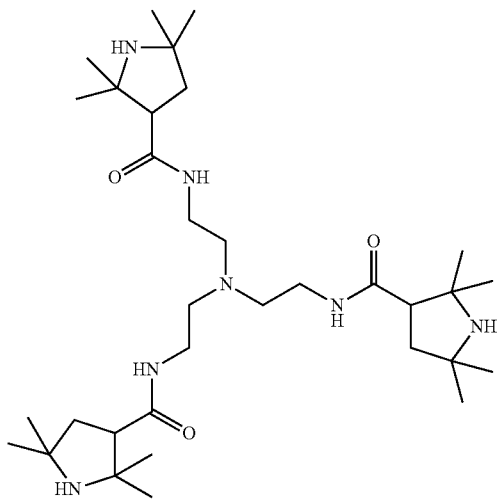
(I-3-32)
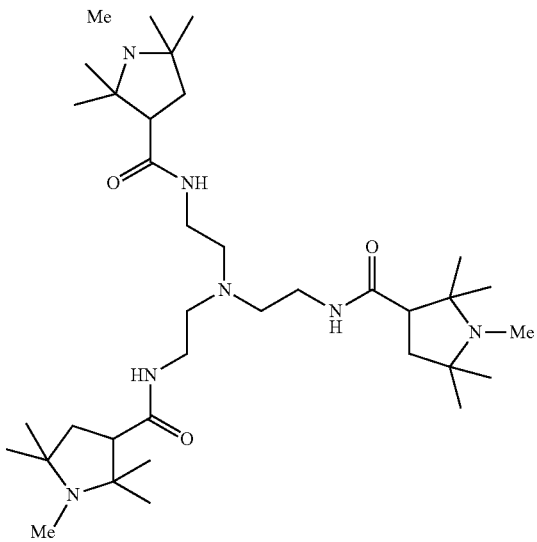
(I-3-33)
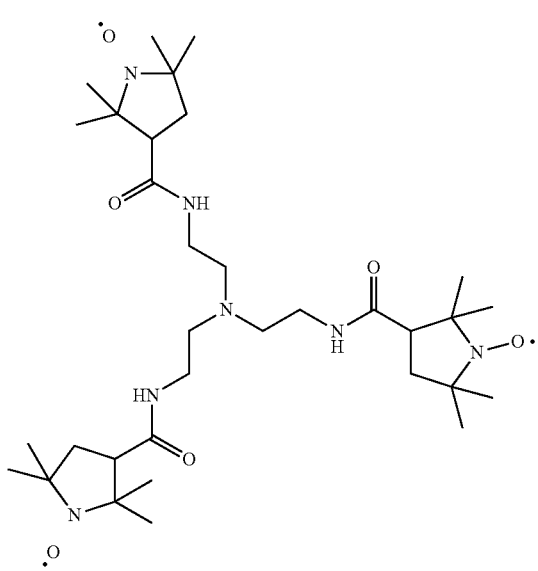
(I-3-34)
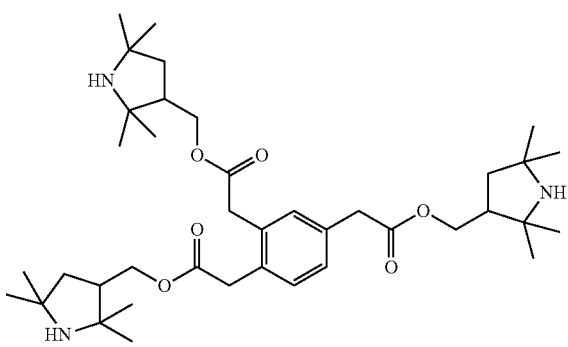
(I-3-35)
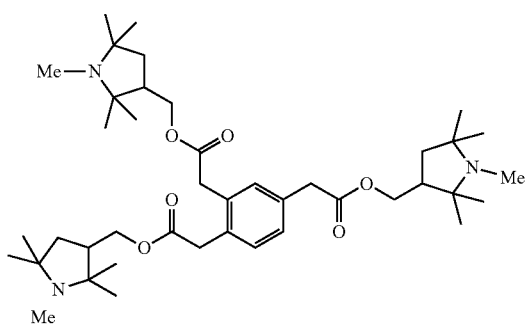
(I-3-36)
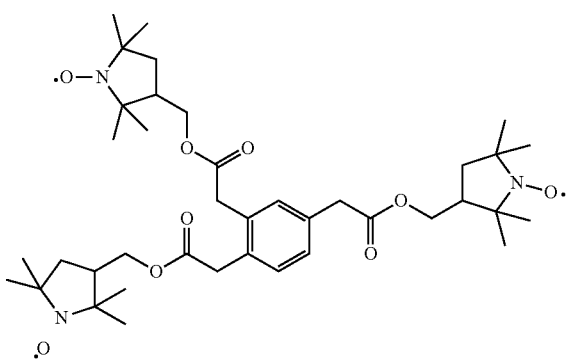

(I-3-37)
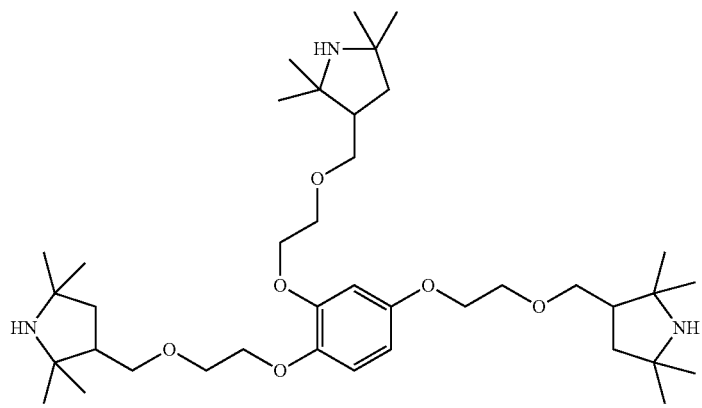
(I-3-38)
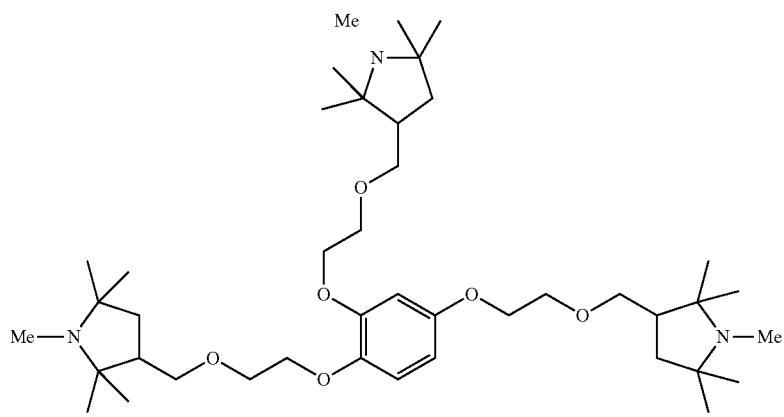
(I-3-39)
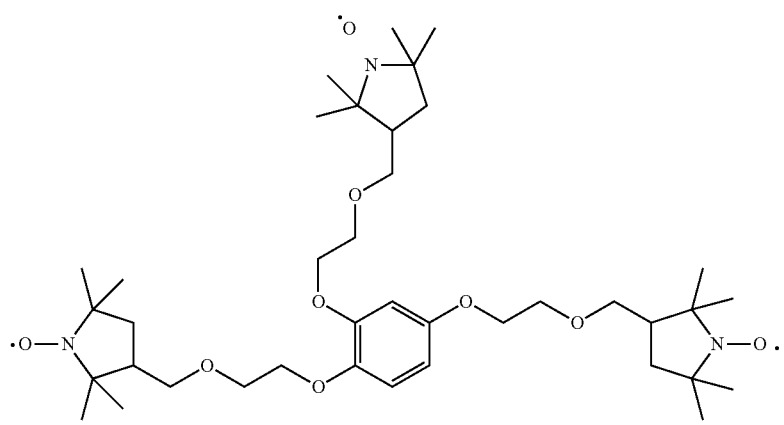

-continued
(I-3-40)
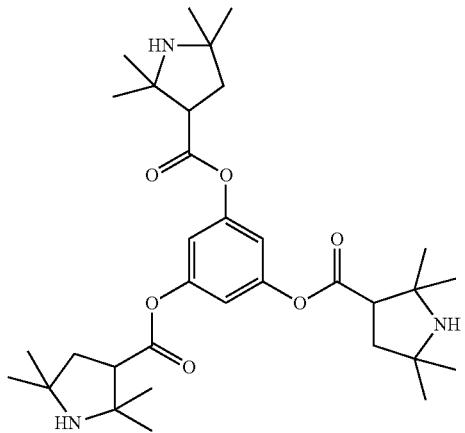
(I-3-41)
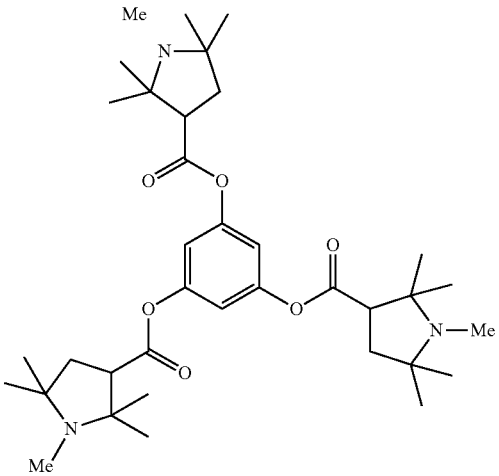
(I-3-42)
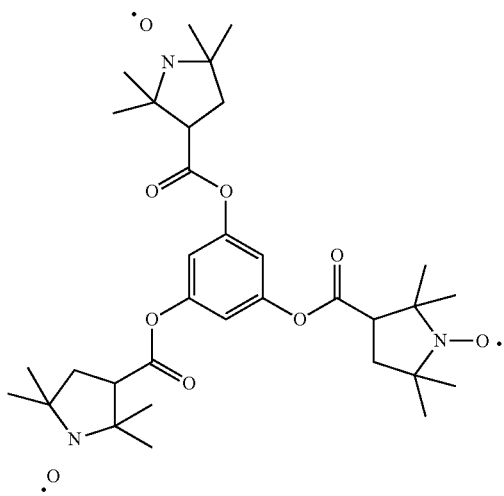
(I-3-43)
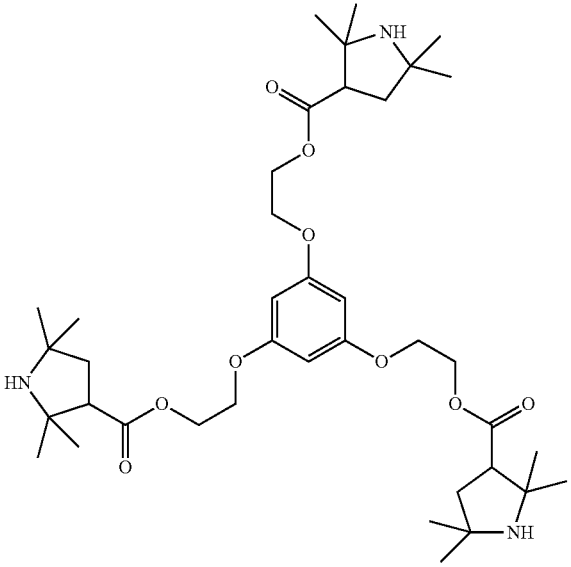
(I-3-44)
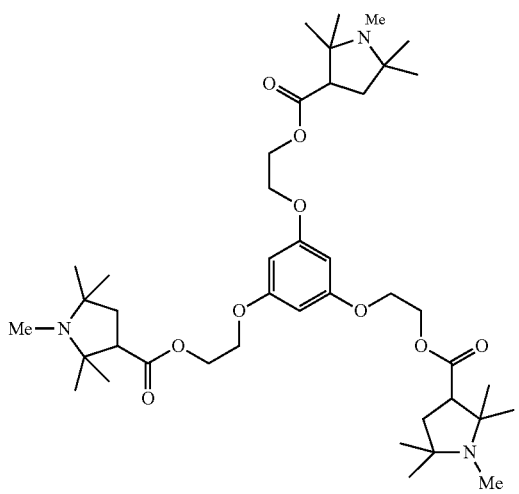
(I-3-45)
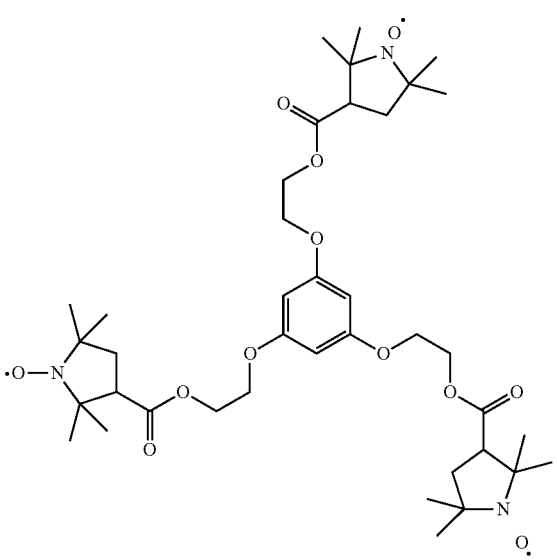

[Chem. 27]
(I-3-46)
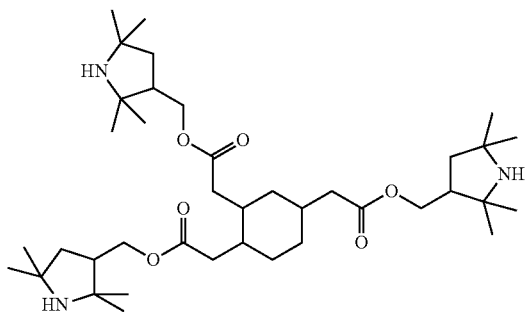
(I-3-47)
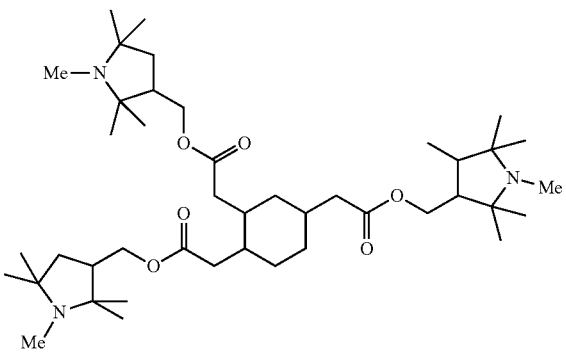
(I-3-48)
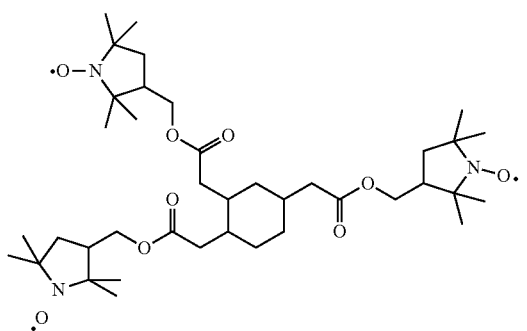
(I-3-49)
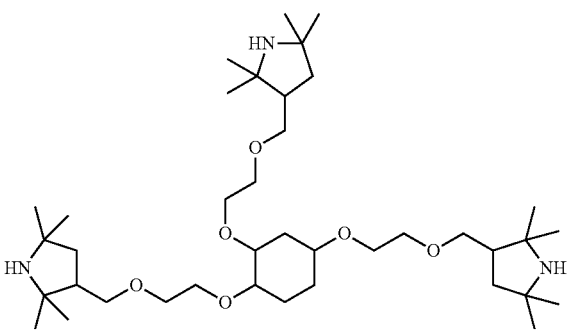
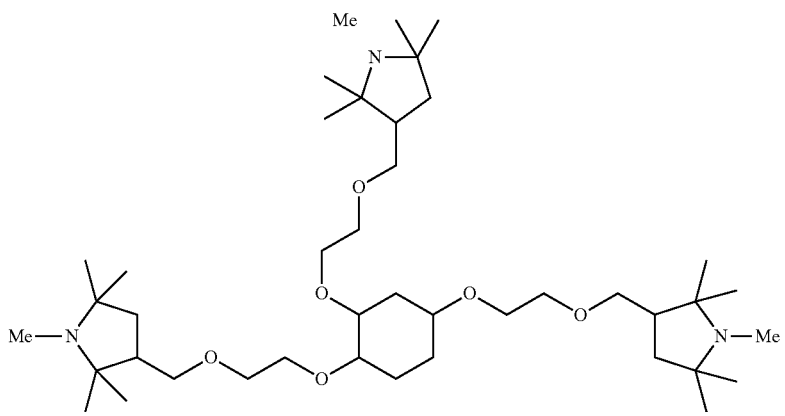
(I-3-50)
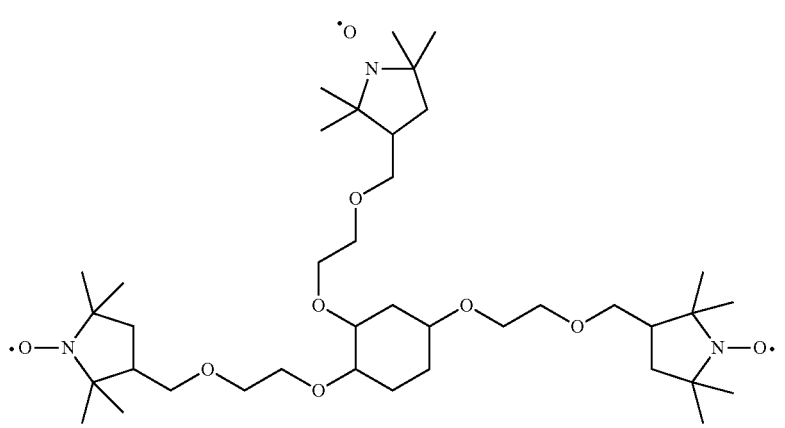
(I-3-51)

-continued
(I-3-52)
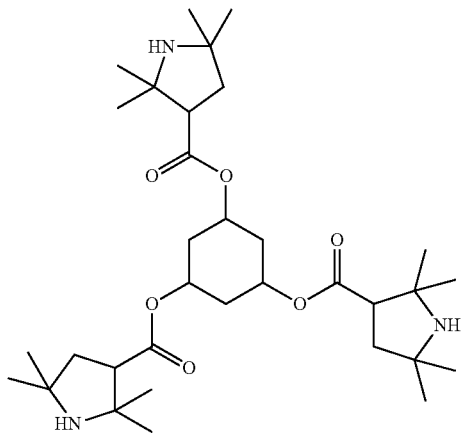
(I-3-53)
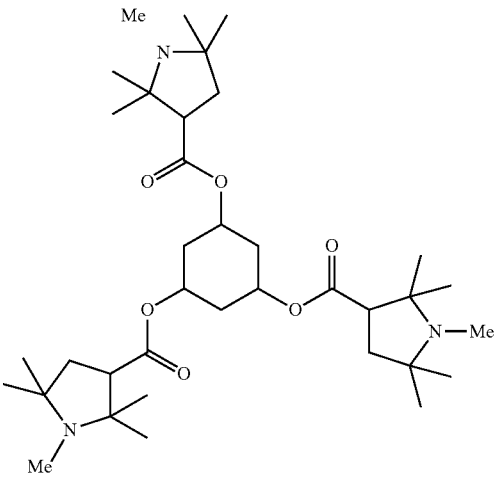
(I-3-54)
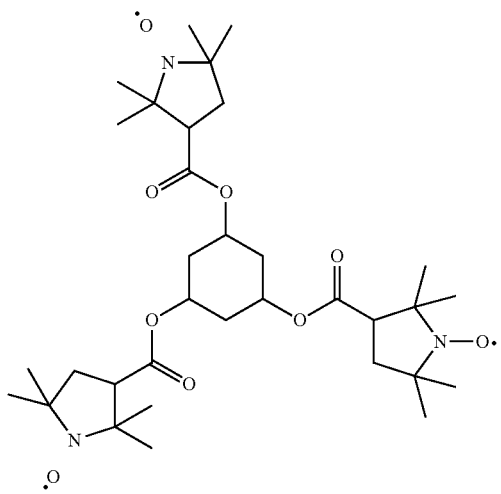
(I-3-55)
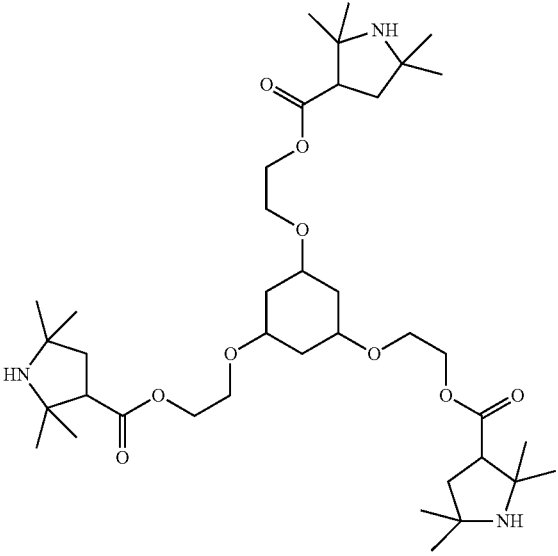
(I-3-56)
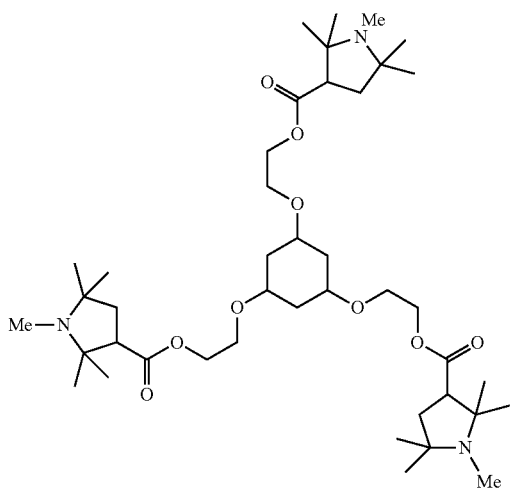
(I-3-57)
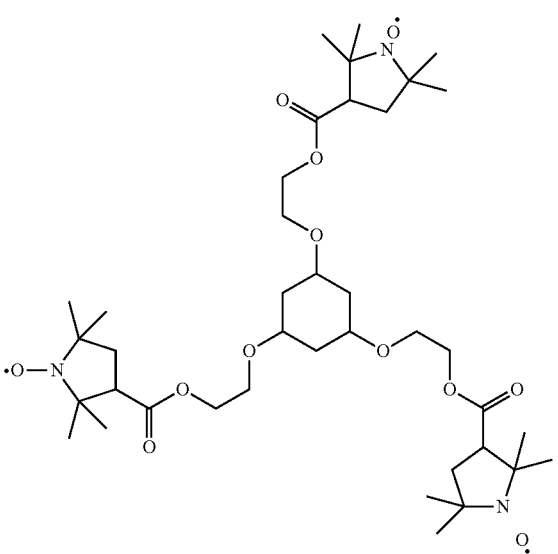

(I-3-58)
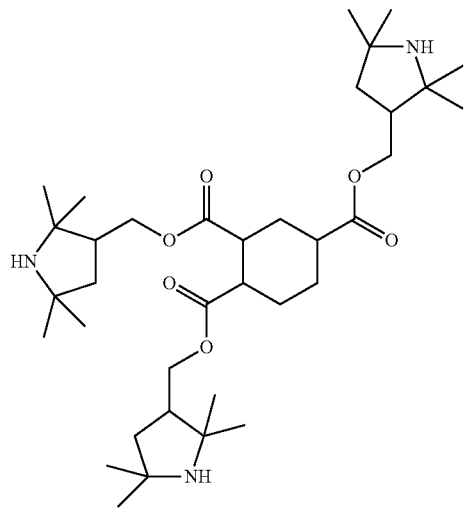
(I-3-59)
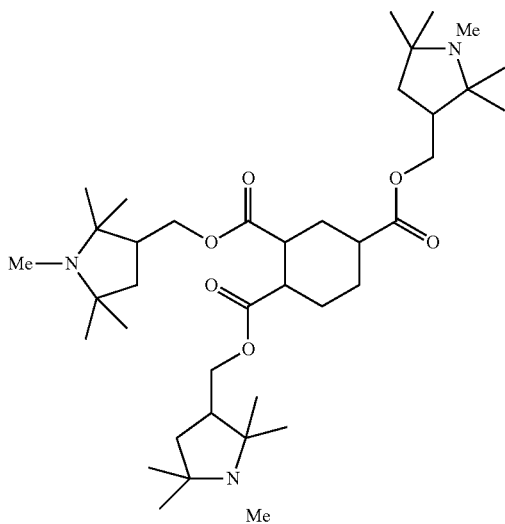
(I-3-60)
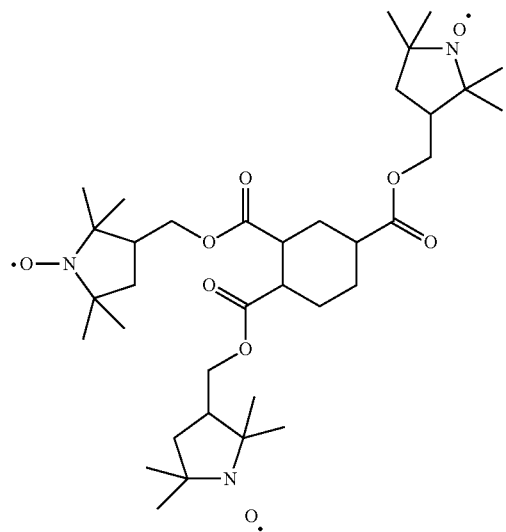
[Chem. 28]
(I-3-61)
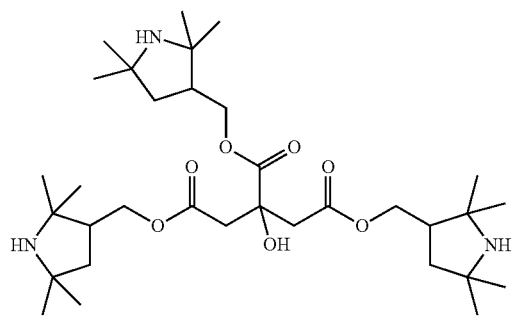
(I-3-62)
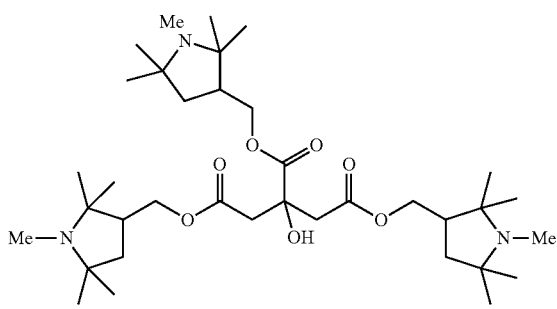

(I-3-63)
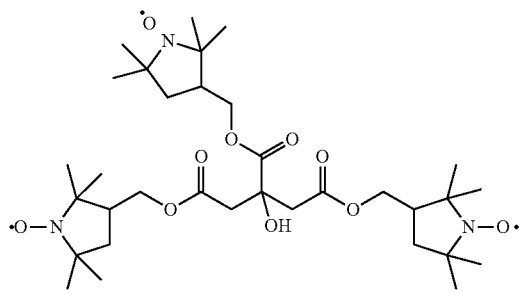

(I-3-64)
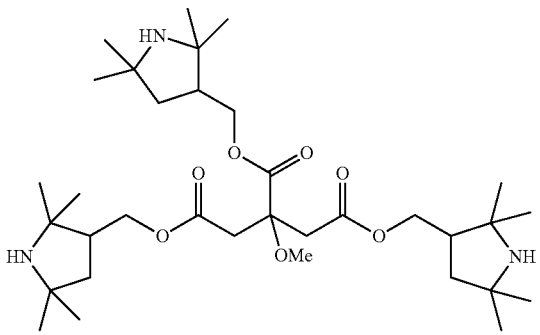

(I-3-65)
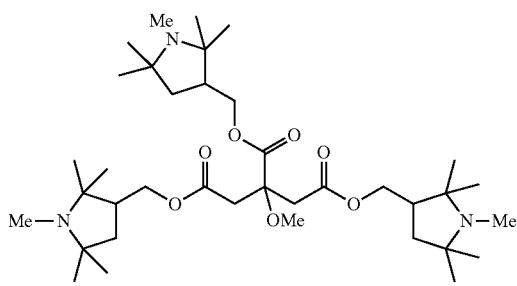

(I-3-66)
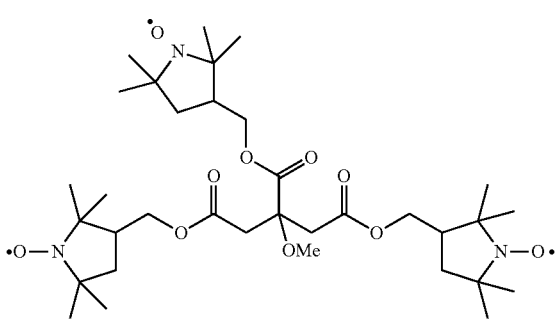

(I-3-67)
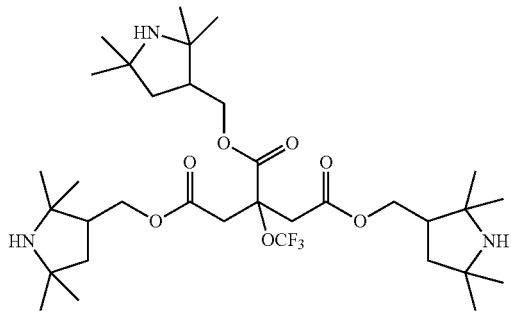

(I-3-68)

(I-3-69)
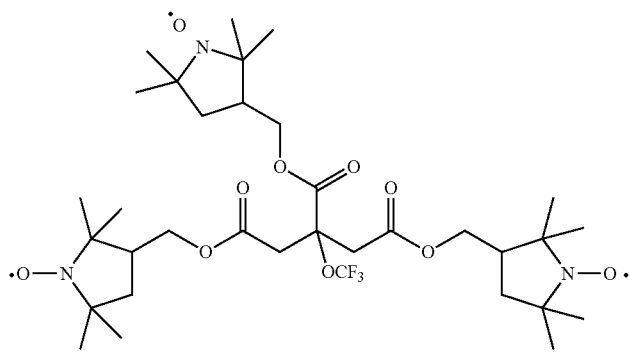

In the formulas, Me represents a methyl group.

In General Formula (I), in the case where n in General Formula (I) represents 4, that is, in the case where nu1 in General Formula (U-1) is 4 and the valency of W is 4, W in General Formula (U-1) preferably represents a hydrocarbon group having 1 to 15 carbon atoms, and one —$CH_2$— or two or more non-adjacent (—$CH_2$—)'s present in the carbon atoms in the hydrocarbon group may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —$OCF_2$—, —$CF_2O$—, or —C≡C—. W is more preferably a group selected from the groups represented by Formula (W4-1) to Formula (W4-21).

[Chem. 29]
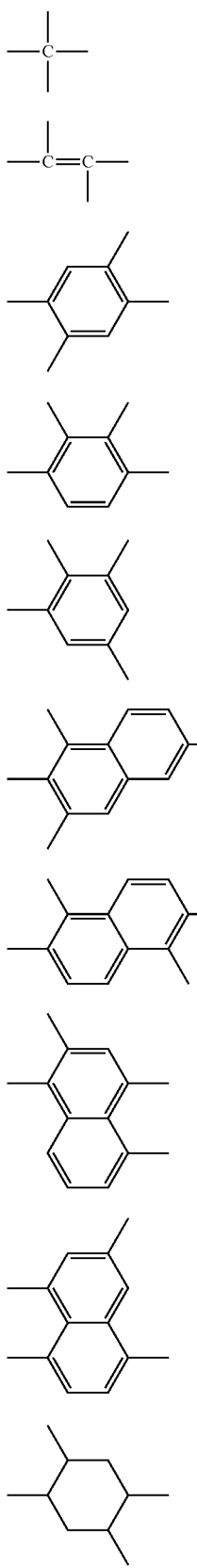
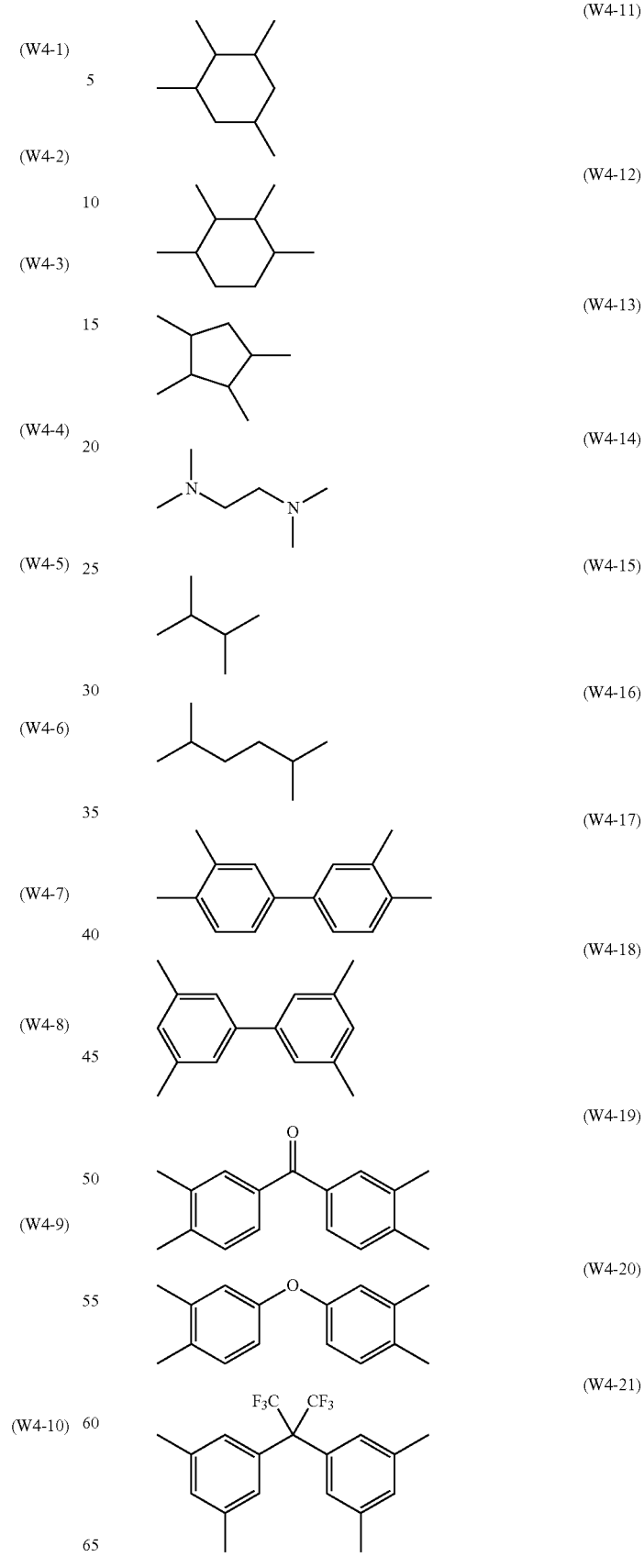

Any arbitrary hydrogen atom in the cyclic structure may be substituted with a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, and one —$CH_2$— or two or more non-adjacent (—$CH_2$—)'s present in the alkyl group may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —$OCF_2$—, —$CF_2O$—, or —C≡C—. In addition, Formula (W4-3) to Formula (W4-21) are preferably each independently unsubstituted, and the hydrogen atoms in Formula (W4-3) to Formula (W4-21) may be substituted with a cyano group, a fluorine atom, a chlorine atom, a methyl group, or a methoxy group.

From the viewpoints of ease of availability of raw materials and ease of production, the group particularly preferably represents a group selected from Formula (W4-1), Formula (W4-2), and the unsubstituted Formulas (W-3) to (W-21).

Specifically, as a compound in which n in General Formula (I) represents 4, the compounds represented by Formula (I-4-1) to Formula (I-4-95) are preferable.

[Chem. 30]

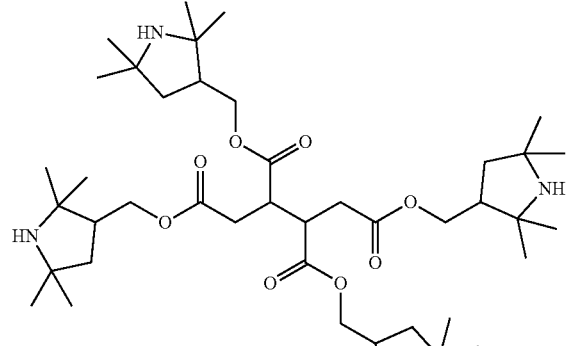

(I-4-1)

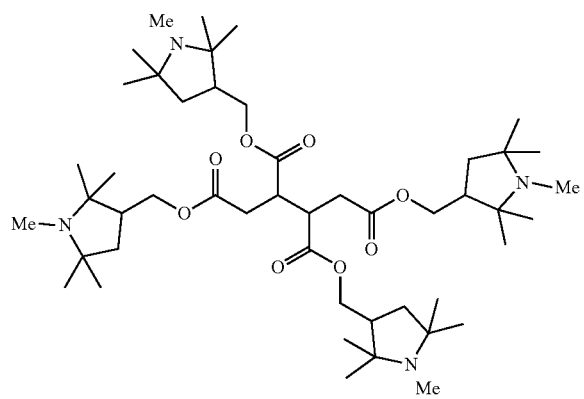

(I-4-2)

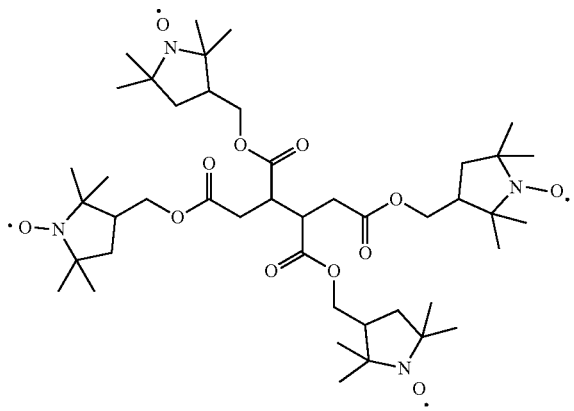

(I-4-3)

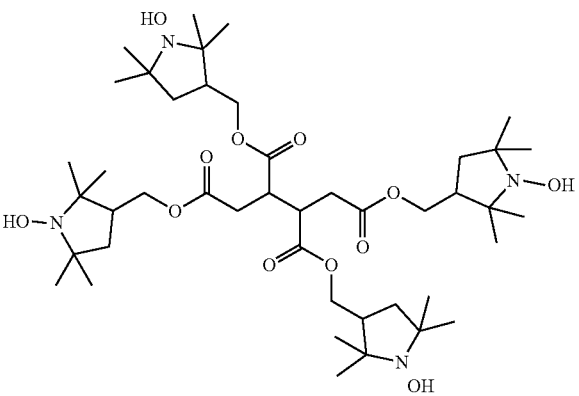

(I-4-4)

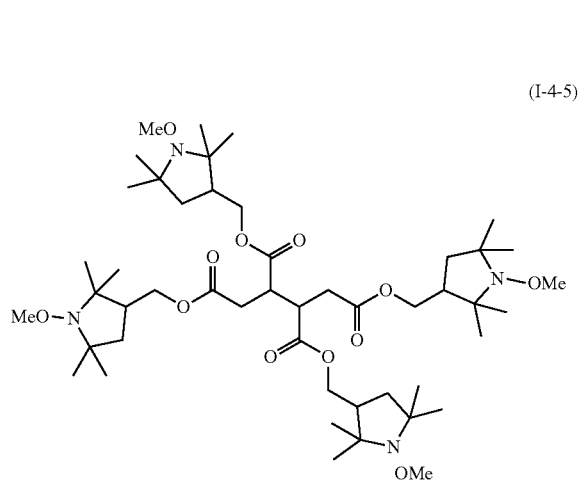

(I-4-5)

(I-4-6)
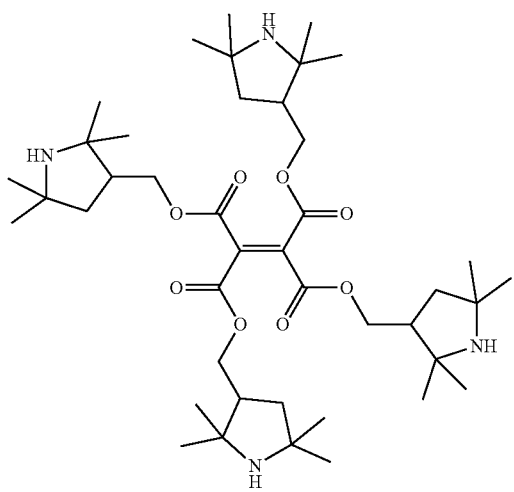
(I-4-7)
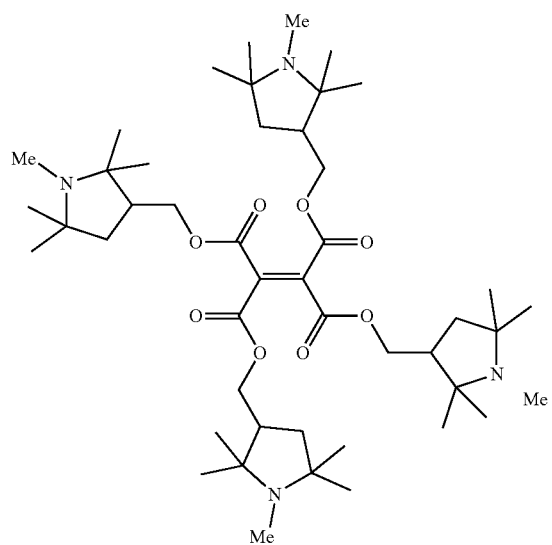
(I-4-8)
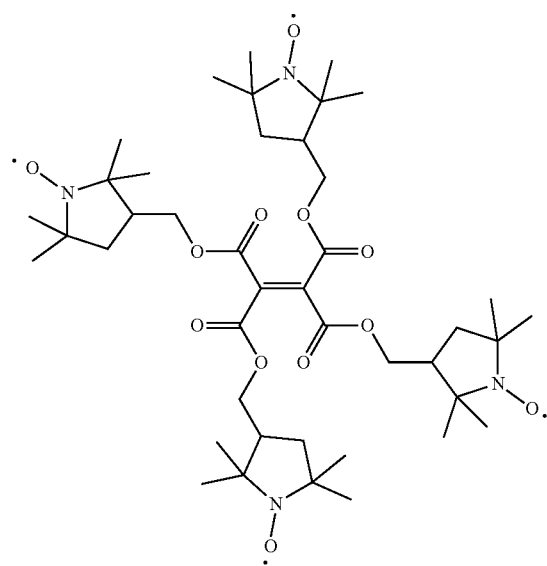
(I-4-9)
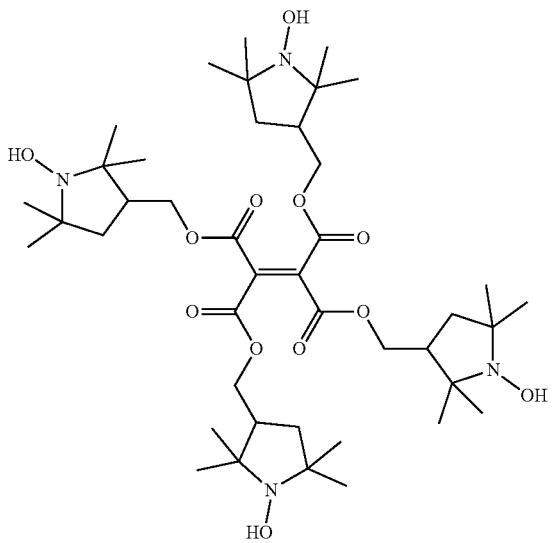
(I-4-10)
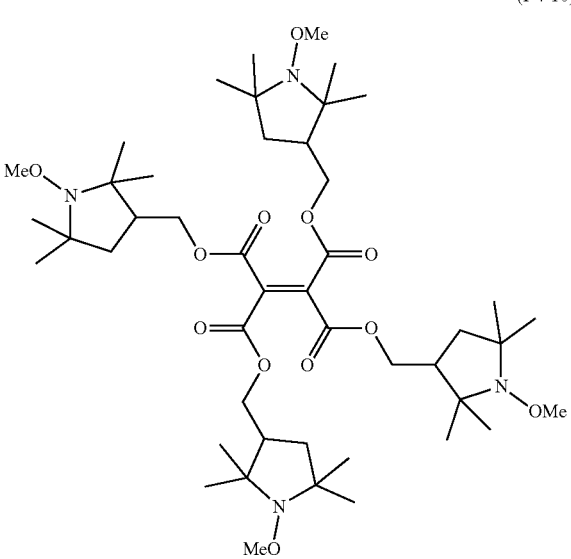
[Chem. 31]
(I-4-11)
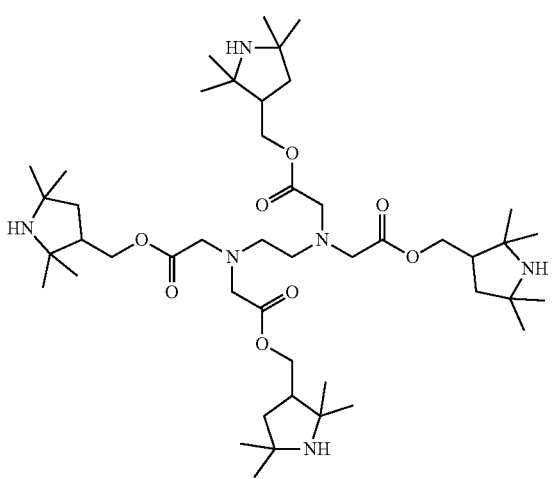

(I-4-12)
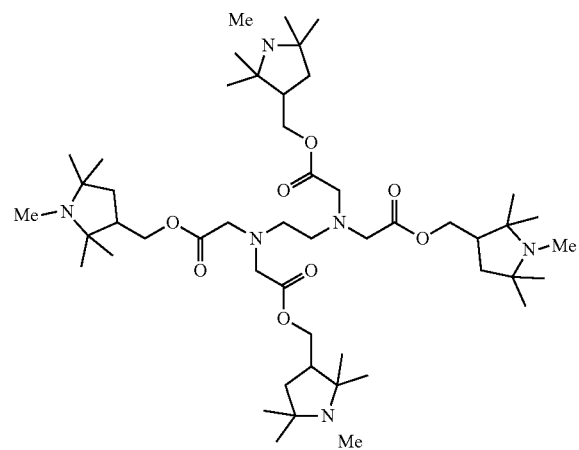
(I-4-15)
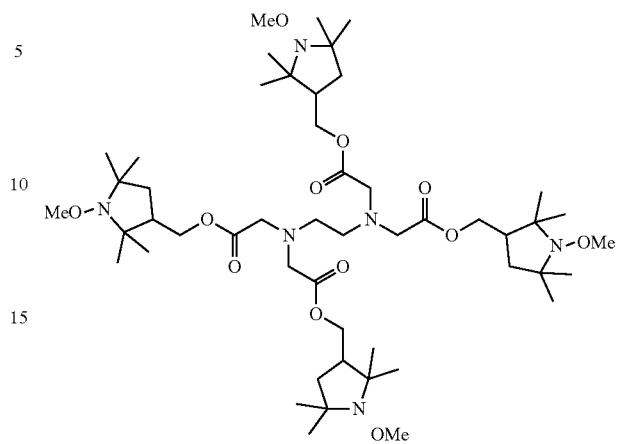
(I-4-13)
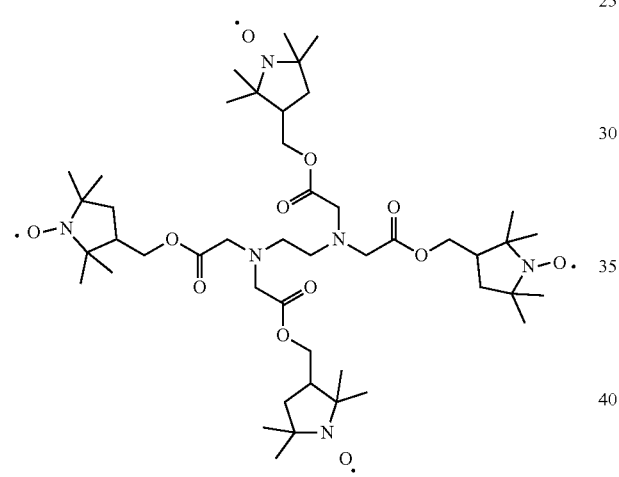
(I-4-16)
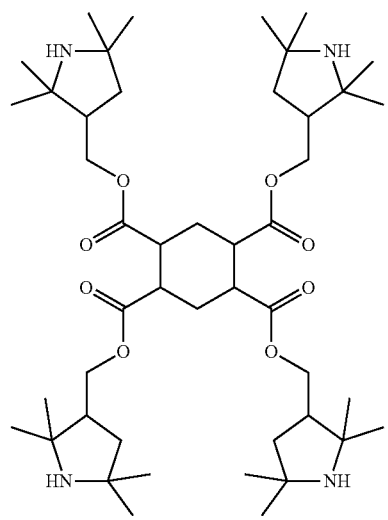
(I-4-14)
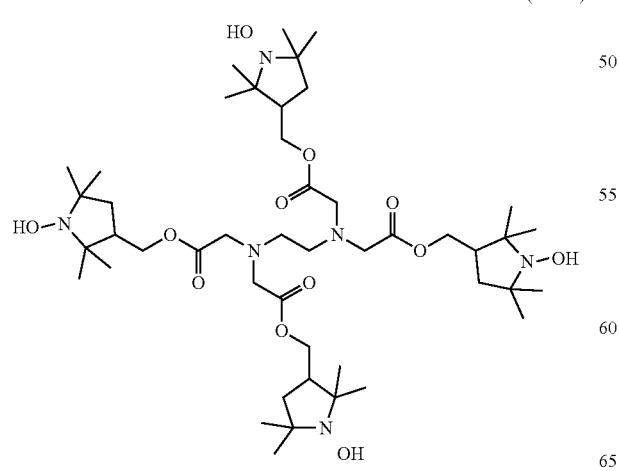
(I-4-17)
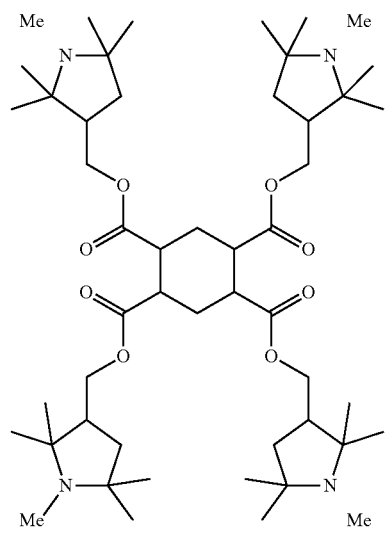

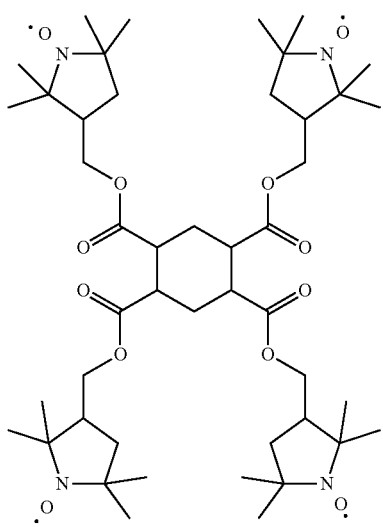
(I-4-18)
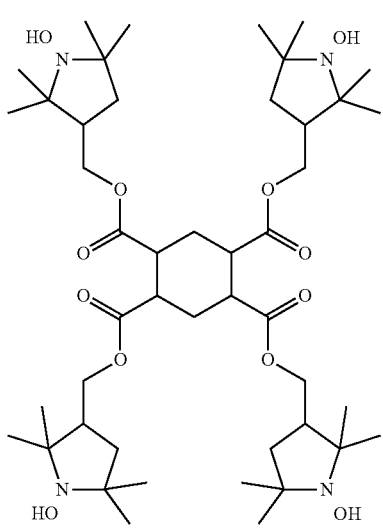
(I-4-19)
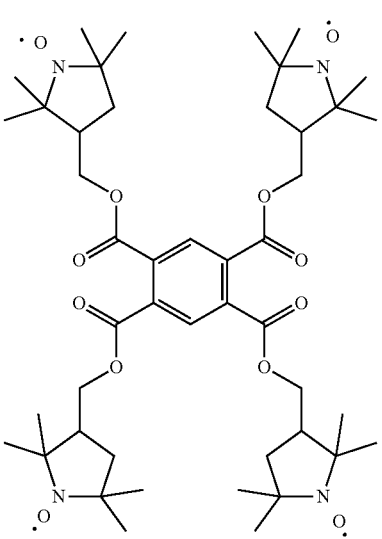
(I-4-20)
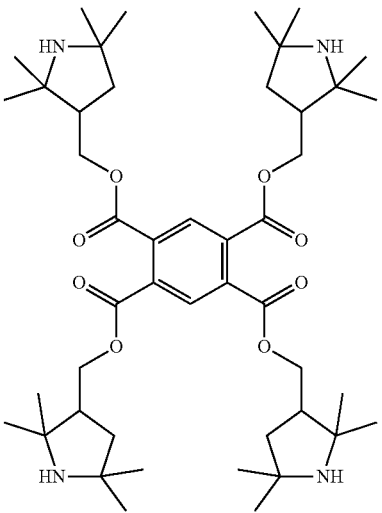
(I-4-21)
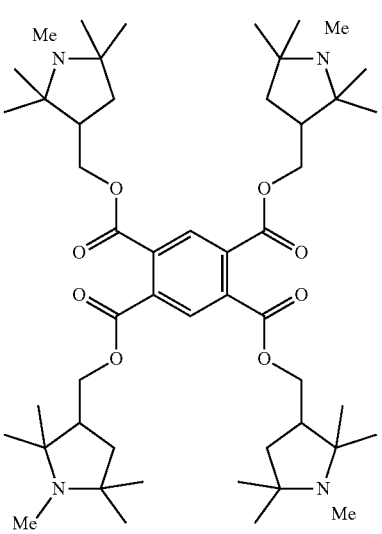
(I-4-22)
(I-4-23)

-continued
(I-4-24)
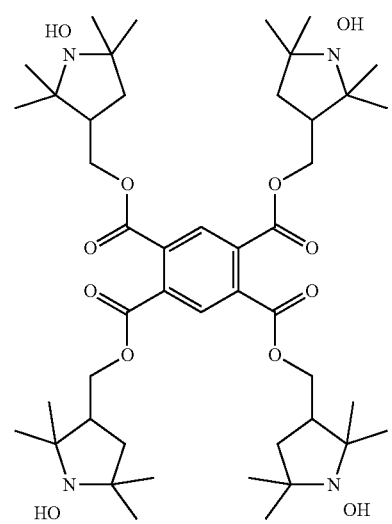
(I-4-25)
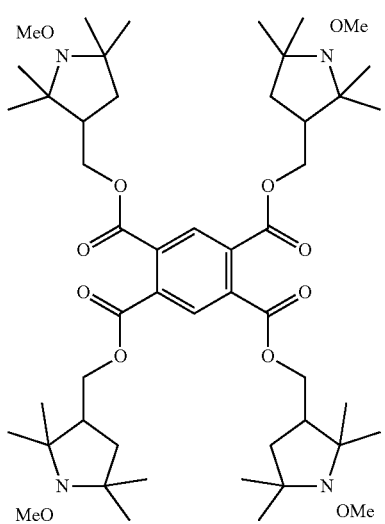
(I-4-26)
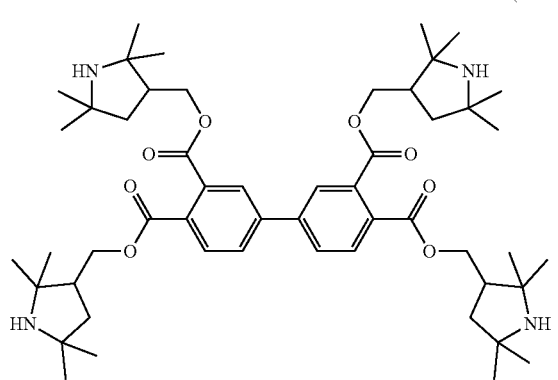
-continued
(I-4-27)
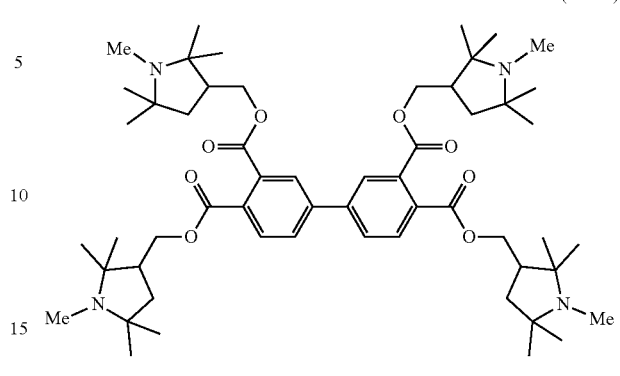
(I-4-28)
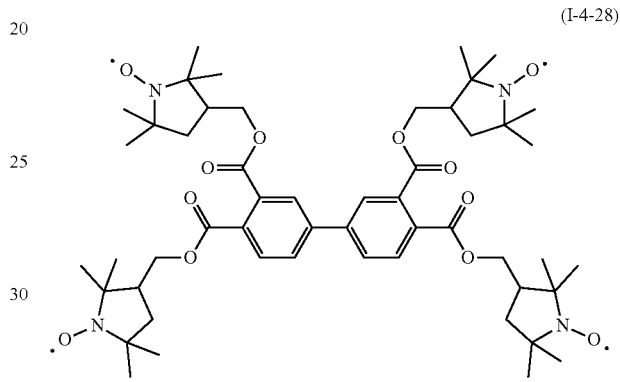
(I-4-29)
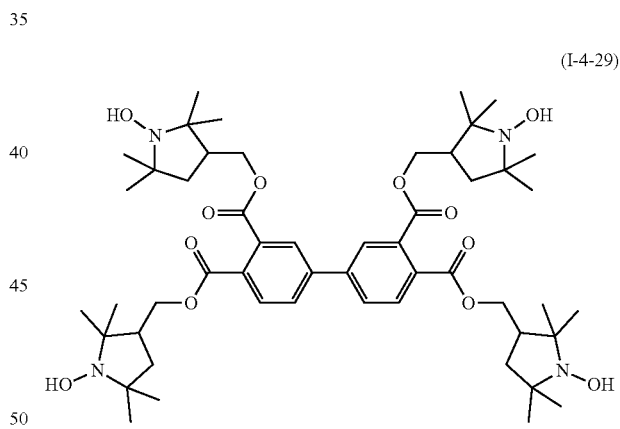
(I-4-30)
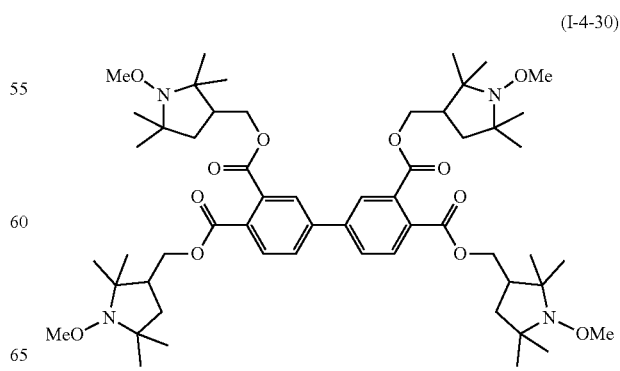

[Chem. 33]
(I-4-31)
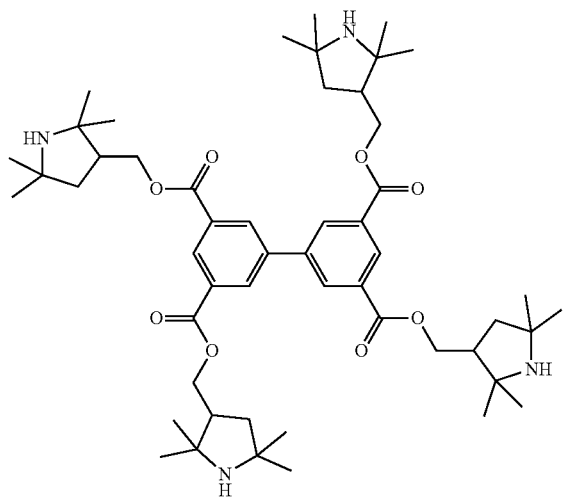
(I-4-32)
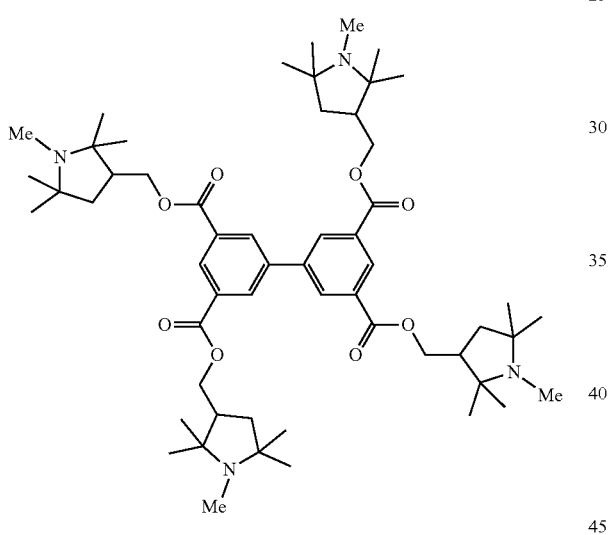
(I-4-33)
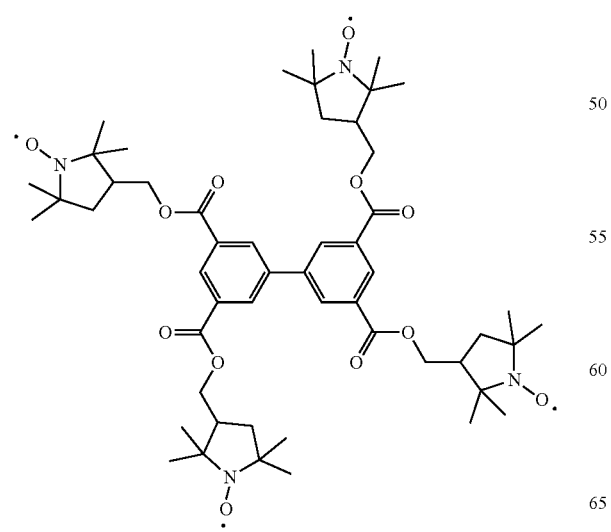
(I-4-34)
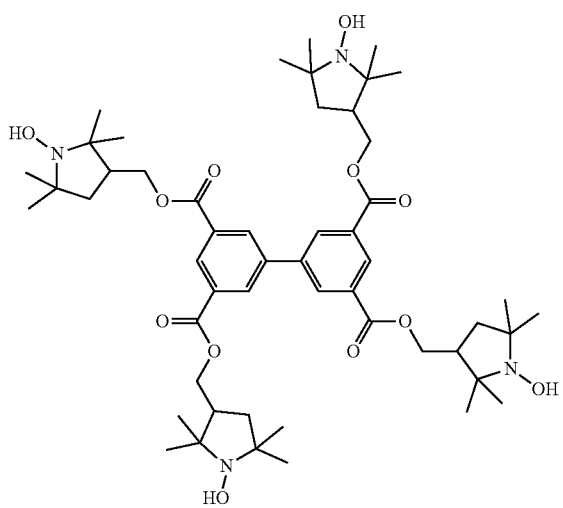
(I-4-35)
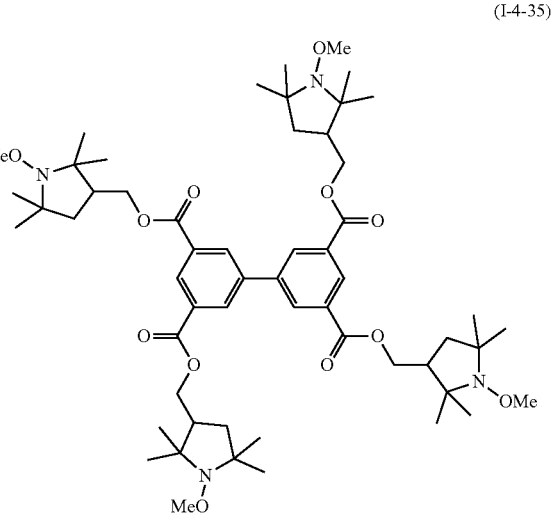
(I-4-36)
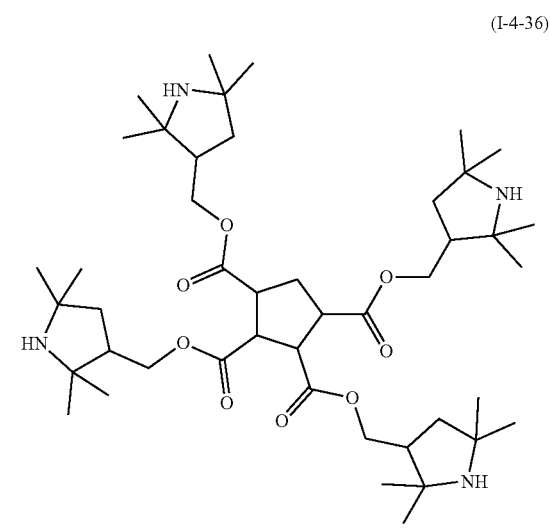

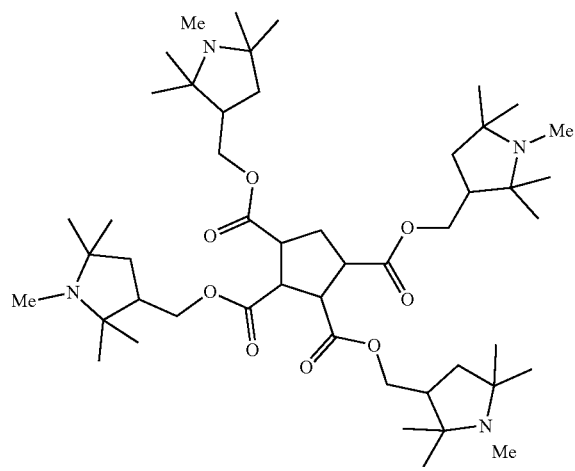
(I-4-37)
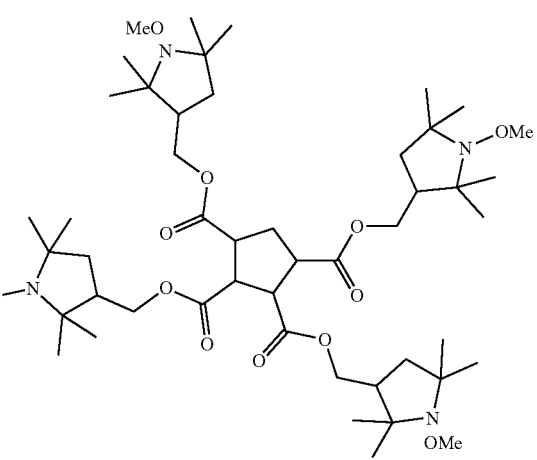
(I-4-40)
[Chem. 34]
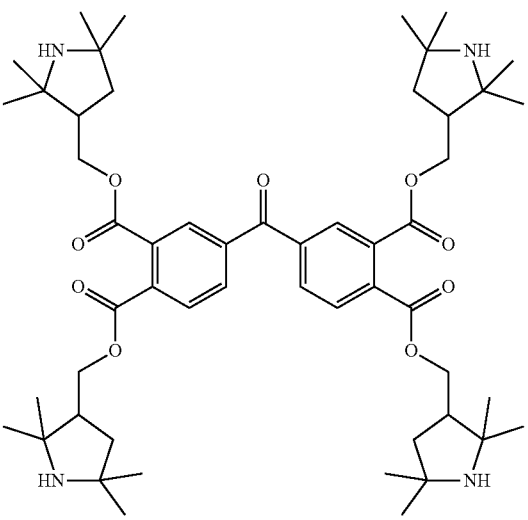
(I-4-41)
(I-4-38)
(I-4-42)
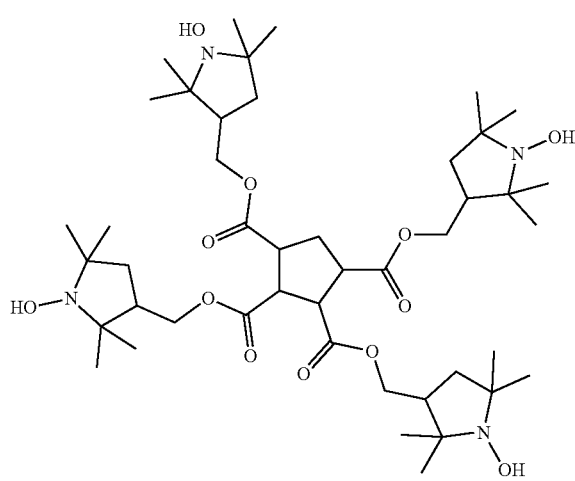
(I-4-39)

(I-4-43)
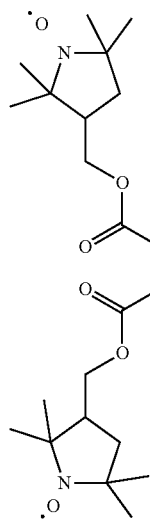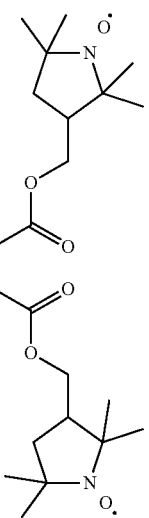
(I-4-46)
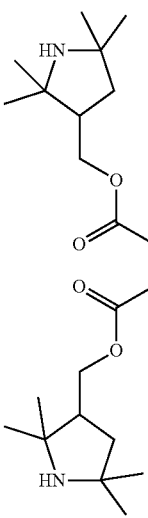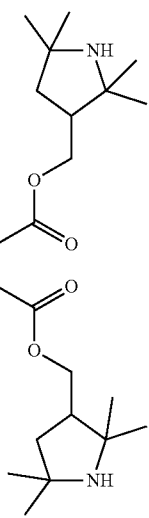
(I-4-44)
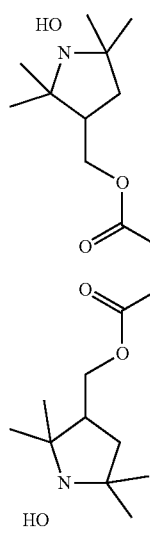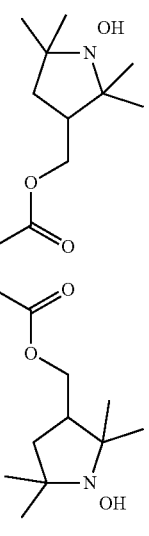
(I-4-47)
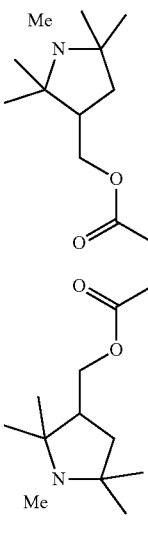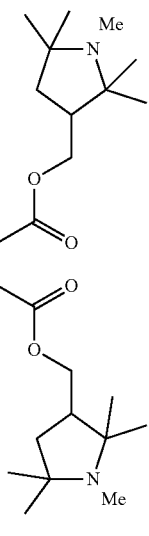
(I-4-45)
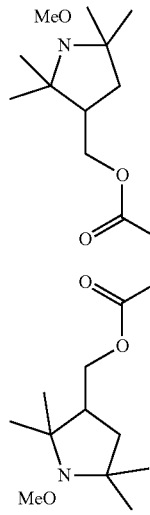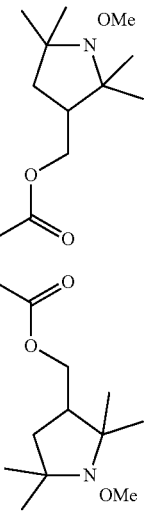
(I-4-48)
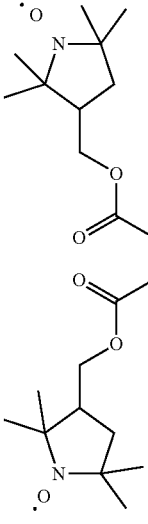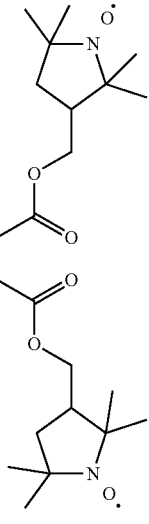

(I-4-49)
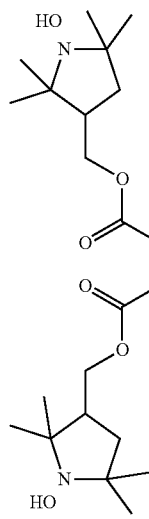
(I-4-50)
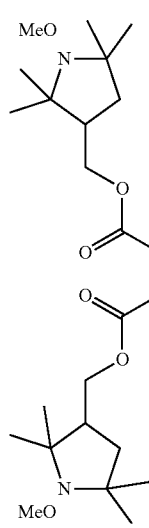
[Chem. 35]
(I-4-51)
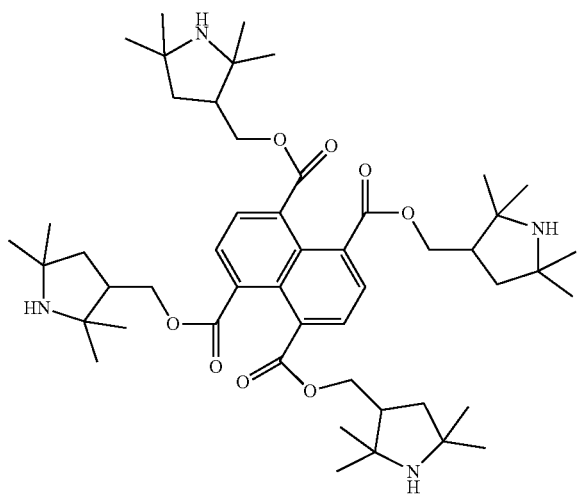
(I-4-52)
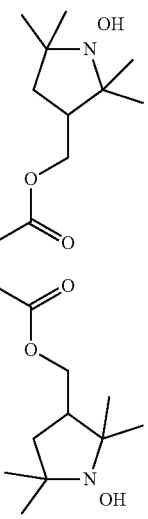
(I-4-53)
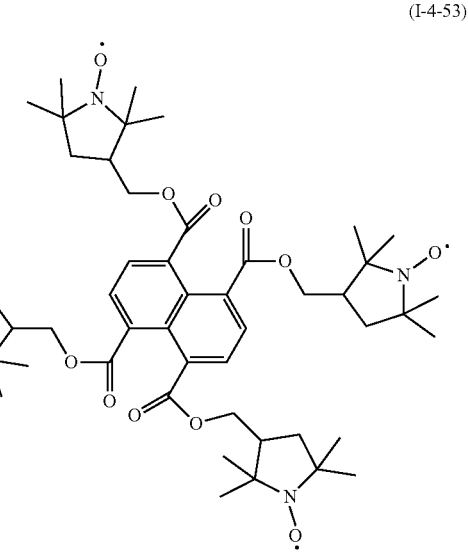
(I-4-54)
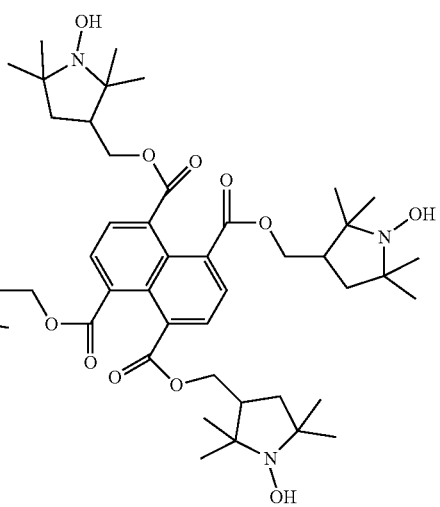

(I-4-55)
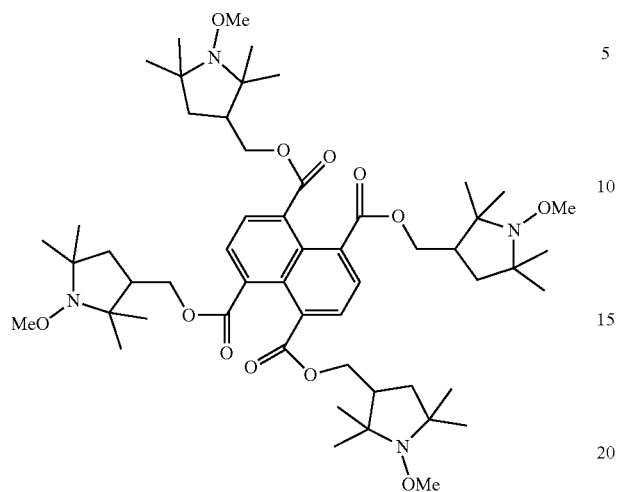
(I-4-56)
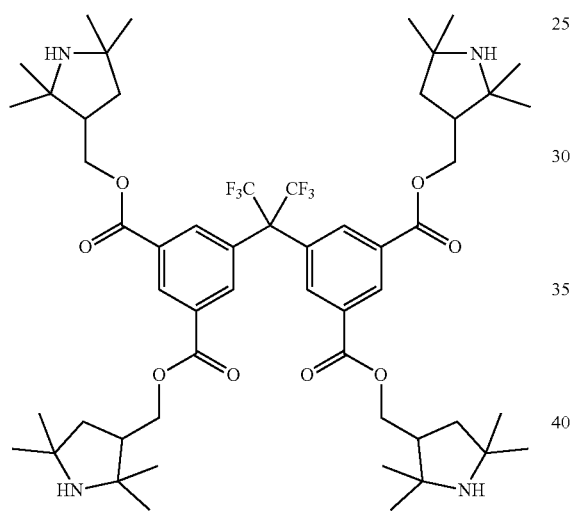
(I-4-57)
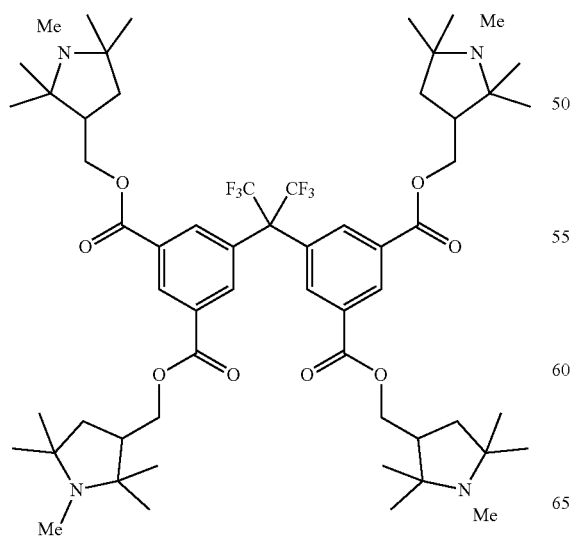
(I-4-58)
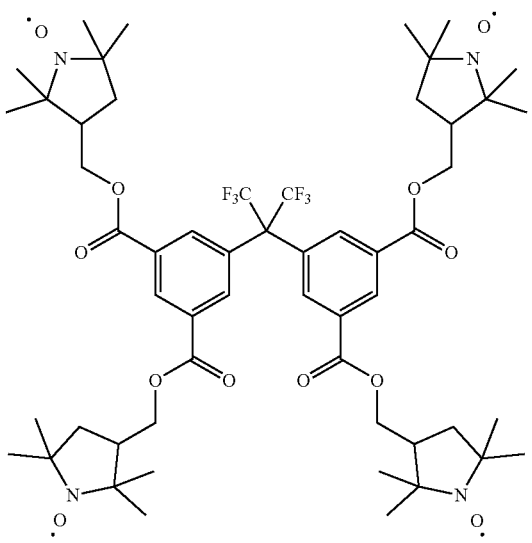
(I-4-59)
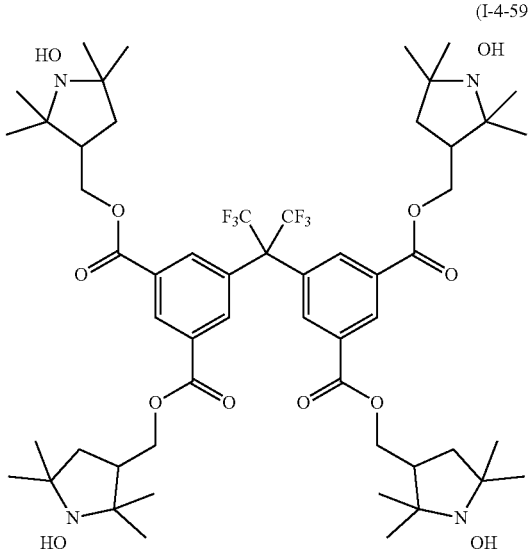
(I-4-60)
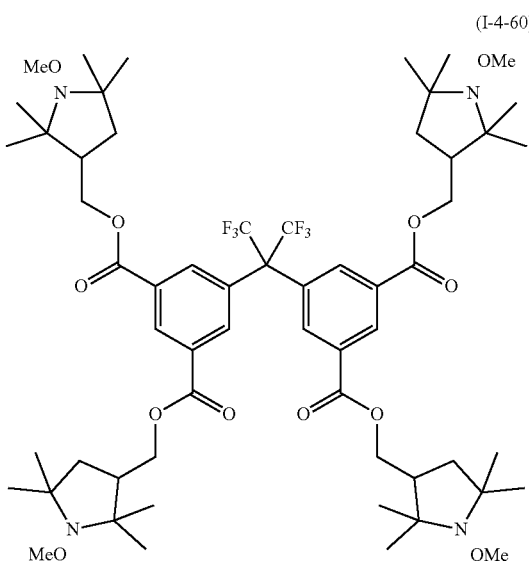

(I-4-61)
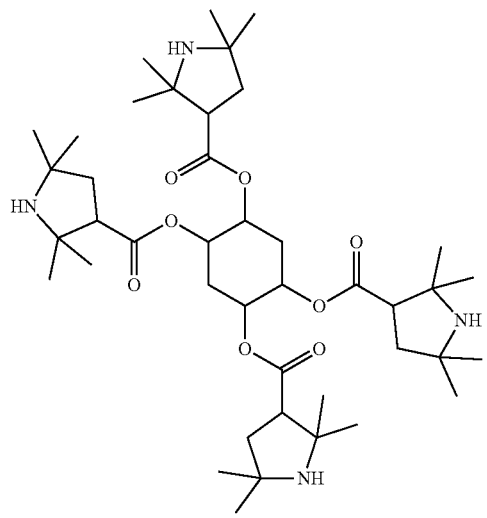
(I-4-62)
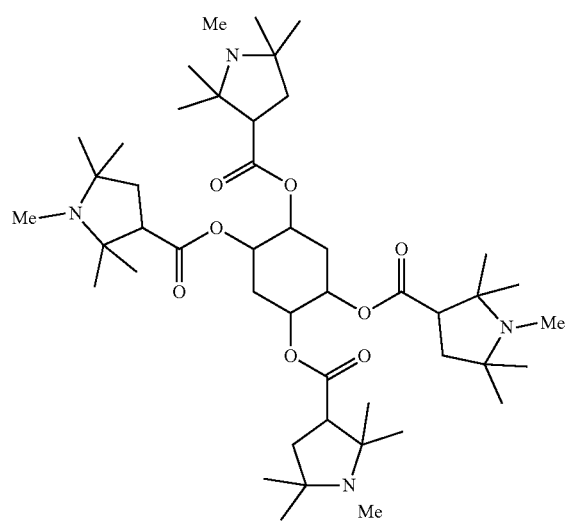
(I-4-63)
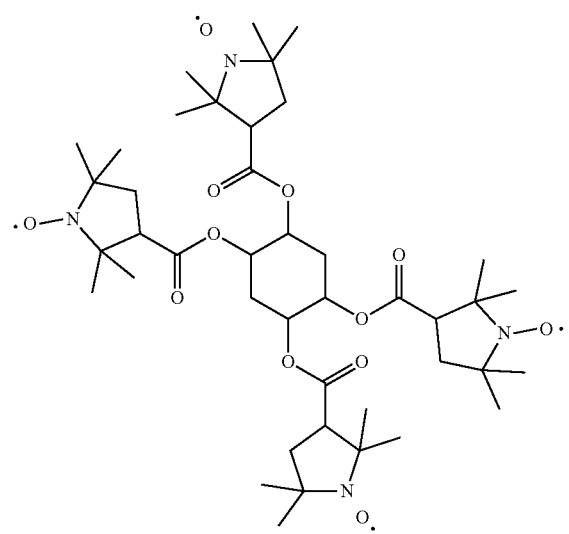
(I-4-64)
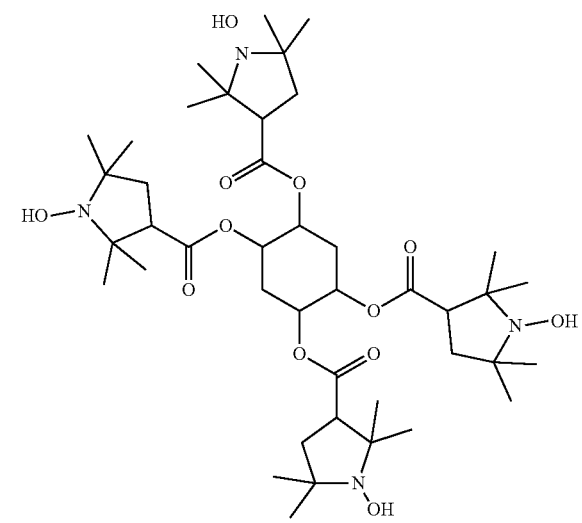
(I-4-65)
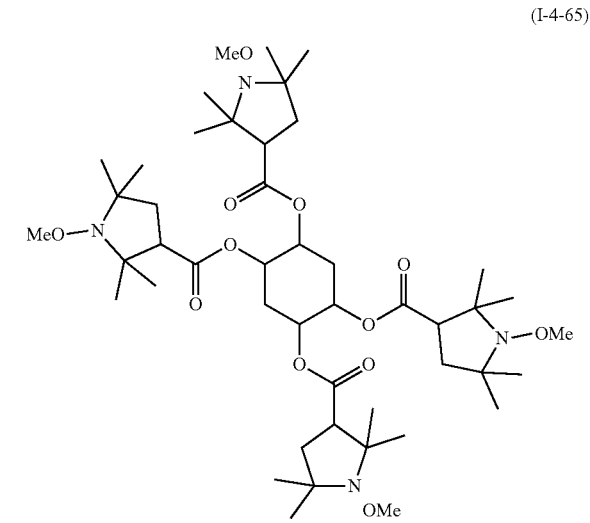
(I-4-66)
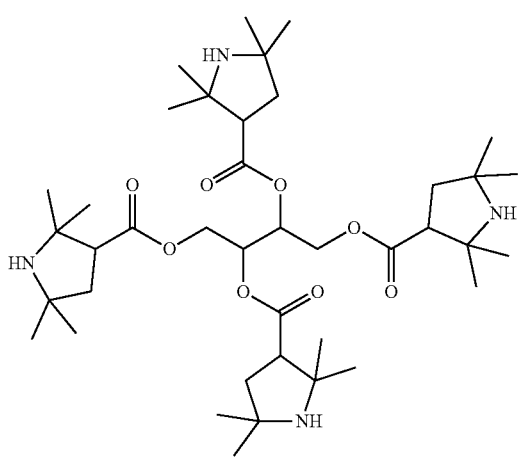

-continued
(I-4-67)
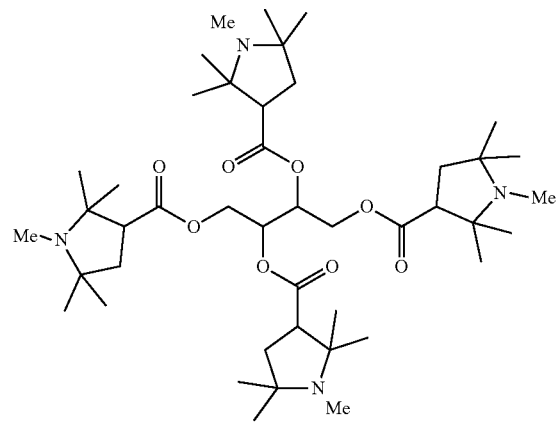
(I-4-70)
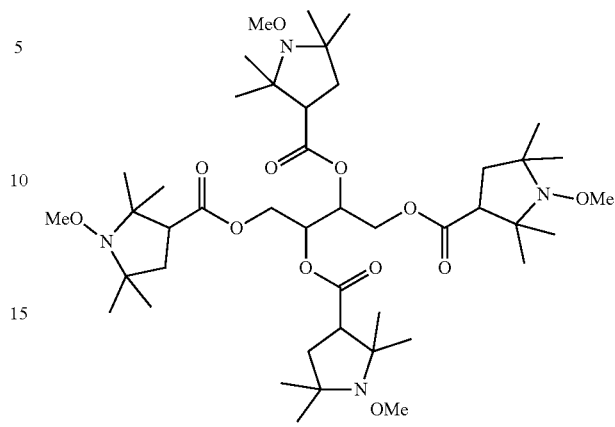
(I-4-68)
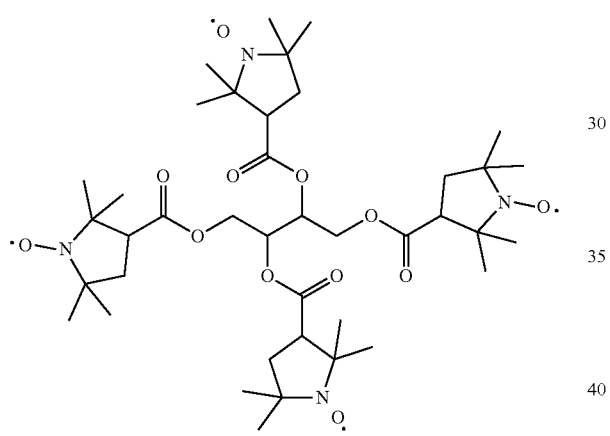
[Chem. 37]
(I-4-71)
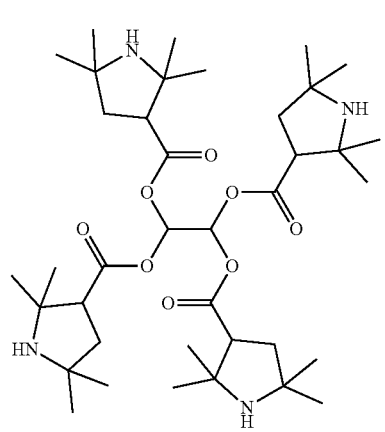
(I-4-69)
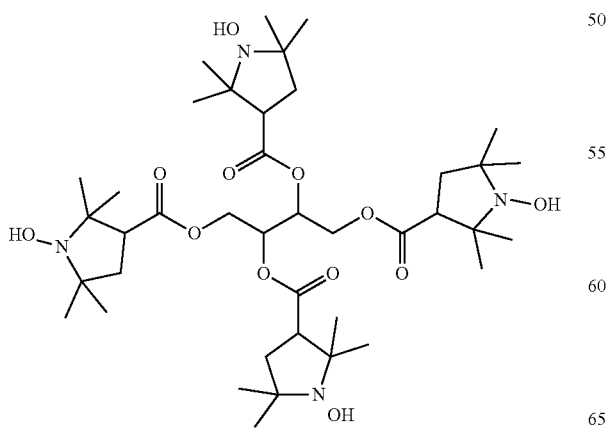
(I-4-72)
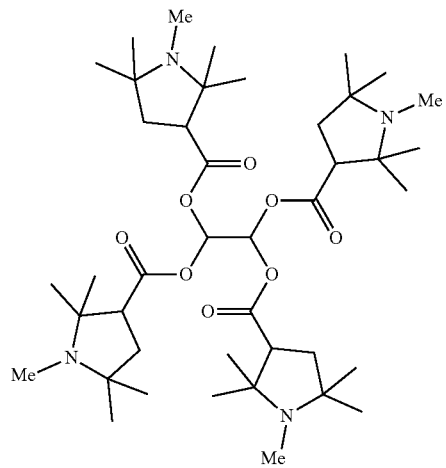

(I-4-73)
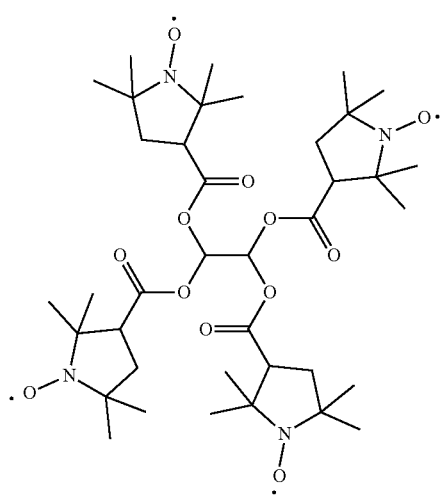
(I-4-74)
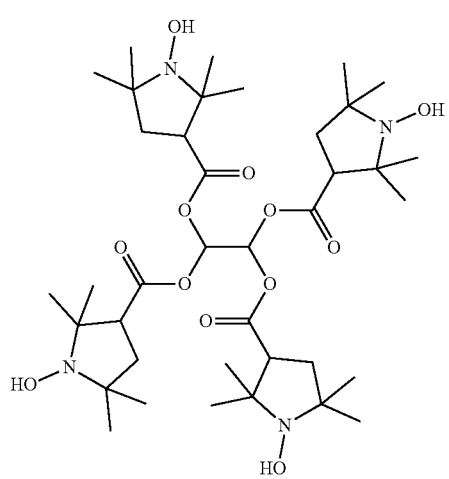
(I-4-75)
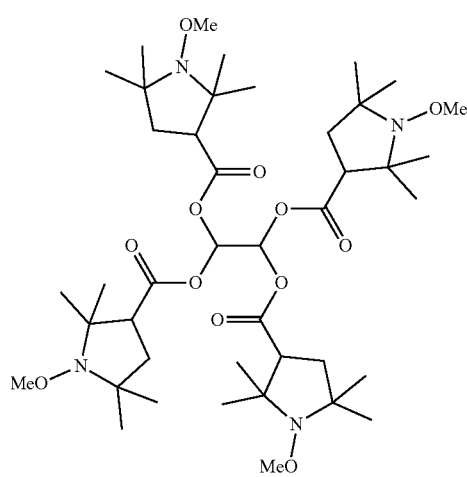
(I-4-76)
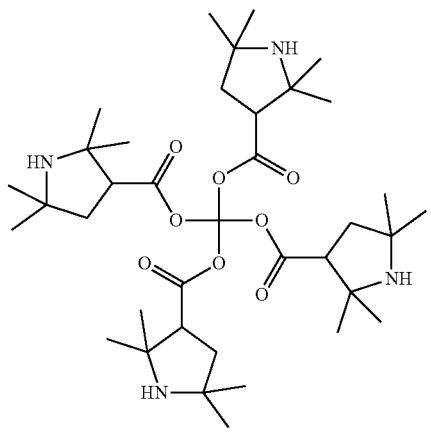
(I-4-77)
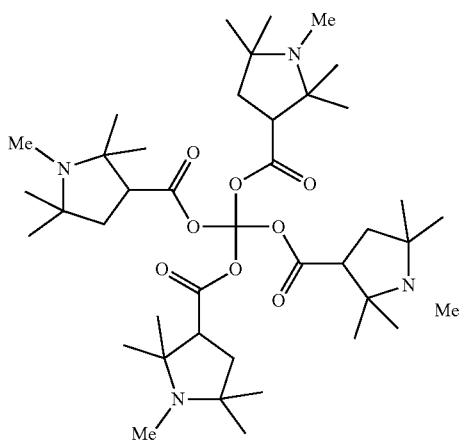
(I-4-78)
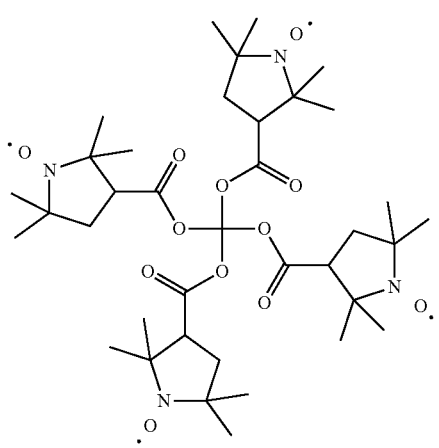

(I-4-79)
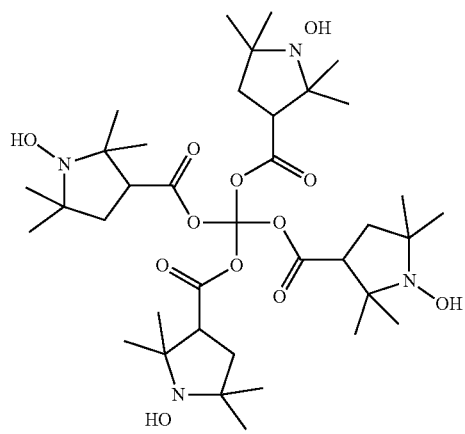
(I-4-82)
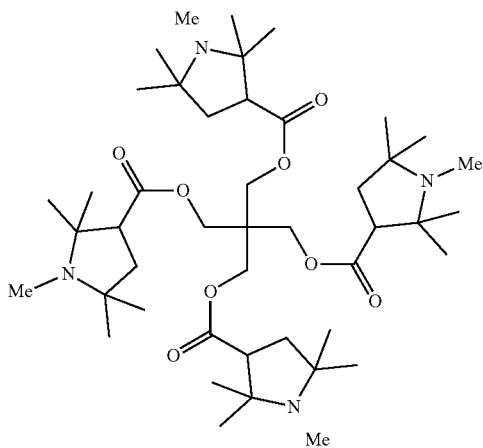
(I-4-80)
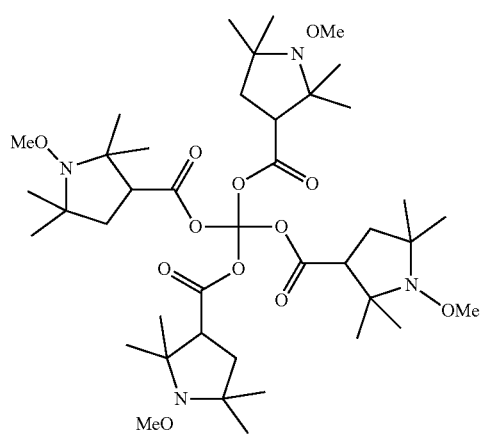
(I-4-83)
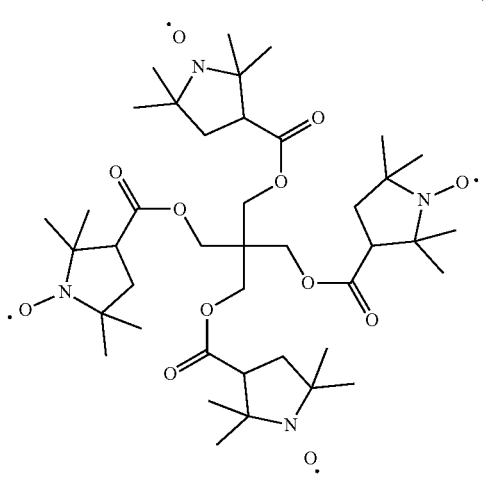
[Chem. 38]
(I-4-81)
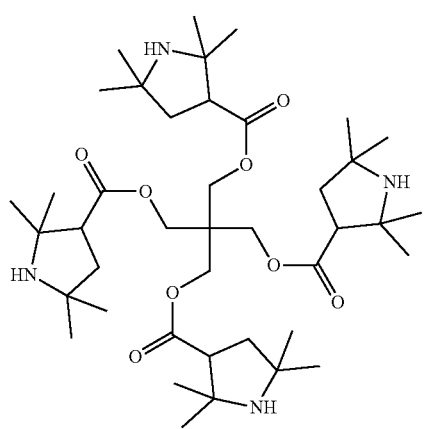
(I-4-84)
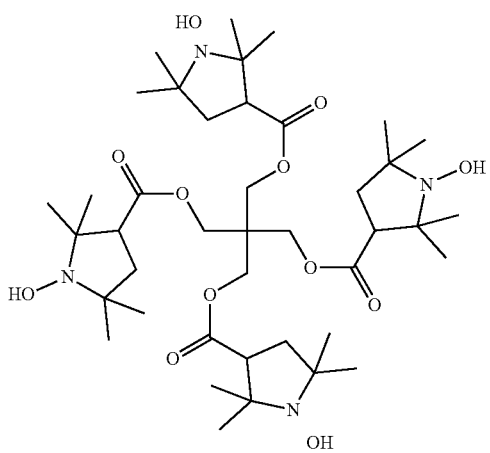

(I-4-85)
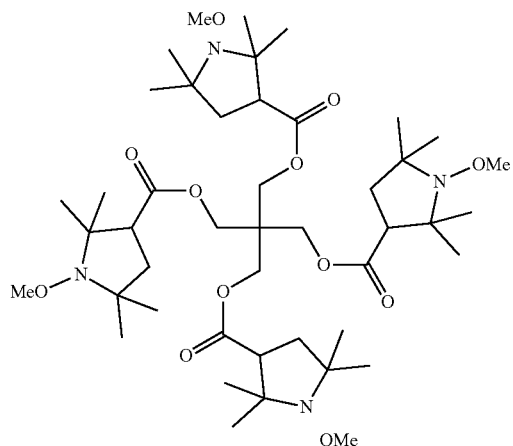
(I-4-88)
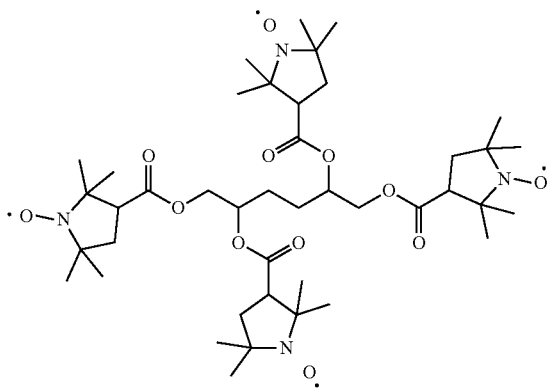
(I-4-86)
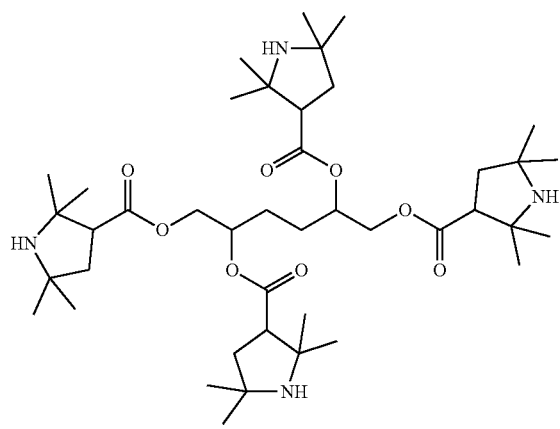
(I-4-89)
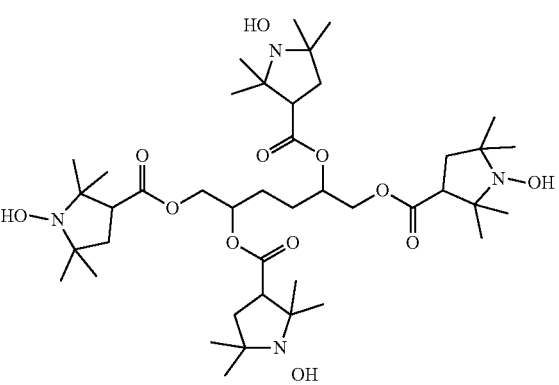
(I-4-87)
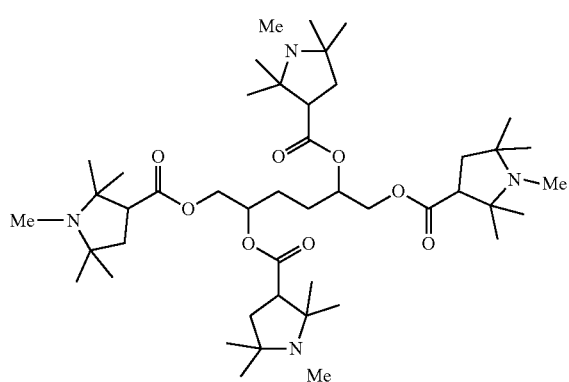
(I-4-90)
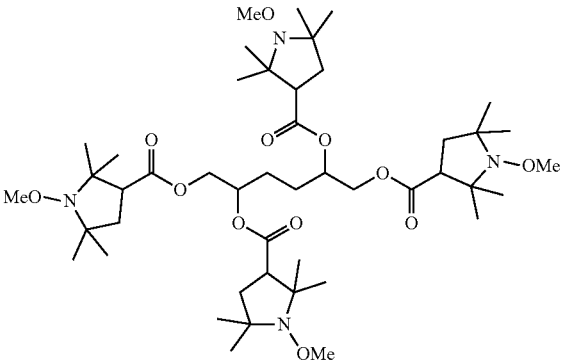

[Chem. 39]
(I-4-91)
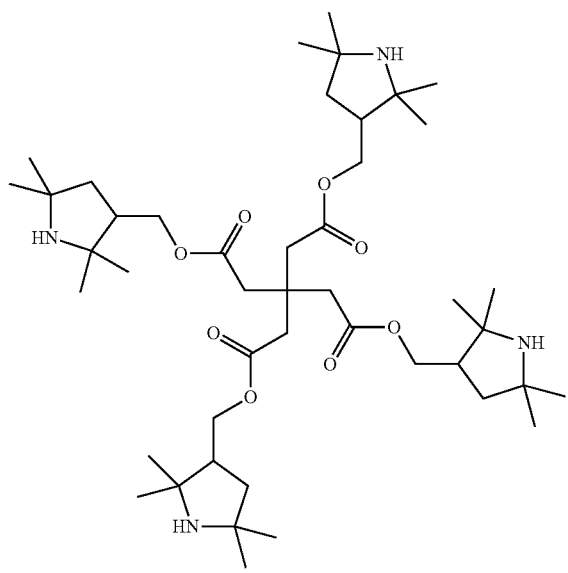
(I-4-92)
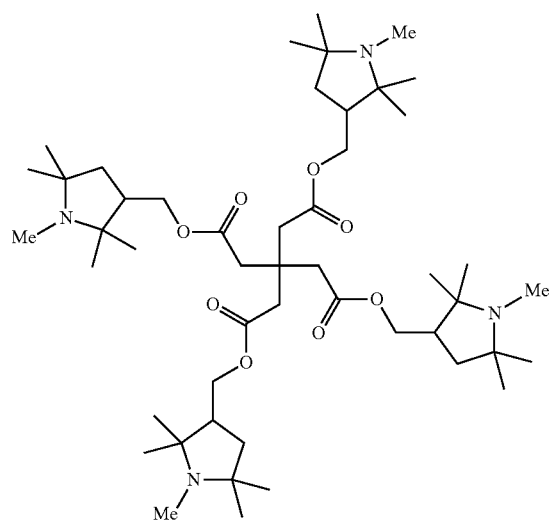
(I-4-93)
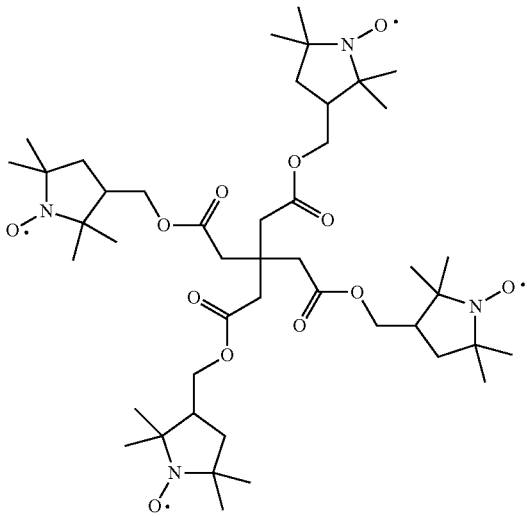
(I-4-94)
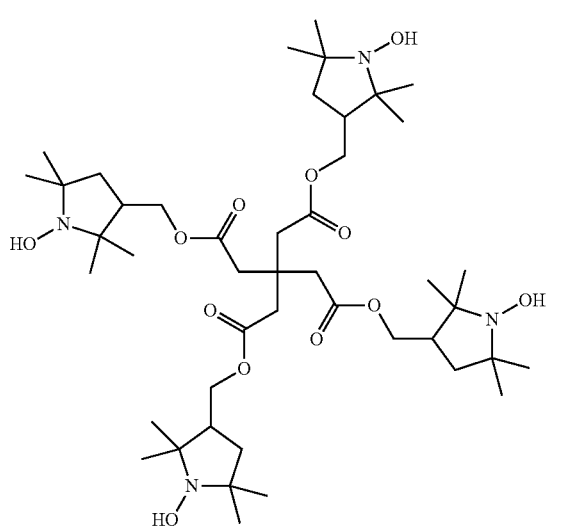
(I-4-95)
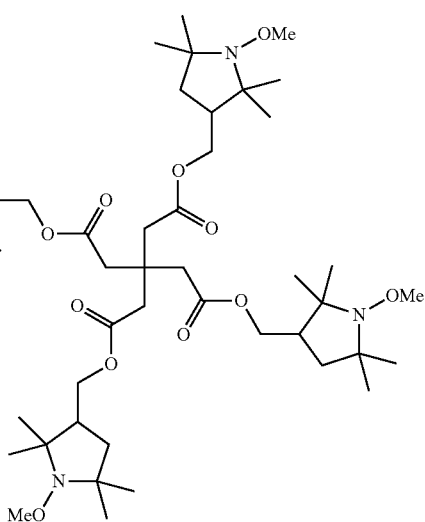
In the formulas, Me represents a methyl group.

The composition containing one kind or two or more kinds of compounds represented by General Formula (I) preferably has a liquid crystal phase at room temperature. The compound represented by General Formula (I) is preferably contained in an amount of not less than 0.01% which is the lower limit value based on the composition, preferably 0.02% or more, preferably 0.03% or more, preferably 0.05% or more, preferably 0.07% or more, preferably 0.1% or more, preferably 0.15% or more, preferably 0.2% or more, preferably 0.25% or more, preferably 0.3% or more, preferably 0.5% or more, and preferably 1% or more. In addition, the compound represented by General Formula (I) is preferably contained in an amount of 5% or less as the upper limit value in the composition, preferably 3% or less, preferably 1% or less, preferably 0.5% or less, preferably 0.45% or less, preferably 0.4% or less, preferably 0.35% or less, preferably 0.3% or less, preferably 0.25% or less, preferably 0.2% or less, preferably 0.15% or less, preferably 0.1% or less, preferably 0.07% or less, preferably 0.05% or less, and preferably 0.03% or less.

More specifically, the compound represented by General Formula (I) is preferably contained in an amount of 0.01 to 5% by mass, more preferably 0.01 to 0.3% by mass, still more preferably 0.02 to 0.3% by mass, and particularly preferably 0.05 to 0.25% by mass. More specifically, in the case of making much account of suppressing precipitation at low temperature, the content thereof is preferably 0.01 to 0.1% by mass.

The composition containing the compound represented by General Formula (I) may contain a compound having a liquid crystal phase, besides the compound represented by General Formula (I), or may contain a compound having no liquid crystal phase.

In the present invention, the compound represented by General Formula (I) can be produced as follows. Naturally, the gist and scope of the present invention are not limited by these production examples. In the following formulas, $R^1$, $R^6$ to $R^8$, n, and U represent the same meanings as $R^1$, $R^6$ to $R^8$, n, and U in General Formula (I), respectively. $R^{21}$, $R^{31}$, $R^{41}$, $R^{51}$, $R^{2c1}$ to $R^{2f1}$, $R^{3c1}$ to $R^{3f1}$, $R^{4c1}$ to $R^{4f1}$, $R^{5c1}$ to $R^{5f1}$, $R^{6g1}$ and $R^{7g1}$ each independently represent an alkyl group having 1 to 8 carbon atoms, and $R^{2c2}$ to $R^{2f2}$, $R^{3c2}$ to $R^{3f2}$, $R^{4c2}$ to $R^{4f2}$, $R^{5c2}$ to $R^{5f2}$, $R^{2e3}$, $R^{2f3}$, $R^{3e3}$, and $R^{3f3}$ each independently represent a hydrogen atom or an alkyl group having 1 to 8 carbon atoms.

(Production Method 1) Method for Producing Compound Represented by General Formulas (I-a) and (I-b)

[Chem. 40]

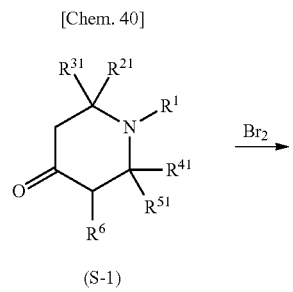

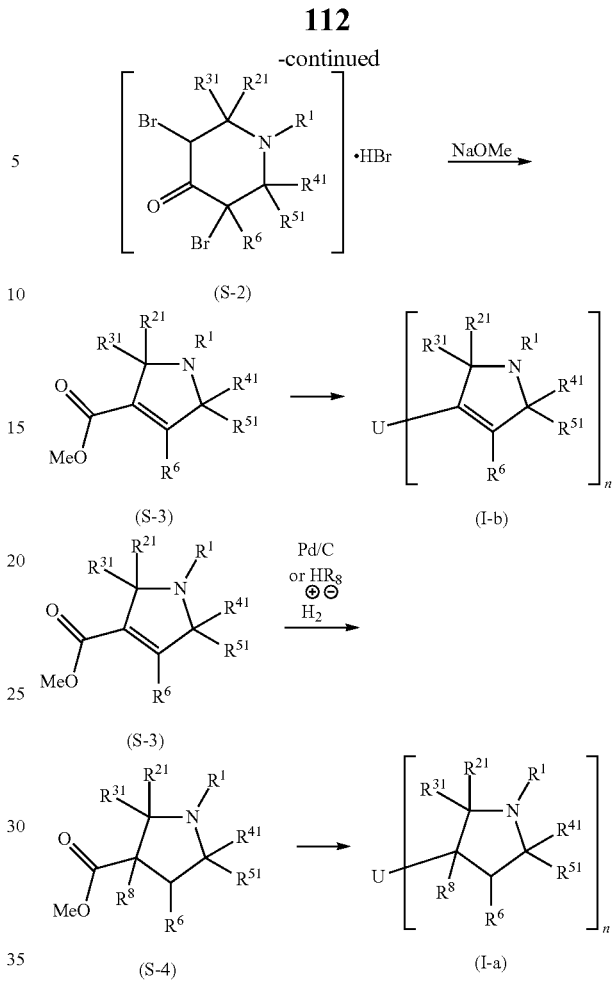

By reacting the compound represented by General Formula (S-1) with bromine, the compound represented by General Formula (S-2) can be obtained. Allowing a base such as sodium methoxide to act on a compound represented by General Formula (S-2) makes it possible to obtain a compound represented by General Formula (S-3). Alternatively, the compound represented by General Formula (I-a) may be obtained directly without going through the compound represented by General Formula (S-4) by using an anion of U as a base. The compound represented by General Formula (S-4) can be obtained by allowing hydrogen or $R^3H$ to act on the compound represented by General Formula (S-3) in the presence of a catalytic amount of palladium carbon.

By allowing a hydride reducing agent to act on the compounds represented by General Formulas (S-3) and (S-4), an alcohol can be obtained. In addition, by hydrolyzing General Formulas (S-3) and (S-4) with a base and allowing silver and bromine to act thereon, a reduced brominated product can be obtained. In addition, the compound of General Formula (S-4) is reacted with diisobutylaluminium hydride to obtain an aldehyde compound and a reaction with various phosphonium salts is performed to obtain an olefin compound, and palladium carbon is allowed to act thereon under hydrogen pressure to perform conversion into a single bond. Furthermore, General Formula (I-b) or (I-a) can be obtained by conversion of various functional groups.

(Production Method 2) Method for Producing Compound Represented by General Formula (1-c)

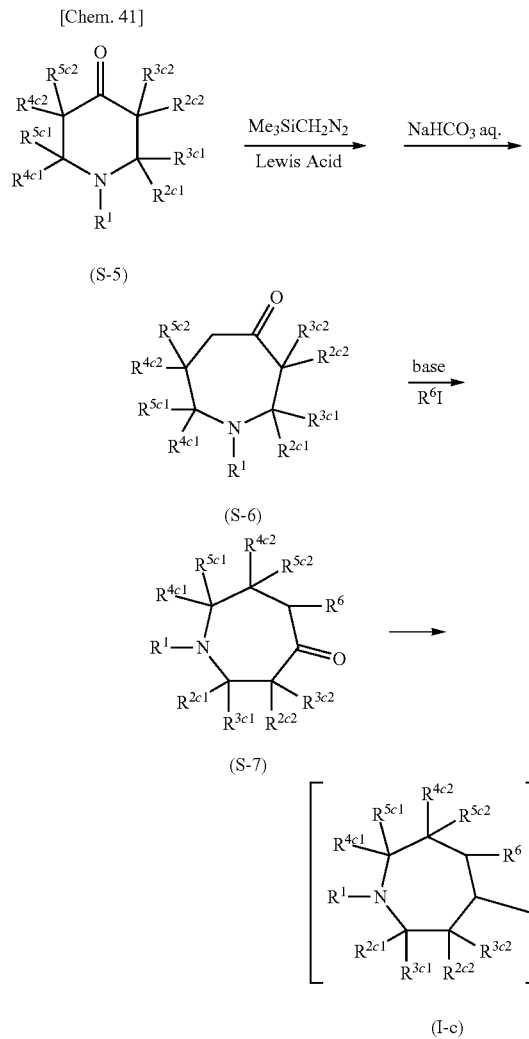

(S-5)

(S-6)

(S-7)

(I-c)

By reacting the compound represented by General Formula (S-5) with trimethylsilyldiazomethane and a catalytic amount of a Lewis acid, such as trifluoroborane etherate, metal triflate, or the like, and then reacting with sodium hydrogen carbonate water, the compound represented by General Formula (S-6) can be obtained. The compound represented by General Formula (S-7) can be obtained by reacting the compound represented by General Formula (S-6) with $R^6I$ in the presence of a basic compound. As the basic compound, amines, amides, carbamates, imides, sulfonamides, guanidines, hydrazones, hydrazides, hydrazines, heterocyclic amines, salts thereof, carbonates, metal hydrides, metal alkoxides, or alkyl metals are preferable. In particular, from the viewpoint of yield, a metal hydride, a metal alkoxide, a hydrazide salt, and bases having a basicity of pKa 15.0 or more and little nucleophilicity is more preferable. Examples thereof include lithium diisopropylamide, sodium hydride, potassium tert-butoxide, potassium hexamethyldisilazide, lithium hexamethyldisilazide, lithium tetramethyl piperidine, and the like. In addition, one kind of base may be used, or two or more kinds may be used.

The compound represented by General Formula (I-c) can be derived from the compound represented by General Formula (S-7), for example, by using the reaction conditions such as those described the literature such as Experimental Chemistry Course (edited by The Chemical Society of Japan, published by Maruzen Co., Ltd.), Organic Syntheses (A John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), Fiesers' Reagents for Organic Synthesis (John Wiley & Sons, Inc.), or listed in databases such as SciFinder (Chemical Abstracts Service, American Chemical Society) and Reaxys (Elsevier Ltd.).

(Production Method 3) Method for Producing Compound Represented by General Formula (I-d)

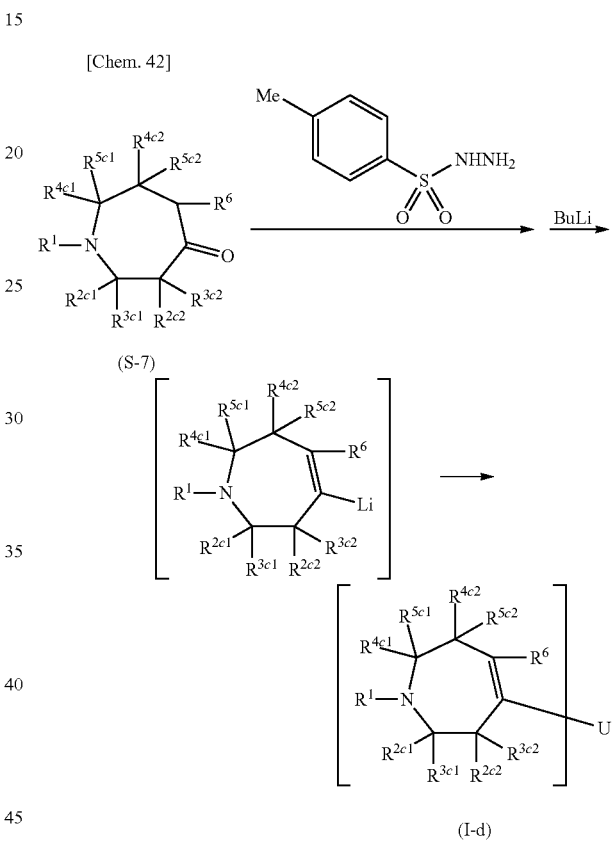

(S-7)

(I-d)

After reacting the compound represented by General Formula (S-7) with paratoluenesulfonylhydrazine to obtain a hydrazone, an alkyl metal such as butyllithium is allowed to act thereon to produce alkenyllithium. Thereafter, by allowing various electrophilic agents to act thereon or carrying out functional group conversion, the compound represented by General Formula (I-d) can be obtained. For electrophilic agents and functional group conversion, for example, it is possible to use the materials and reaction conditions described in the literature such as Experimental Chemistry Course (edited by The Chemical Society of Japan, published by Maruzen Co., Ltd.), Organic Syntheses (A John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), Fiesers' Reagents for Organic Synthesis (John Wiley & Sons, Inc.), and the like or listed in the databases such as SciFinder (Chemical Abstracts Service, American Chemical Society) and Reaxys (Elsevier Ltd.).

(Production Method 4) Method for Producing Compound Represented by General Formula (I-e)

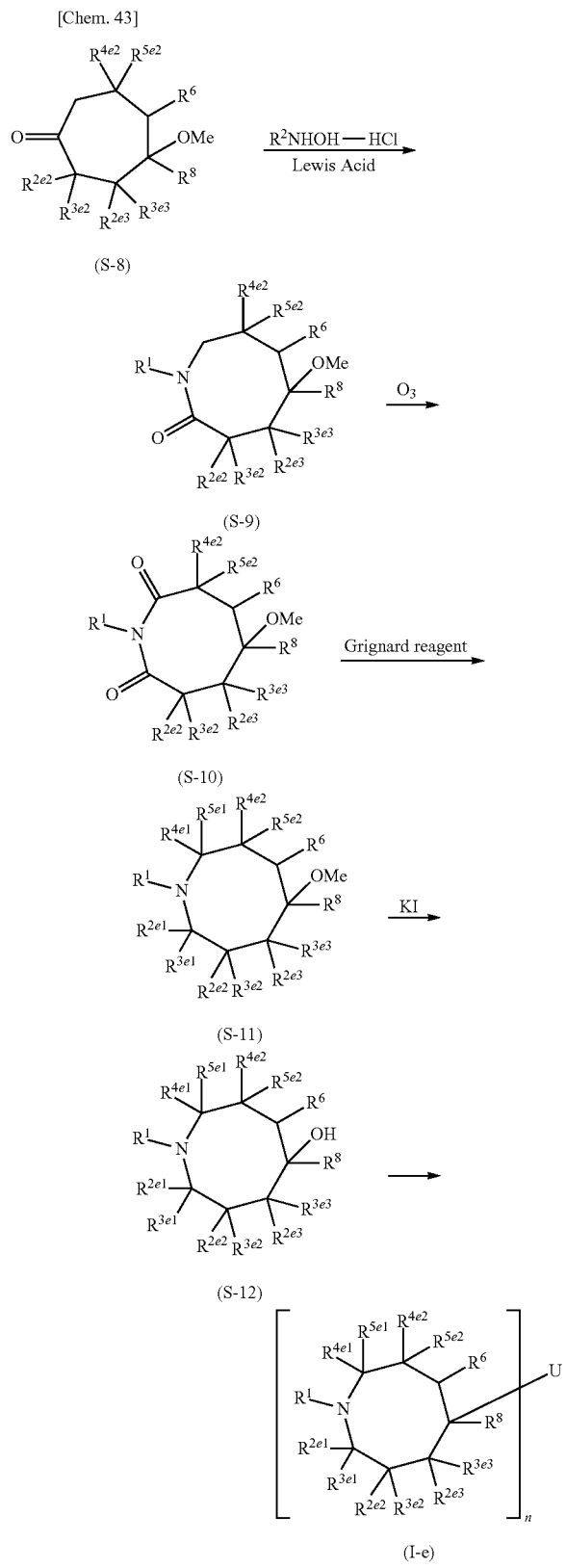

The compound represented by General Formula (S-9) can be obtained by reacting the compound represented by General Formula (S-8) with hydroxyamine in the presence of a catalytic amount of a Lewis acid, such as iron chloride (III). Reacting ozone with the compound represented by General Formula (S-9) makes it possible to obtain the compound represented by General Formula (S-10). Allowing the corresponding Grignard reagent to act on the compound represented by General Formula (S-10) makes it possible to obtain a compound represented by General Formula (S-11). After reacting the compound represented by General Formula (S-11) with potassium iodide, the compound represented by General Formula (I-e) can be obtained by carrying out various functional group conversions, for example, using the reaction conditions described in literature such as Experimental Chemistry Course (edited by The Chemical Society of Japan, published by Maruzen Co., Ltd.), Organic Syntheses (A John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), and Fiesers' Reagents for Organic Synthesis (John Wiley & Sons, Inc.) and listed in databases such as SciFinder (Chemical Abstracts Service, American Chemical Society), and Reaxys (Elsevier Ltd.).

(Production Method 5) Method for Producing Compound Represented by General Formula (I-g)

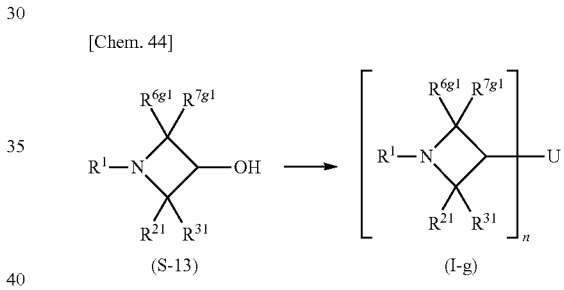

It is possible to obtain the compound represented by General Formula (I-g) by carrying out various functional group conversions to the compound represented by General Formula (S-13) according to those described in, for example, literature such as Experimental Chemistry Course (edited by The Chemical Society of Japan, published by Maruzen Co., Ltd.), Organic Syntheses (A John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), Fiesers' Reagents for Organic Synthesis (John Wiley & Sons, Inc), or by using reaction conditions listed in databases such as SciFinder (Chemical Abstracts Service, American Chemical Society), and Reaxys (Elsevier Ltd.). Examples of reaction conditions other than those described in each of the above steps include reaction conditions described in Experimental Chemistry Course (edited by The Chemical Society of Japan, published by Maruzen Co., Ltd.), Organic Syntheses (A John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), Fiesers' Reagents for Organic Synthesis (John Wiley & Sons, Inc.) or by using reaction conditions listed in databases such as SciFinder (Chemical Abstracts Service, American Chemical Society), and Reaxys (Elsevier Ltd.).

In addition, in each step, an appropriate reaction solvent can be used. Specific examples of the solvent include ethanol, tetrahydrofuran, toluene, dichloromethane, water, and the like. In the case of carrying out the reaction in a two-phase system of an organic solvent and water, a phase transfer catalyst may be also used. Specific examples of the phase transfer catalyst include benzyltrimethylammonium bromide, tetrabutylammonium bromide, and the like.

Furthermore, purification may be performed in each step as necessary. Examples of purification methods include chromatography, recrystallization, distillation, sublimation, reprecipitation, adsorption, liquid separation treatment, and the like. Specific examples of purification agents include silica gel, $NH_2$ silica gel, alumina, activated carbon, and the like.

EXAMPLES

Hereinafter, a further description will be given of the present invention with reference to Examples, but the present invention is not limited to these Examples. "%" in the compositions of the following Examples and Comparative Examples means "% by mass". The purity of the compounds was analyzed by GC or UPLC. Abbreviations of the compounds and the reaction solvents are as follows.

Tetrahydrofuran (THF),
2,2,6,6-tetramethyl-4-piperidone (TMP),
N,N-dimethylformamide (DMF)

(Example 1) Production of Compound (I-1-1)

[Chem. 45]

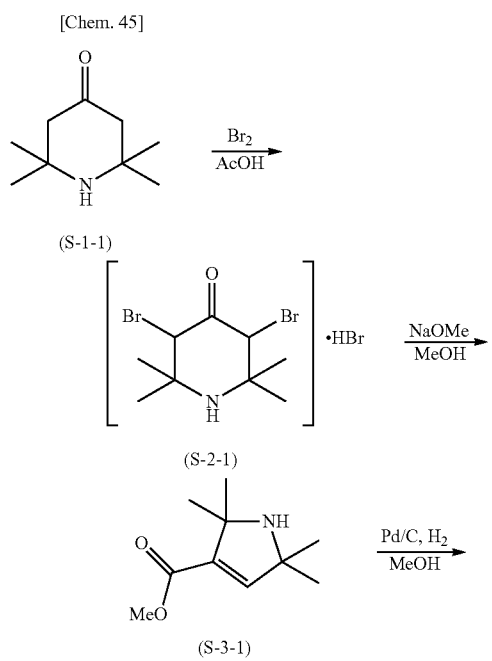

Production of Compound (S-2-1)

TMP (100 g) and acetic acid (600 ml) were added to a reaction container equipped with a stirrer, a thermometer, and a cooling tube in a nitrogen atmosphere, and bromine (100 ml) was added dropwise thereto such that the reaction system did not exceed 60° C. After stirring at 55° C. for 3 hours, the mixture was cooled to room temperature, the precipitated solid was collected by filtration and dried by heating under reduced pressure to obtain compound (S-2-1) (217 g).

Production of Compound (S-3-1)

Sodium methoxide (28% methanol solution) (430 ml) and methanol (430 ml) were added to a reaction container equipped with a stirrer and a thermometer in a nitrogen atmosphere, and the compound (S-2-1) (217 g) was added thereto little by little under ice cooling. Thereafter, the temperature was returned to room temperature and stirring was carried out for 1 hour, and then the reaction solution was concentrated under reduced pressure. Hexane (500 ml) and THF (500 ml) were added to the obtained residue, the solids were removed by filtration, and a 10% potassium carbonate aqueous solution was added thereto to separate into layers, thereby obtaining an organic layer. The aqueous layer was extracted with a mixed solvent of hexane (200 ml) and THF (200 ml), the resulting mixed solvent was mixed with the organic layer obtained above, dried over sodium sulfate, and concentrated under reduced pressure. Hexane (240 ml) was added to the obtained residue, and the residue was purified with a silica gel column and concentrated under reduced pressure to obtain a colorless liquid compound (S-3-1) (76.9 g).

GC-MS: m/z 168.22 [M-15$^+$]
$^1$H-NMR (400 MHz, DMSO-d6) δ: 1.35 (s, 6H), 1.71 (s, 6H), 5.49 (s, 2H), 9.32-9.37 (br, 1H)

Production of Compound (I-1-1)

Compound (S-3-1) (76.9 g), palladium carbon (3.8 g), and methanol (320 ml) were added to a 1000 ml pressure-resistant autoclave, and the mixture was stirred for 5 hours at room temperature while hydrogen pressure (0.3 Mpa) was applied thereto. The reaction solution was filtered, palladium carbon was removed, and then the mixture was concentrated under reduced pressure. The obtained residue was dissolved in hexane (70 ml) and ethyl acetate (15 ml), passed through an amino silica column, and concentrated under reduced pressure to obtain a compound (I-1-1) (74.6 g).

GC-MS: m/z 170.26 [M-15$^+$]
$^1$H-NMR (400 MHz, CDCl$_3$) Δ: 1.24 (s, 6H), 1.37 (s, 6H), 1.71-1.75 (br, 1H), 3.70 (s, 3H), 6.59 (s, 1H)

(Example 2) Production of Compound (I-2-7)

[Chem. 46]

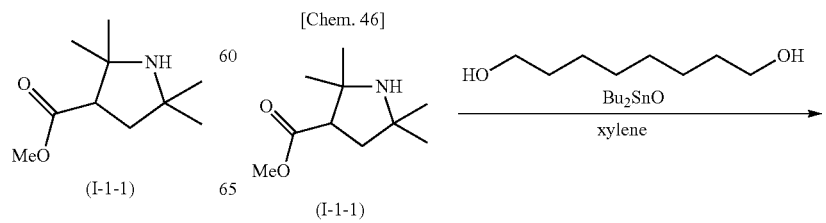

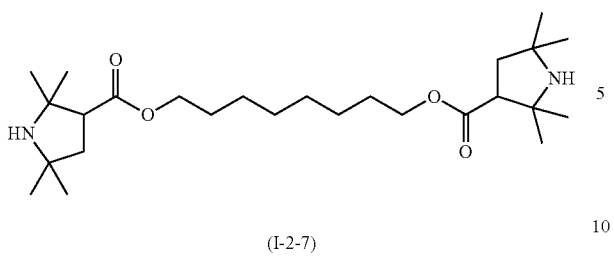

(I-2-7)

The compound (I-1-1) (20.4 g), dibutyltin oxide (823 mg), 1,8-octanediol (4.12 ml), and xylene (200 ml) were added to a reaction container equipped with a stirrer, a thermometer, and a cooling tube in a nitrogen atmosphere, the mixture was stirred under heating reflux for 10 hours, and then the reaction solution was concentrated under reduced pressure. The obtained residue was dissolved in hexane (100 ml), passed through a silica gel column and an amino silica column several times, and concentrated under reduced pressure to obtain a colorless liquid compound (I-2-7) (6.02 g).

GC-MS: m/z 437.59 [M-15$^+$]

Example 3 (Compound (I-1-7a)) to Example 26 (Compound (I-4-86)) were produced using the same reaction as in Example 2 and methods based on known methods as necessary.

[Chem. 47]

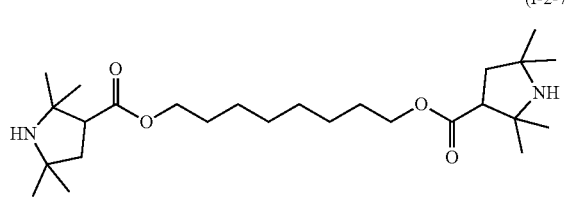

(I-2-7)

Example 2

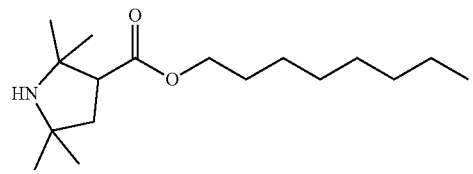

(I-1-7a)

Example 3

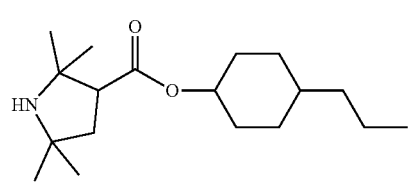

(I-1-8a)

Example 4

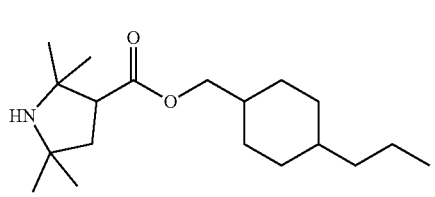

(I-1-9a)

Example 5

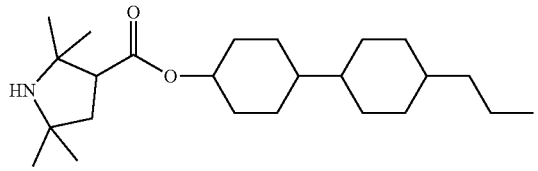

(I-1-25a)

Example 6

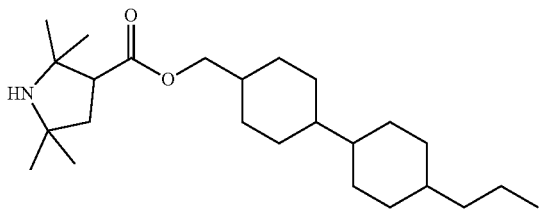

(I-1-31a)

Example 7

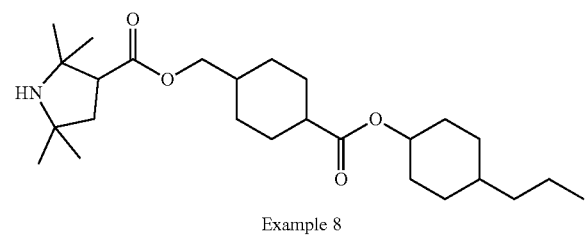

(I-1-39a)

Example 8

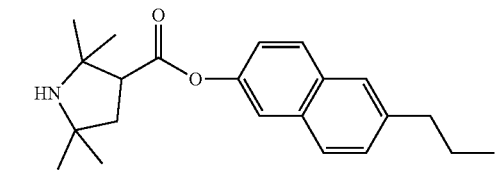

(I-1-87)

Example 9

[Chem. 48]

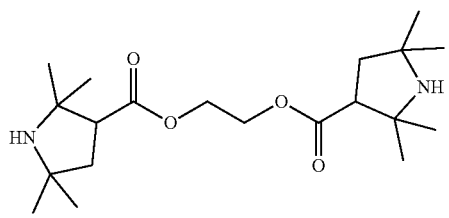

(I-2-1)

Example 10

(I-2-30)
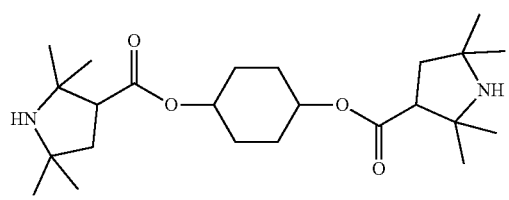
Example 11
(I-2-31)
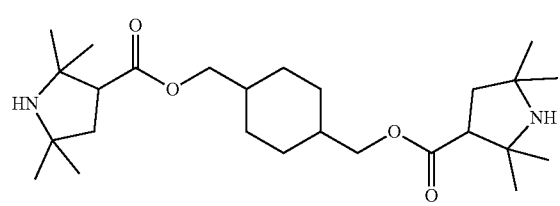
Example 12
(I-2-32)
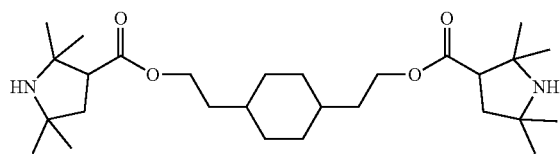
Example 13
(I-2-33)
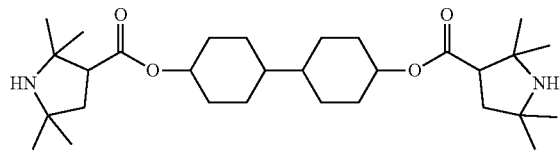
Example 14
(I-2-34)
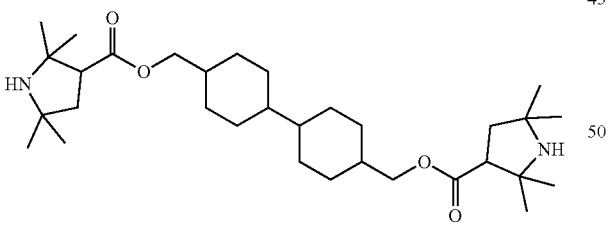
Example 15
(I-2-37)
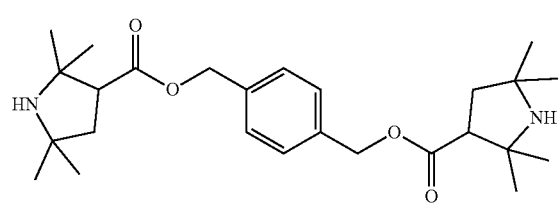
Example 16
(I-2-40)
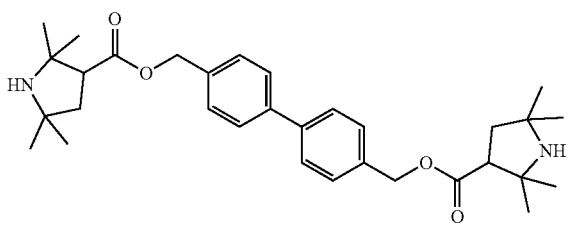
Example 17
(I-2-41)
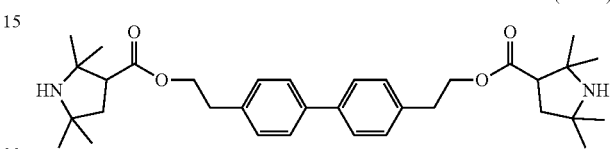
Example 18
[Chem. 49]
(I-3-9)
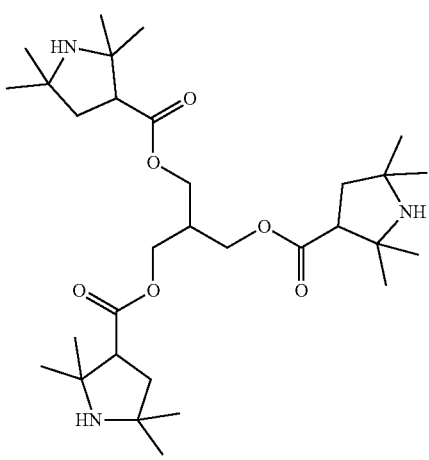
Example 19
(I-3-22)
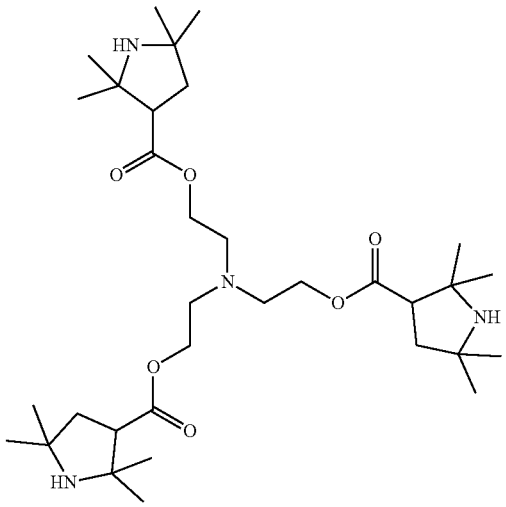
Example 20

(I-3-40)
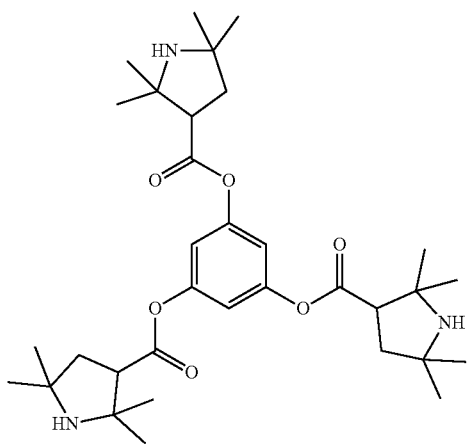
Example 21
(I-3-52)
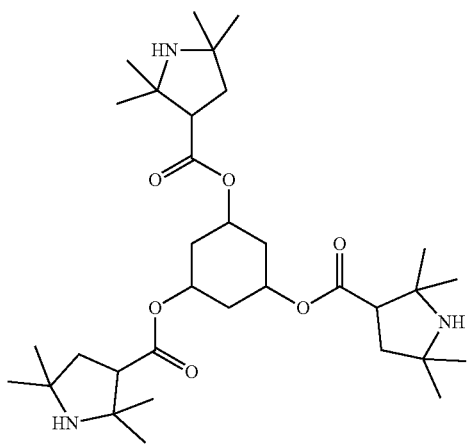
Example 22
[Chem. 50]
(I-4-61)
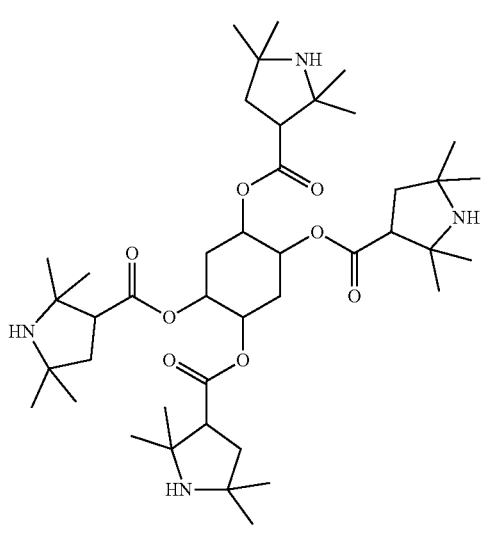
Example 23
(I-4-66)
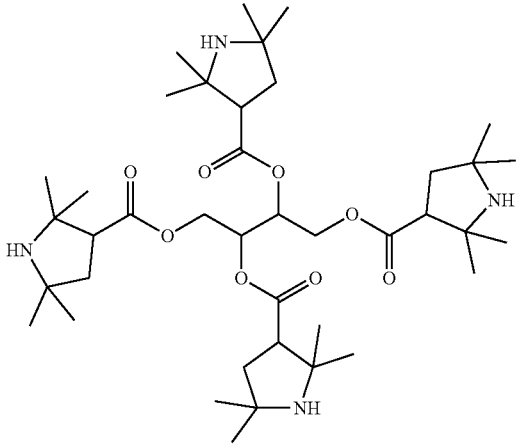
Example 24
(I-4-81)
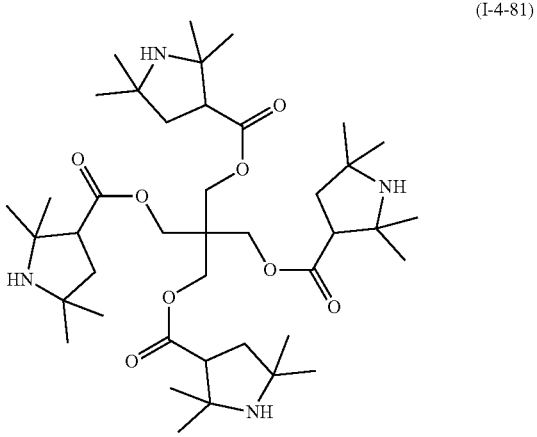
Example 25
(I-4-86)
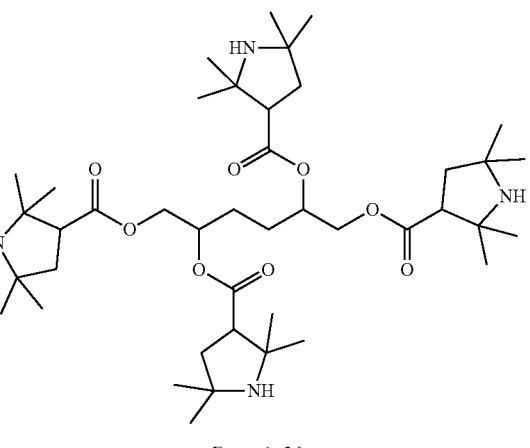
Example 26

(Example 27) Production of Compound (I-1-63)

[Chem. 51]

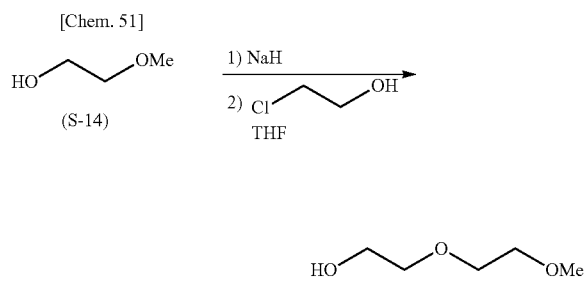

Production of Compound (5-15)

Sodium hydride (60% dispersion) (21.0 g) and THF (200 ml) were added to a reaction container equipped with a stirrer and a thermometer in a nitrogen atmosphere, and the mixture was stirred under ice cooling, and a THF (100 ml) solution of the compound (S-14) (20.0 g) was slowly added dropwise thereto. After stirring for 1 hour after the dropwise addition, 1-chloroethanol (23.3 g) was added dropwise thereto under ice cooling, the temperature was gradually raised to room temperature and stirring was carried out for 1 hour. After stopping the reaction by adding water (200 ml), the organic layer was collected, the aqueous layer was extracted with THF (100 ml) four times, the resulting THF was mixed with the organic layer obtained above and washed with 5% aqueous sodium hydroxide solution (400 ml) and subsequently with saturated saline (400 ml), dried over sodium sulfate, and concentrated under reduced pressure. The obtained residue was distilled under reduced pressure to obtain a compound (5-15) (31.2 g).

Production of Compound (I-1-63)

The compound (I-1-1) (18.5 g), dibutyltin oxide (747 mg), compound (S-15) (15.0 g), and xylene (200 ml) were added to a reaction container equipped with a stirrer, a thermometer, and a cooling tube in a nitrogen atmosphere, the mixture was stirred under heating reflux for 10 hours, and then the reaction solution was concentrated under reduced pressure. The obtained residue was dissolved in hexane (100 ml), passed through a silica gel column and an amino silica column several times, and concentrated under reduced pressure to obtain a colorless liquid compound (I-1-36) (10.6 g).

GC-MS: m/z 258.40

[M-15$^+$]

Example 28 (Compound (I-2-43)) to Example 32 (Compound (I-3-55)) were produced using the same reaction as in Example 27 and methods based on known methods as necessary.

[Chem. 52]

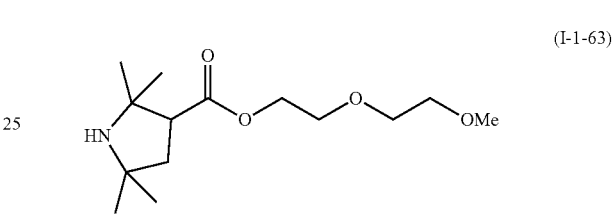

Example 27

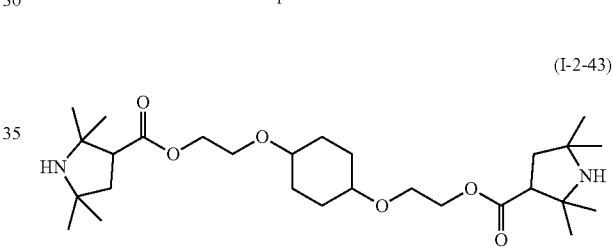

Example 28

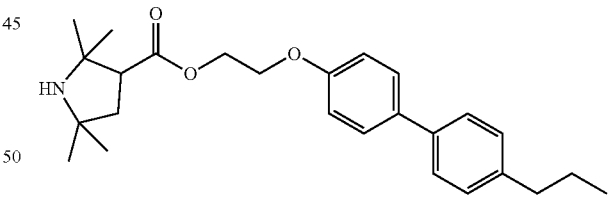

Example 29

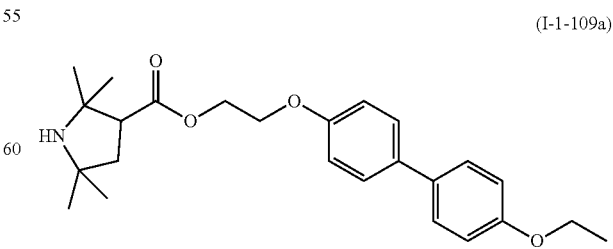

Example 30

(I-3-43)

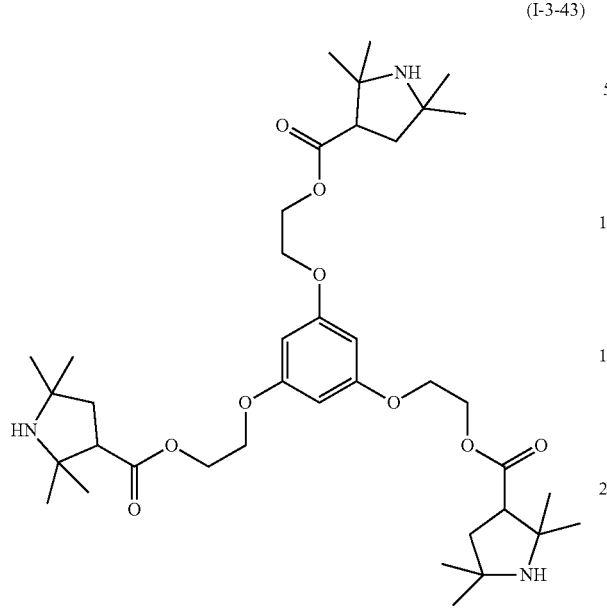

Example 31

(I-3-55)

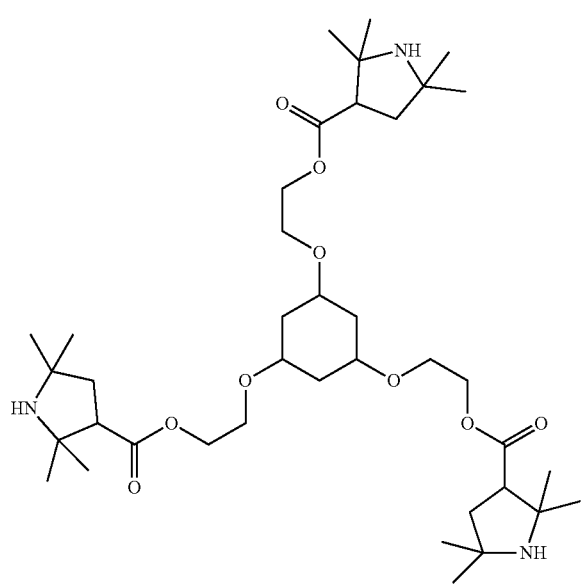

Example 32

(Example 33) Production of Compound (I-3-1)

[Chem. 53]

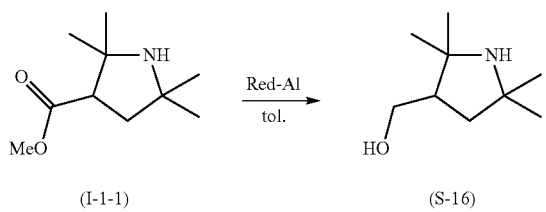

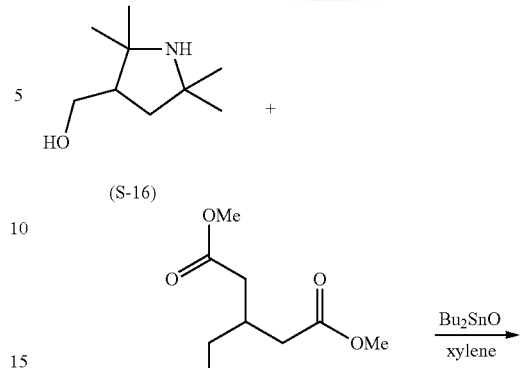

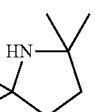

+

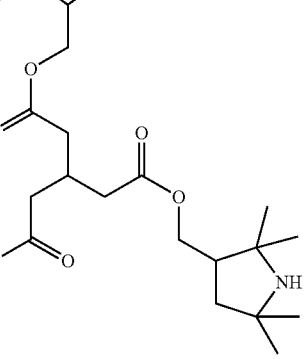

Production of Compound (5-16)

The compound (I-1-1) (10.4 g) and toluene (42 ml) were added to a reaction container equipped with a stirrer and a thermometer in a nitrogen atmosphere and stirred under ice cooling, and Red-Al (70% toluene solution) (34 g) was slowly added dropwise thereto. After the dropwise addition, the temperature was raised to room temperature, the resultant was stirred for 1 hour, then cooled again by ice-cooling, and the reaction was stopped by dropwise addition of 10% aqueous sodium hydroxide solution (100 ml). Toluene (40 ml) and THF (80 ml) were added thereto, the organic layer was collected, washed with water (100 ml) and saturated saline (100 ml) in this order, dried over sodium sulfate and concentrated under reduced pressure to obtain the compound (S-16) (4.98 g).

Production of Compound (I-3-1)

The compound (S-16) (4.98 g), dibutyltin oxide (393 mg), compound (5-17) (2.41 g), and xylene (50 ml) were added to a reaction container equipped with a stirrer, a thermometer, and a cooling tube in a nitrogen atmosphere, and the mixture was stirred under heating reflux for 10 hours, and then the reaction solution was concentrated under reduced pressure. The obtained residue was dissolved in hexane (50 ml), passed several times through a silica gel column and an amino silica column, and concentrated under reduced pressure to obtain a white solid compound (I-3-1) (1.03 g).
GC-MS: m/z 592.88
[M-15$^+$]
Example 34 (Compound (I-1-99a)) to Example 63 (Compound (I-4-56)) were produced using the same reaction as in Example 33 and methods based on known methods as necessary.
[Chem. 54]
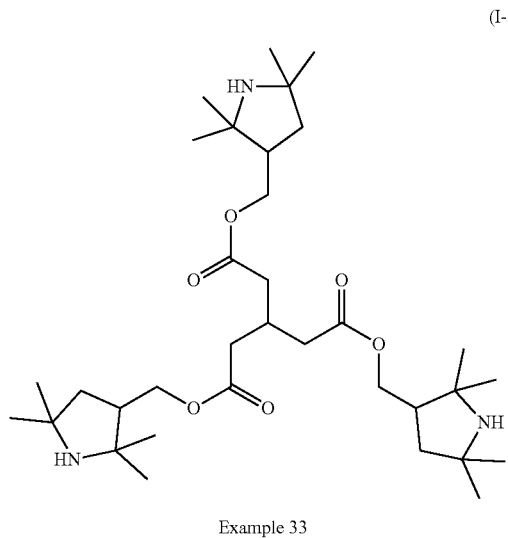
(I-3-1)
Example 33
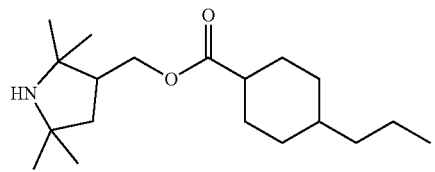
(I-1-99a)
Example 34
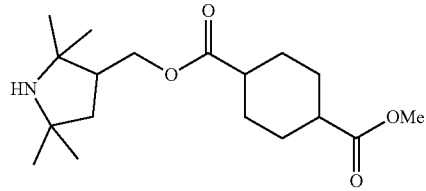
(I-1-101a)
Example 35
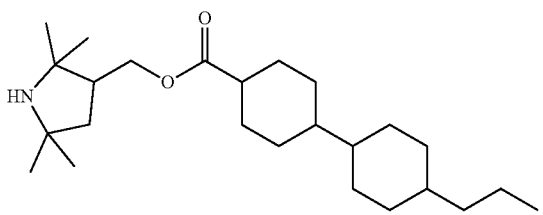
(I-1-102a)
Example 36
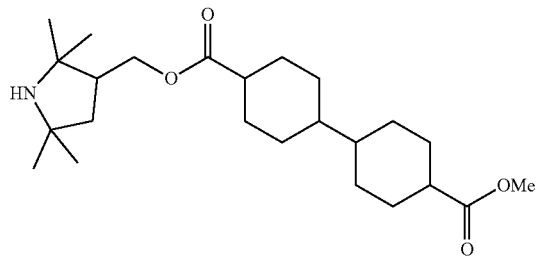
(I-1-104a)
Example 37
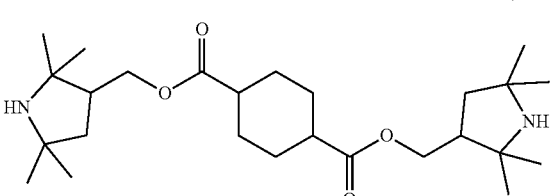
(I-2-73)
Example 38
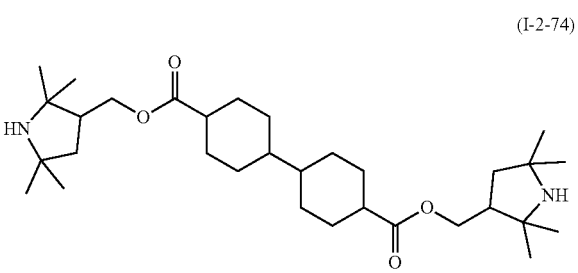
(I-2-74)
Example 39
[Chem. 55]
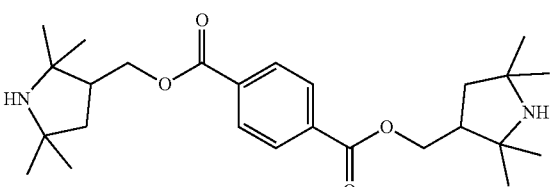
(I-2-75)
Example 40
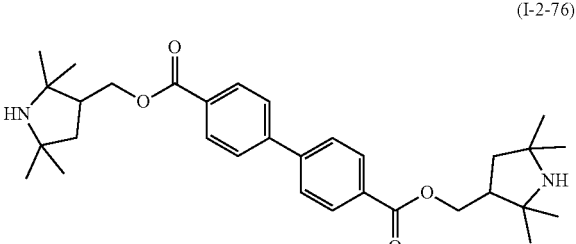
(I-2-76)
Example 41

-continued
(I-3-5)
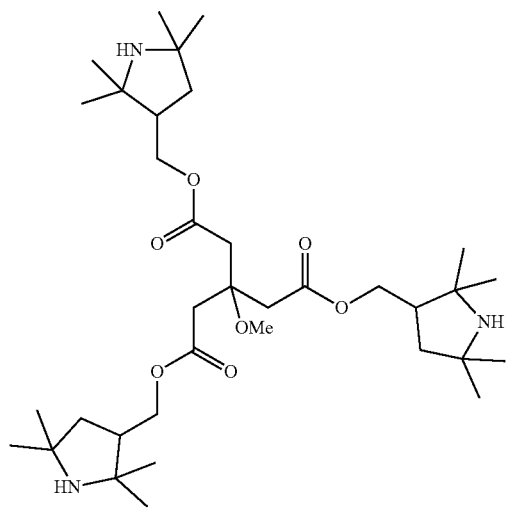
Example 42
(I-3-13)
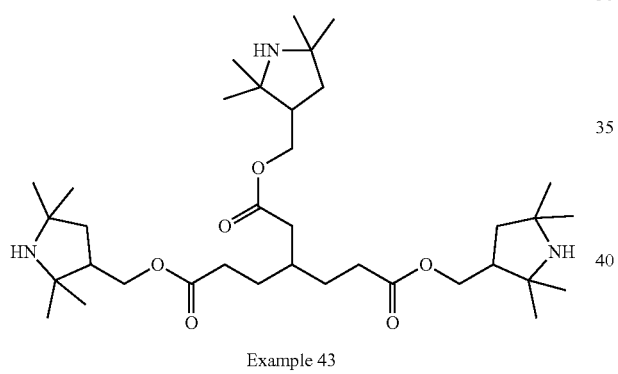
Example 43
(I-3-16)
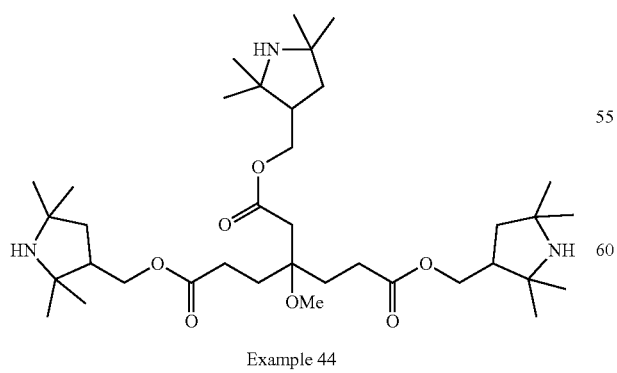
Example 44
-continued
[Chem. 56]
(I-3-25)
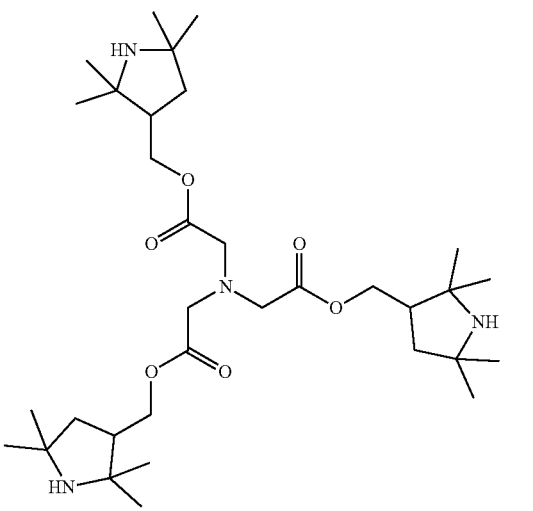
Example 45
(I-3-34)
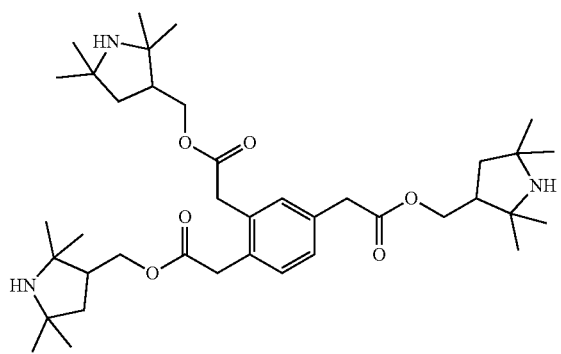
Example 46
(I-3-46)
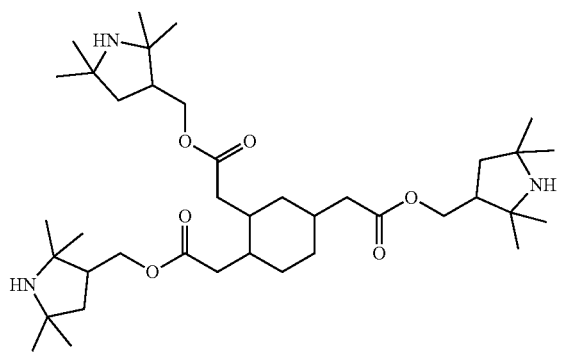
Example 47

(I-3-58)
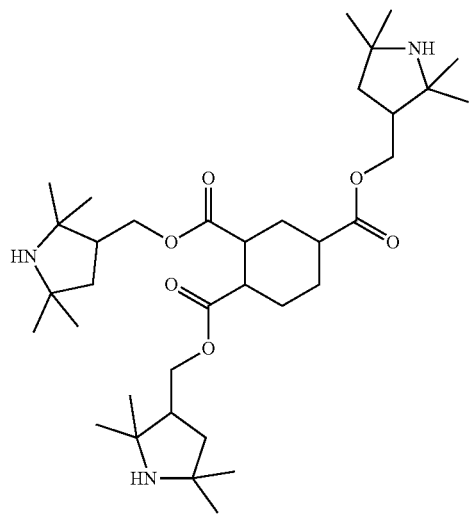
Example 48
(I-3-61)
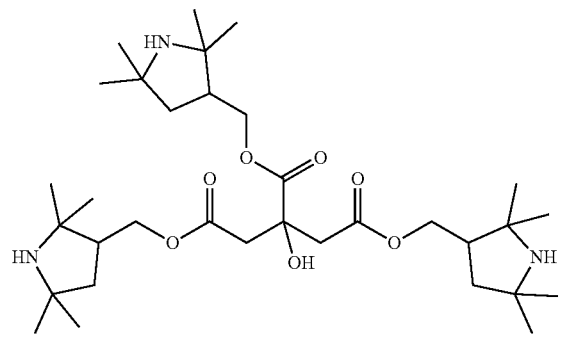
Example 49
[Chem. 57]
(I-3-64)
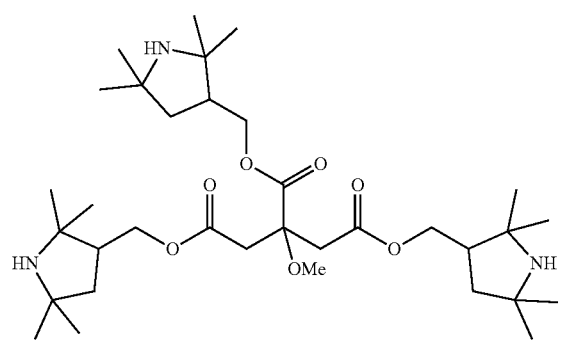
Example 50
(I-3-67)
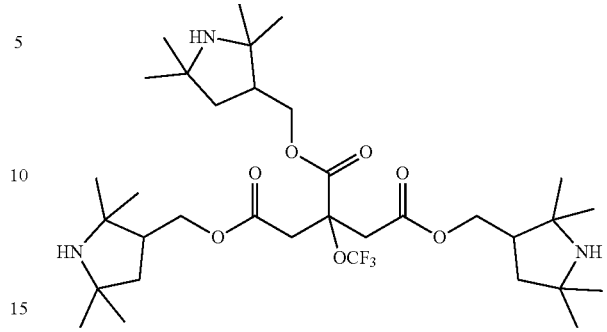
Example 51
(I-4-1)
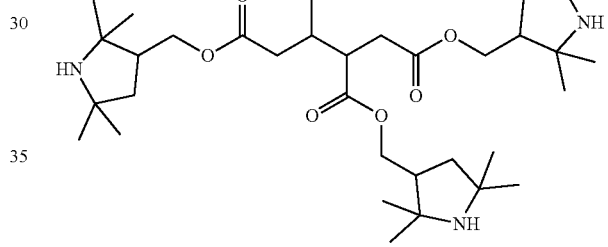
Example 52
(I-4-6)
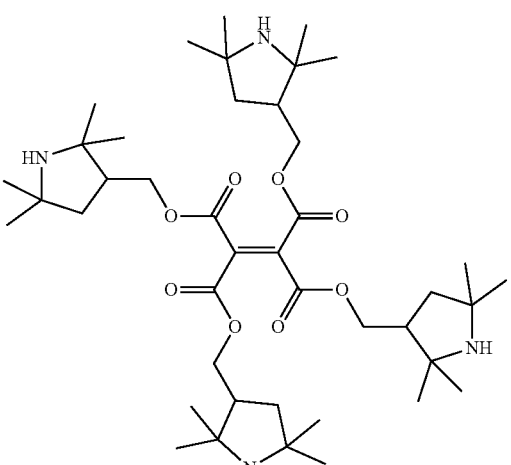
Example 53

(I-4-11)
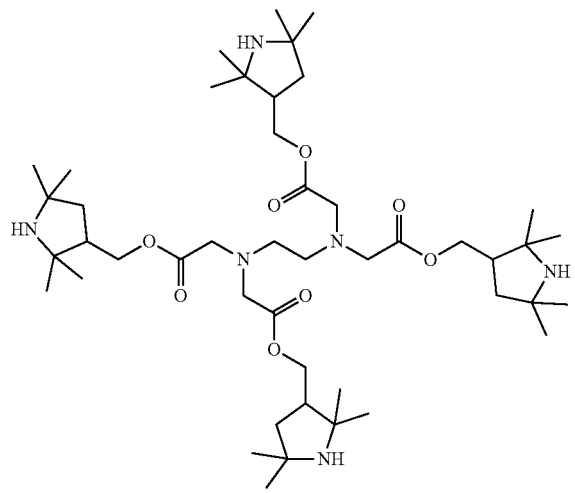
Example 54
[Chem. 58]
(I-4-16)
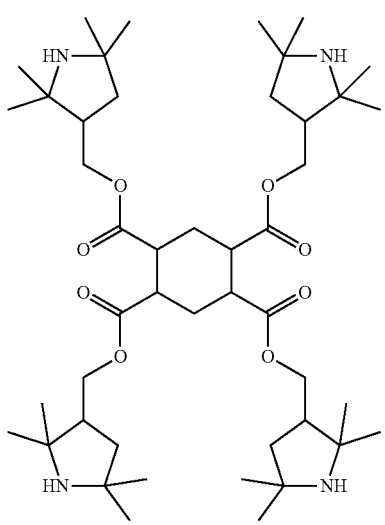
Example 55
(I-4-21)
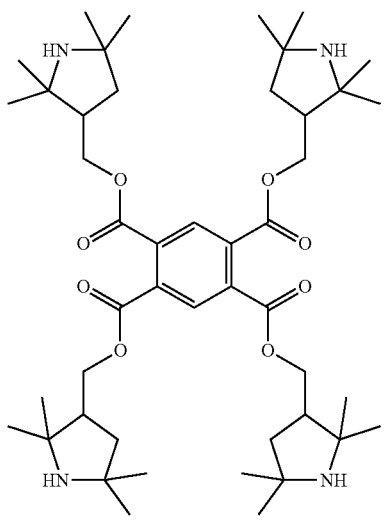
Example 56
(I-4-26)
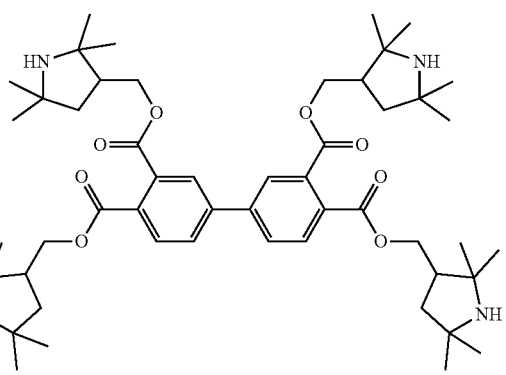
Example 57
(I-4-31)
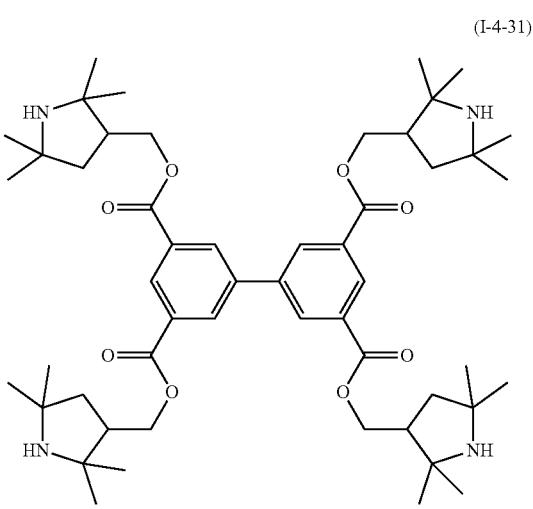
Example 58
(I-4-36)
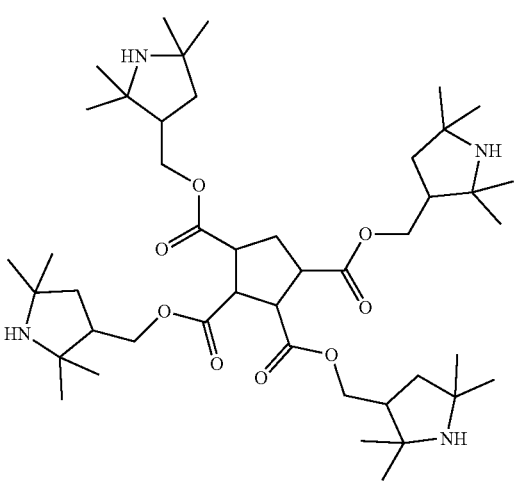
Example 59

[Chem. 59]
(I-4-41)
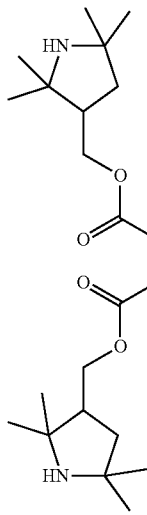
Example 60
(I-4-46)
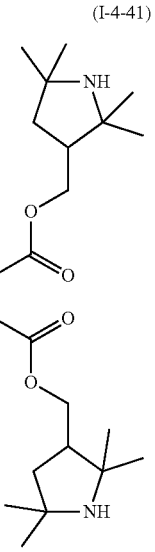
Example 61
(I-4-51)
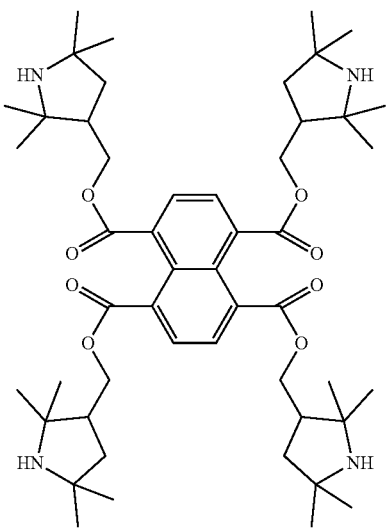
Example 62
(I-4-56)
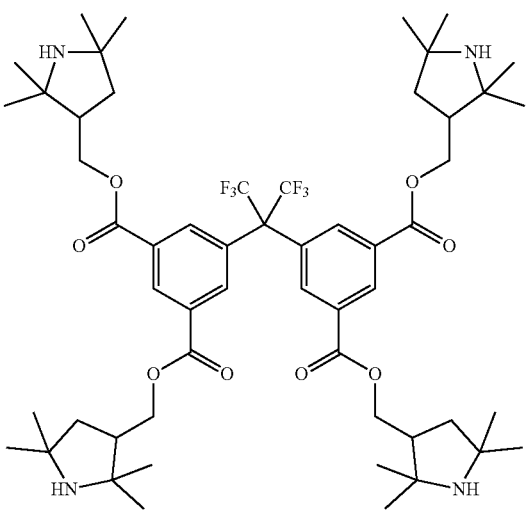
Example 63
(Example 64) Production of Compound (I-2-59)
[Chem. 60]
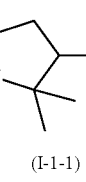
(I-1-1)
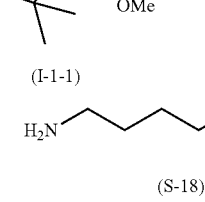
(S-18)
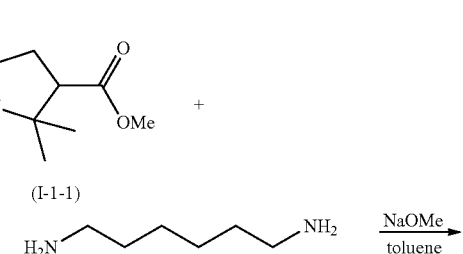

-continued

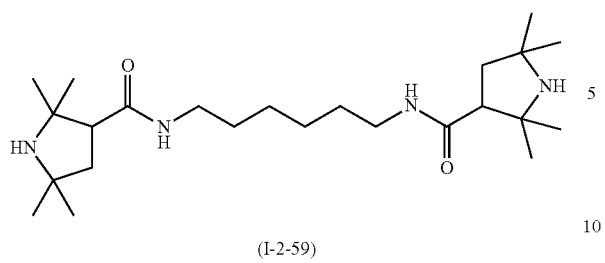

(I-2-59)

The compound (I-1-1) (10.0 g), dibutyltin oxide (146 mg), the compound (S-18) (3.14 g), and toluene (20 ml) were added to a reaction container equipped with a stirrer, a thermometer, and a cooling tube in a nitrogen atmosphere, the mixture was stirred under heating ref lux for 10 hours, and then the reaction solution was concentrated under reduced pressure. The obtained residue was dissolved in hexane (50 ml), passed through a silica gel column and an amino silica column several times, and concentrated under reduced pressure to obtain a white solid compound (I-2-59) (2.26 g).

GC-MS: m/z 407.66 [M-15$^+$]

Example 65 (Compound (I-1-33)) to Example 74 (Compound (I-3-31)) were produced using the same reaction as in Example 64 and methods based on known methods as necessary.

[Chem. 61]

(I-2-59)

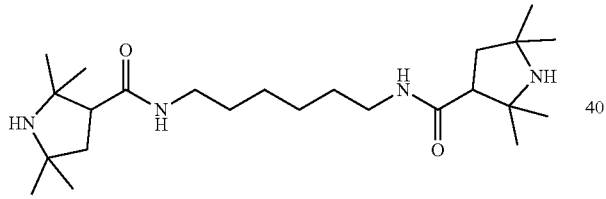

Example 64

(I-1-33)

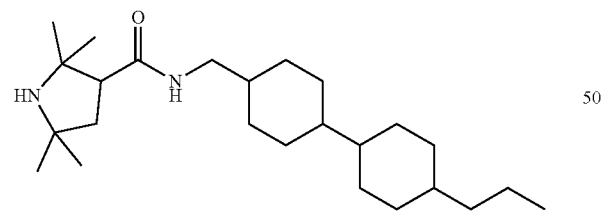

Example 65

(I-2-57)

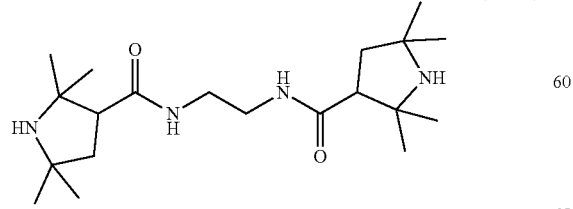

Example 66

-continued (I-2-58)

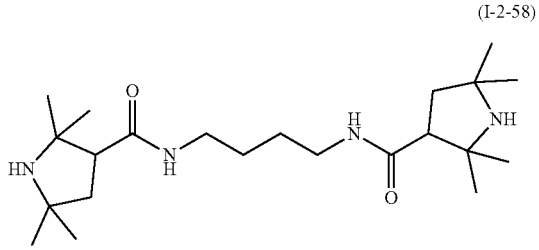

Example 67

(I-2-60)

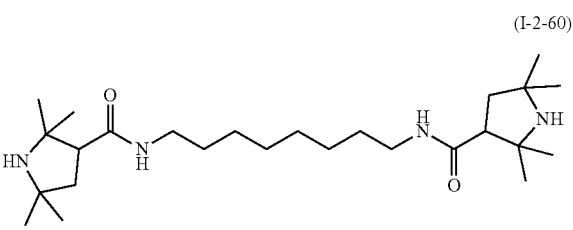

Example 68

(I-2-61)

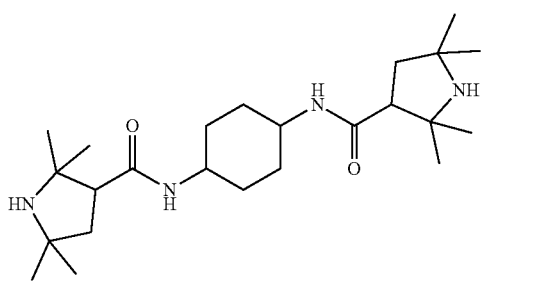

Example 69

(I-2-62)

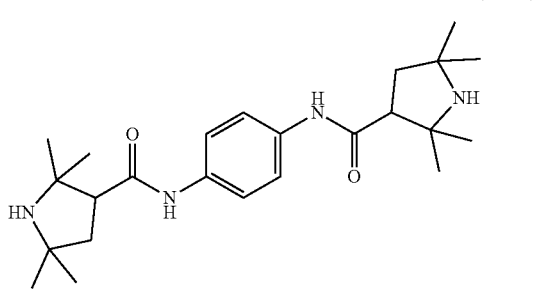

Example 70

(I-2-63)

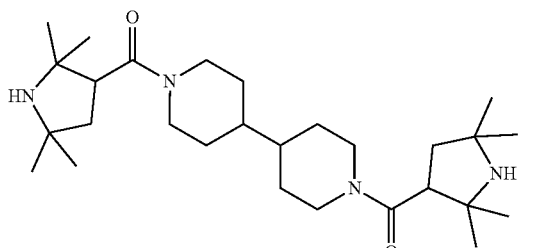

Example 71

-continued

[Chem. 62]

(I-2-64)

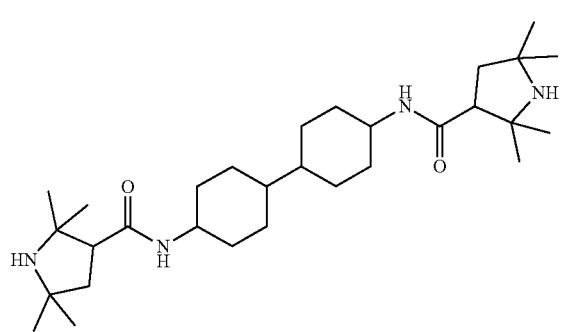

Example 72

(I-3-19)

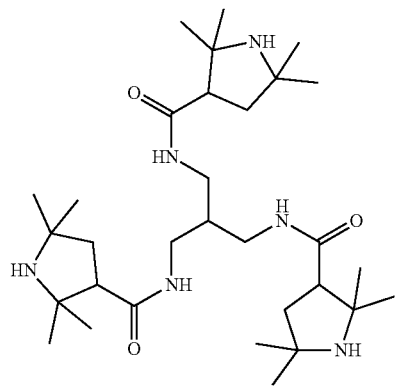

Example 73

(I-3-31)

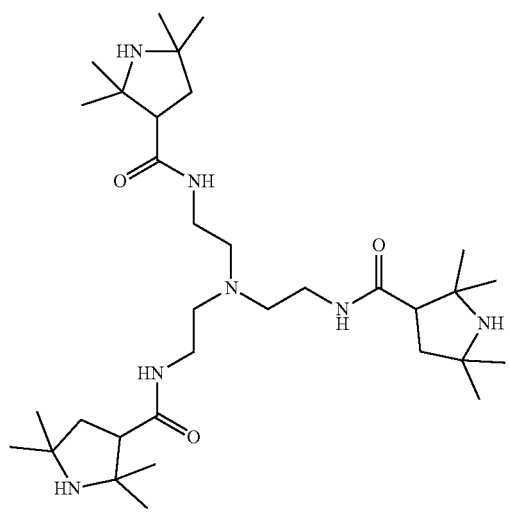

Example 74

The characteristics measured for the liquid crystal composition containing any of the compounds obtained in Examples 1 to 74 are as follows.

VHR: The voltage holding ratio (%) at 333 K was evaluated in three grades under the conditions of a frequency of 60 Hz and an applied voltage of 1 V.

A: 98 to 100%
B: 95 to 98%
C: 95% or less

Light fast VHR: The liquid crystal composition is irradiated with ultraviolet rays at 180 J/m$^2$ using an ultra-high-pressure mercury lamp through a glass having a thickness of 0.5 mm. The voltage holding ratio of the liquid crystal after ultraviolet irradiation is measured by the same method as the VHR measurement described above. However, the irradiation intensity was 0.1 W/m$^2$ at 366 nm. The evaluation was performed in three grades.

A: 90 to 100%
B: 75 to 90%
C: 75% or less

Compatibility: The state of dissolution when 500 ppm of any of the compounds obtained in Examples 1 to 74 were added to the liquid crystal composition was evaluated visually in three grades.

A: All dissolved
B: Slight amount of the compounds does not dissolve to cause separation
C: Part of the compounds does not dissolve to cause separation Storage stability: The liquid crystal composition was stored at −20° C. for 1 week, and the presence or absence of precipitates was visually evaluated in three grades.

A: No precipitates
B: Slight cloudiness is seen
C: Precipitates are able to be clearly confirmed (Example 75) Preparation of Liquid Crystal Composition-1

A host liquid crystal composition (H) having the following composition was prepared.

[Chem. 63]

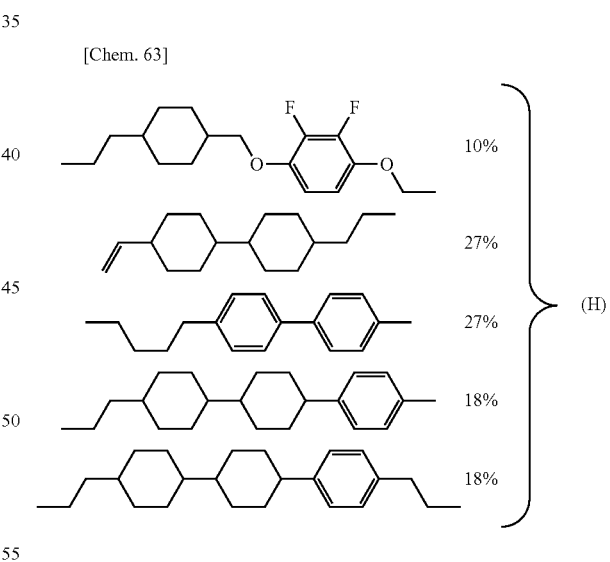

To the host liquid crystal (H), 500 ppm of the compound (I-2-7) obtained in Example 2 was added. The measured properties of the composition examples in the Examples are as follows.

VHR: A
Lightfast VHR: A
Compatibility: A
Storage stability: A

In the following, the results of measurements of Examples 76 to 147 using the compounds produced in Examples 3 to 74 in the same manner as in Example 75 are shown below.

TABLE 1

| Example | Host Liquid Crystal Composition | Additive | Additive Amount | VHR | Lightfast VHR | Compatibility | Storage Stability |
|---|---|---|---|---|---|---|---|
| 76 | H | Example 3 | 500 ppm | A | A | A | A |
| 77 | H | Example 4 | 500 ppm | A | A | A | A |
| 78 | H | Example 5 | 500 ppm | A | A | A | A |
| 79 | H | Example 6 | 500 ppm | A | A | A | A |
| 80 | H | Example 7 | 500 ppm | A | A | A | A |
| 81 | H | Example 8 | 500 ppm | A | A | A | A |
| 82 | H | Example 9 | 500 ppm | A | A | A | B |
| 83 | H | Example 10 | 500 ppm | A | A | A | A |
| 84 | H | Example 11 | 500 ppm | A | A | A | A |
| 85 | H | Example 12 | 500 ppm | A | A | A | A |
| 86 | H | Example 13 | 500 ppm | A | A | A | A |
| 87 | H | Example 14 | 500 ppm | A | A | A | A |
| 88 | H | Example 15 | 500 ppm | A | A | A | A |
| 89 | H | Example 16 | 500 ppm | A | A | A | A |
| 90 | H | Example 17 | 500 ppm | A | A | A | A |

TABLE 2

| Example | Host Liquid Crystal Composition | Additive | Additive Amount | VHR | Lightfast VHR | Compatibility | Storage Stability |
|---|---|---|---|---|---|---|---|
| 91 | H | Example 18 | 500 ppm | A | A | A | A |
| 92 | H | Example 19 | 500 ppm | A | A | A | A |
| 93 | H | Example 20 | 500 ppm | A | A | A | A |
| 94 | H | Example 21 | 500 ppm | A | A | A | A |
| 95 | H | Example 22 | 500 ppm | A | A | A | A |
| 96 | H | Example 23 | 500 ppm | A | A | B | B |
| 97 | H | Example 24 | 500 ppm | A | A | A | A |
| 98 | H | Example 25 | 500 ppm | A | A | A | A |
| 99 | H | Example 26 | 500 ppm | A | A | A | A |
| 100 | H | Example 27 | 500 ppm | A | A | A | A |
| 101 | H | Example 28 | 500 ppm | A | A | A | A |
| 102 | H | Example 29 | 500 ppm | A | A | A | A |
| 103 | H | Example 30 | 500 ppm | A | A | A | A |
| 104 | H | Example 31 | 500 ppm | A | A | A | A |
| 105 | H | Example 32 | 500 ppm | A | A | A | A |

TABLE 3

| Example | Host Liquid Crystal Composition | Additive | Additive Amount | VHR | Lightfast VHR | Compatibility | Storage Stability |
|---|---|---|---|---|---|---|---|
| 106 | H | Example 33 | 500 ppm | A | A | A | A |
| 107 | H | Example 34 | 500 ppm | A | A | A | A |
| 108 | H | Example 35 | 500 ppm | A | A | A | A |
| 109 | H | Example 36 | 500 ppm | A | A | A | A |
| 110 | H | Example 37 | 500 ppm | A | A | A | A |
| 111 | H | Example 38 | 500 ppm | A | A | A | A |
| 112 | H | Example 39 | 500 ppm | A | A | A | A |
| 113 | H | Example 40 | 500 ppm | A | A | A | A |
| 114 | H | Example 41 | 500 ppm | A | A | A | A |
| 115 | H | Example 42 | 500 ppm | A | A | A | A |
| 116 | H | Example 43 | 500 ppm | A | A | A | A |
| 117 | H | Example 44 | 500 ppm | A | A | A | A |
| 118 | H | Example 45 | 500 ppm | A | A | A | A |
| 119 | H | Example 46 | 500 ppm | A | A | A | A |
| 120 | H | Example 47 | 500 ppm | A | A | A | A |

TABLE 4

| Example | Host Liquid Crystal Composition | Additive | Additive Amount | VHR | Lightfast VHR | Compatibility | Storage Stability |
|---|---|---|---|---|---|---|---|
| 121 | H | Example 48 | 500 ppm | A | A | A | A |
| 122 | H | Example 49 | 500 ppm | A | A | A | A |
| 123 | H | Example 50 | 500 ppm | A | A | A | A |
| 124 | H | Example 51 | 500 ppm | A | A | A | A |
| 125 | H | Example 52 | 500 ppm | A | A | A | A |
| 126 | H | Example 53 | 500 ppm | A | A | B | B |
| 127 | H | Example 54 | 500 ppm | A | A | A | A |
| 128 | H | Example 55 | 500 ppm | A | A | A | A |
| 129 | H | Example 56 | 500 ppm | A | A | A | A |
| 130 | H | Example 57 | 500 ppm | A | A | B | B |
| 131 | H | Example 58 | 500 ppm | A | A | B | B |
| 132 | H | Example 59 | 500 ppm | A | A | A | A |
| 133 | H | Example 60 | 500 ppm | A | A | B | B |
| 134 | H | Example 61 | 500 ppm | A | A | B | B |
| 135 | H | Example 62 | 500 ppm | A | A | B | B |

TABLE 5

| Example | Host Liquid Crystal Composition | Additive | Additive Amount | VHR | Lightfast VHR | Compatibility | Storage Stability |
|---|---|---|---|---|---|---|---|
| 136 | H | Example 63 | 500 ppm | A | A | B | B |
| 137 | H | Example 64 | 500 ppm | A | A | A | B |
| 138 | H | Example 65 | 500 ppm | A | A | A | A |
| 139 | H | Example 66 | 500 ppm | A | A | B | B |
| 140 | H | Example 67 | 500 ppm | A | A | A | B |
| 141 | H | Example 68 | 500 ppm | A | A | A | B |
| 142 | H | Example 69 | 500 ppm | A | A | B | B |
| 143 | H | Example 70 | 500 ppm | A | A | B | B |
| 144 | H | Example 71 | 500 ppm | A | A | A | B |
| 145 | H | Example 72 | 500 ppm | A | A | B | B |
| 146 | H | Example 73 | 500 ppm | A | A | B | B |
| 147 | H | Example 74 | 500 ppm | A | A | B | B |

Comparative Example 1

As a comparative example, the characteristics of the host liquid crystal (H) were measured without addition of further compounds as follows.

VHR: A

Lightfast VHR: C

Storage stability: A

From these results, it is understood that the compound of the present invention has an effect of preventing the liquid crystal composition from being deteriorated due to light without impairing the storage stability of the liquid crystal composition.

Comparative Example 2

500 ppm of the compound (R-1) was added to the host liquid crystal (H), and the measured results were as follows.

[Chem. 64]

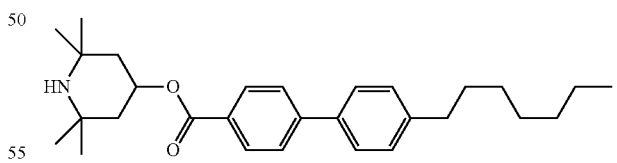

(R-1)

Lightfast VHR: A

Compatibility: B

Storage stability: C

Comparative Examples 3 and 4

In the following, in the same manner as in Comparative Example 2, the results of measurement of Comparative Examples 3 and 4 are shown below.

[Chem. 65]

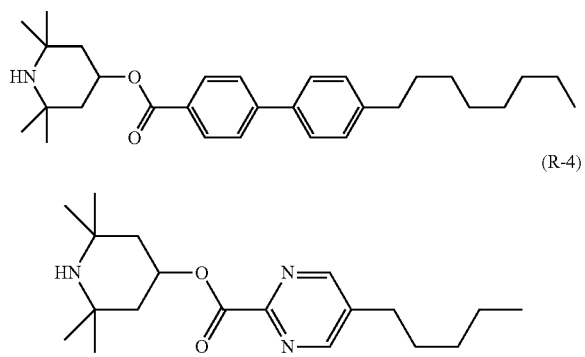

(R-3)

(R-4)

[Chem. 67]

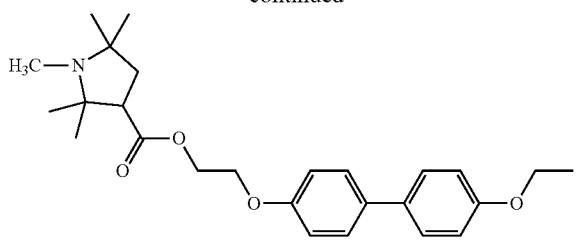

Example 149

TABLE 6

| Comparative Example | Host Liquid Crystal Composition | Additive | Additive Amount | VHR | Lightfast VHR | Compatibility | Storage Stability |
|---|---|---|---|---|---|---|---|
| 3 | H | (R-3) | 500 ppm | A | A | B | C |
| 4 | H | (R-4) | 500 ppm | A | B | B | B |

From these results, it is understood that the compound of the present invention has high compatibility with the liquid crystal composition without impairing the storage stability of the liquid crystal composition, and has an effect of preventing the liquid crystal composition from being deteriorated due to light.

The compounds of Examples 148 to 170 were produced using the same reactions as in Examples 1 to 74 and methods based on known methods as necessary.

-continued

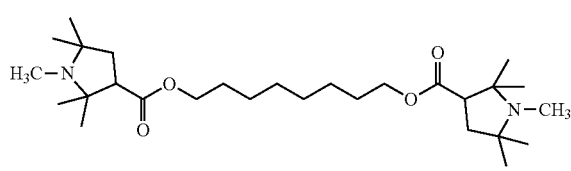

Example 150

[Chem. 66]

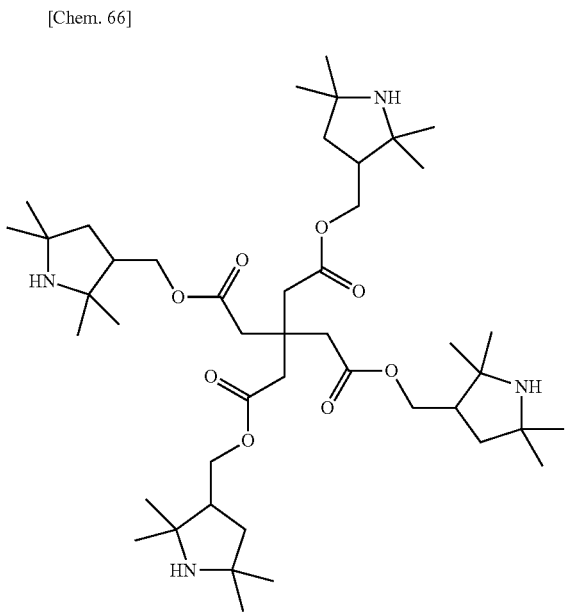

Example 148

(I-2-15)

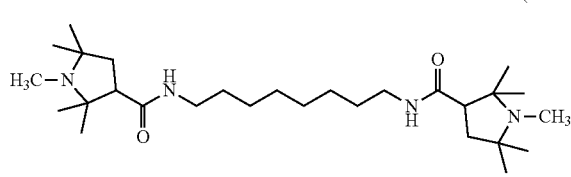

Example 151

(I-2-68)

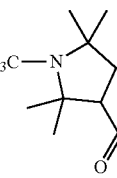

Example 152

(I-2-46)
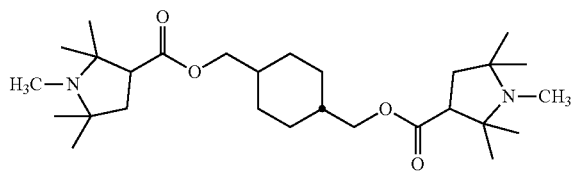
Example 153
(I-2-52)
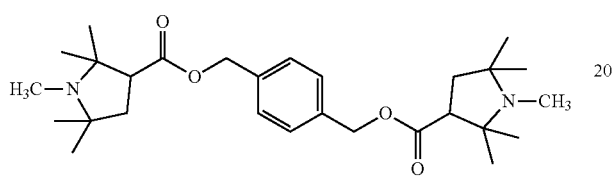
Example 154
(I-2-78)
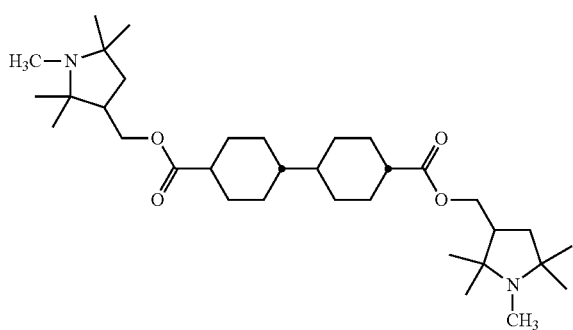
Example 155
(I-2-48)
Example 156
(I-3-2)
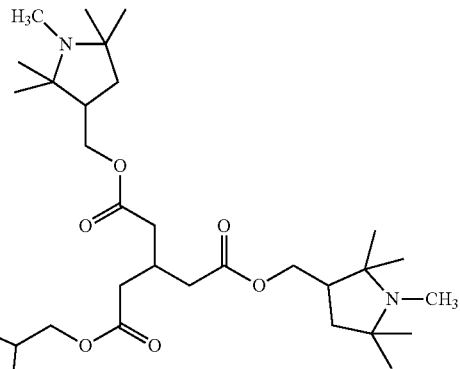
Example 157
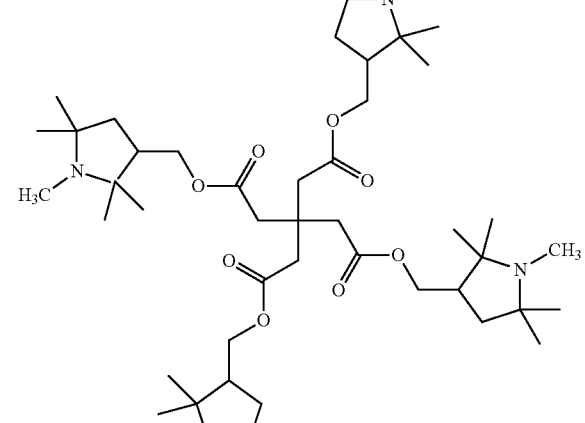
Example 158
[Chem. 68]
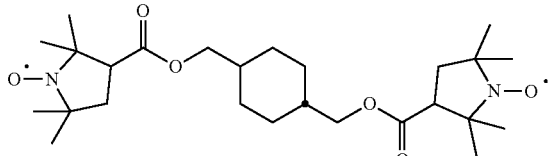
Example 159
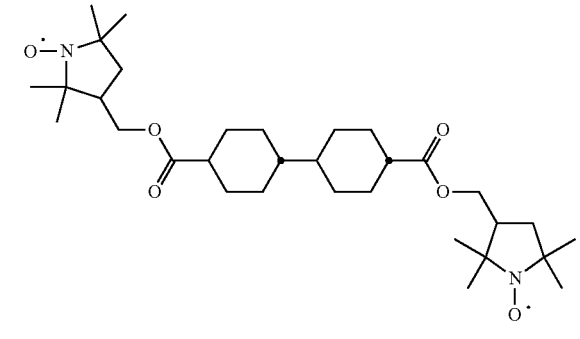
Example 160

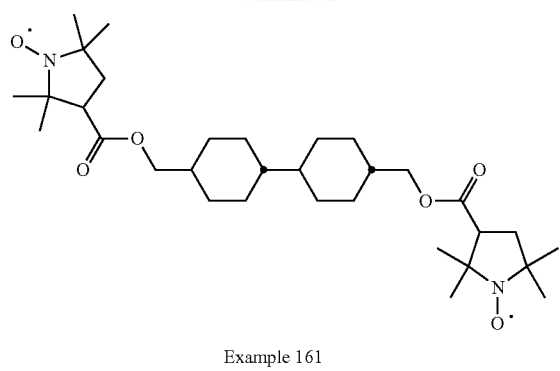

Example 161

[Chem. 69]

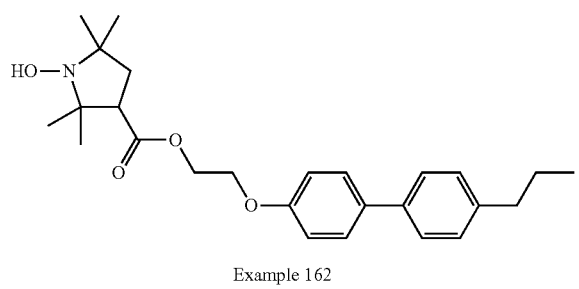

Example 162

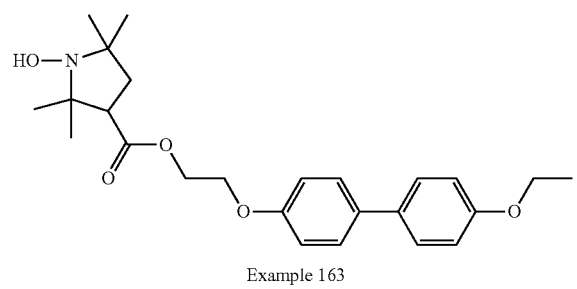

Example 163

(I-2-29)

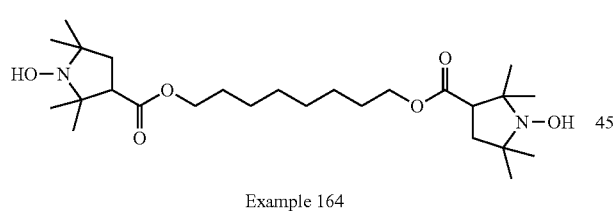

Example 164

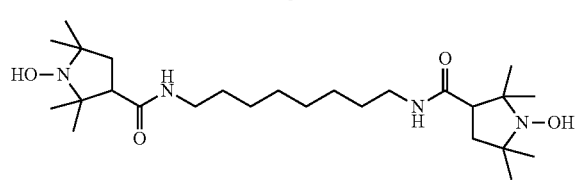 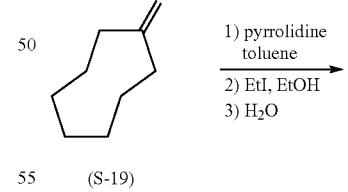

Example 165

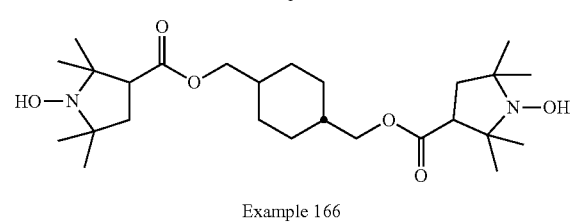

Example 166

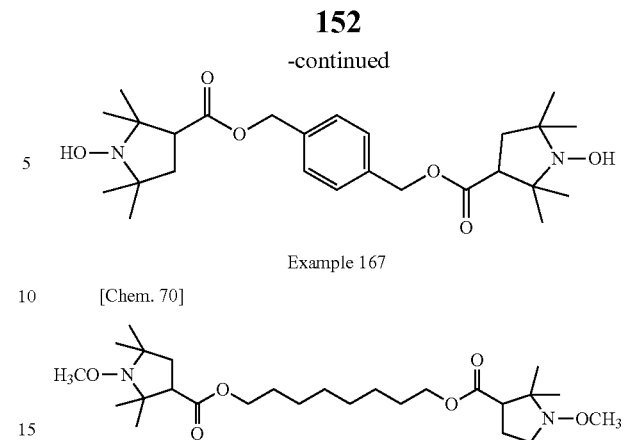

Example 167

[Chem. 70]

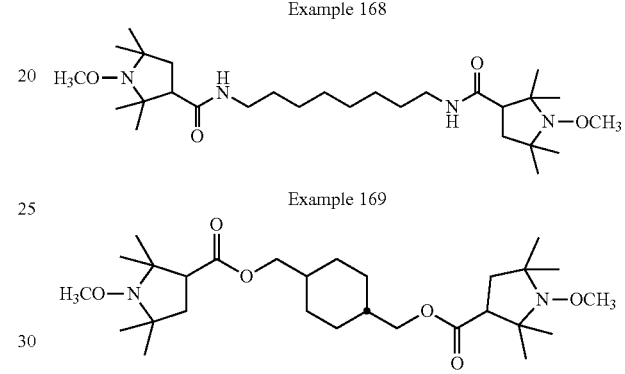

Example 168

Example 169

Example 170

As results of performing the same measurement as in Example 75 with respect to the compounds produced in Examples 148 to 170, it was confirmed that the compounds exhibited high VHR and lightfast VHR, and the compatibility and storage stability were also excellent similarly to Examples 75 to 147.

(Example 171) Production of Compound (I-2-107)

[Chem. 71]

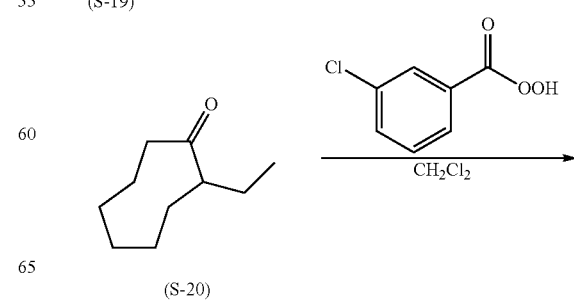

-continued

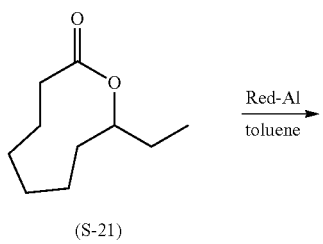
(S-21)

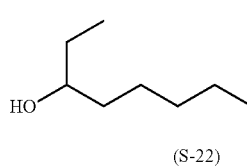
(S-22)

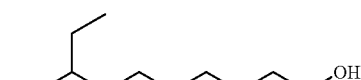

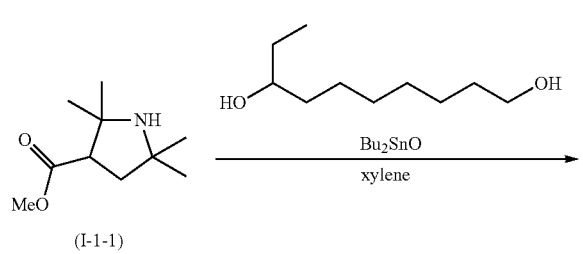
(I-1-1)

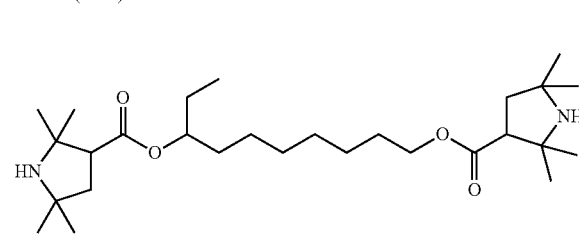
(I-2-107)

[Chem. 72]

(I-2-107)

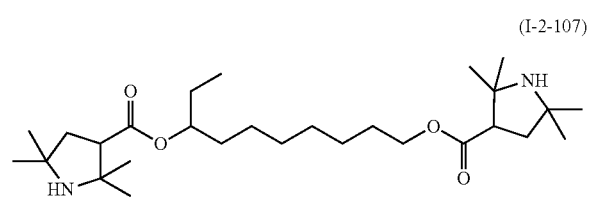
Example 171

(I-2-102)

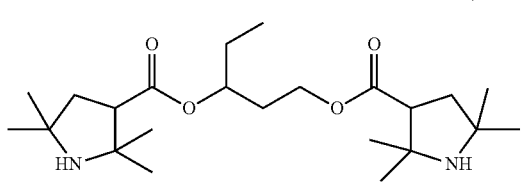
Example 172

-continued (I-2-103)

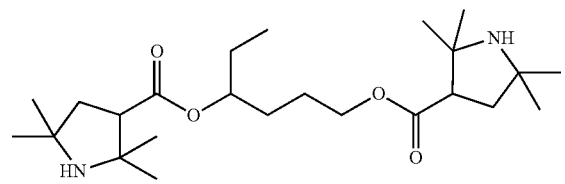
Example 173

(I-2-104)

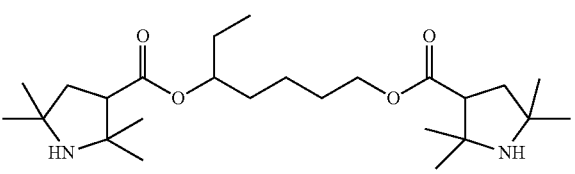
Example 174

(I-2-105)

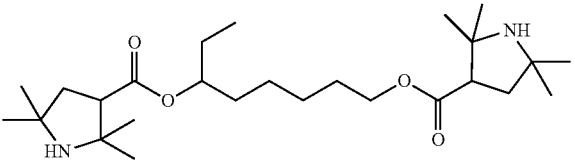
Example 175

(I-2-106)

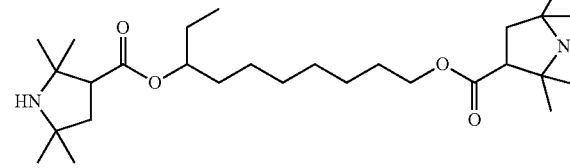
Example 176

Production of Compound (S-20)

The compound (S-19) (23.0 g), pyrrolidine (25.9 g), and toluene (150 ml) were added to a reaction container equipped with a stirrer and a thermometer in a nitrogen atmosphere, and the mixture was stirred under heating reflux for 6 hours, and then concentrated under reduced pressure to remove toluene, water, and pyrrolidine. Subsequently, ethyl iodide (31.2 g) and ethanol (20 ml) were slowly added in a nitrogen atmosphere, the mixture was stirred under heating reflux for 5 hours, and then concentrated under reduced pressure to remove ethanol. Water (40 ml) was added to the obtained crystals, the mixture was stirred under heating reflux for 3 hours, then the organic layer was collected and the aqueous layer was extracted with toluene (100 ml), the resulting toluene was mixed with the organic layer obtained above, washed with saturated saline (200 ml), dried over sodium sulfate, and concentrated under reduced pressure. The obtained residue was distilled under reduced pressure to obtain a compound (S-20) (24.5 g).

Production of Compound (5-21)

The compound (S-20) (24.5 g) and dichloromethane (200 ml) were added to a reaction container equipped with a stirrer and a thermometer in a nitrogen atmosphere, and while stirring under ice cooling, m-chloroperbenzoic acid (38.4 g) was added slowly thereto, heated to room temperature, and then stirred for 15 hours. The precipitated white solid was filtered while being washed with dichloromethane, and the filtrate was washed with 10% aqueous sodium hydrogen sulfite solution (100 ml), 10% aqueous sodium sulfite solution (100 ml), 10% sodium hydrogen carbonate aqueous solution (100 ml), water (100 ml), and saturated saline (100 ml) in order, dried over sodium sulfate, and concentrated under reduced pressure. The obtained residue was distilled under reduced pressure to obtain a compound (S-21) (26.5 g).

Production of Compound (S-22)

This compound (26.5 g) and toluene (120 ml) were added to a reaction container equipped with a stirrer and a thermometer in a nitrogen atmosphere, the mixture was stirred under ice cooling, and Red-Al (70% toluene solution) (84.9 g) was slowly added dropwise thereto. After the dropwise addition, the temperature was raised to room temperature, the resultant was stirred for 1 hour, then cooled again by ice-cooling, and the reaction was stopped by dropwise addition of 10% aqueous sodium hydroxide solution (300 ml). Toluene (160 ml) and THF (160 ml) were added thereto, the organic layer was collected, washed with saturated saline (100 ml), dried over sodium sulfate, and concentrated under reduced pressure to obtain Compound (S-22) (18.2 g).

Production of Compound (I-2-107)

The compound (I-1-1) (18.5 g), dibutyltin oxide (747 mg), the compound (S-22) (8.7 g), and xylene (200 ml) were added to a reaction container equipped with a stirrer, a thermometer, and a cooling tube in a nitrogen atmosphere, the mixture was stirred under heating reflux for 10 hours, and the reaction solution was concentrated under reduced pressure. The obtained residue was dissolved in hexane (100 ml), passed several times through a silica gel column and an amino silica column, and concentrated under reduced pressure to obtain a colorless liquid compound (I-2-107) (27.6 g).

GC-MS: m/z 465.39 [M-15$^+$]

Example 172 (Compound (I-2-103)) to Example 176 (Compound (I-2-106)) were produced using the same reaction as in Example 171 and methods based on known methods as necessary.

The invention claimed is:

1. A compound represented by General Formula (I):

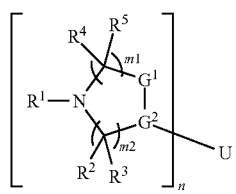

wherein R$^1$ represents a hydrogen atom, a hydroxyl group, or an alkyl group having 1 to 20 carbon atoms; one —CH$_2$-or two or more non-adjacent (—CH$_2$—)'s present in the alkyl group, except for —CH$_2$— directly bonded to a nitrogen atom adjacent to R$^1$, may each independently be substituted with —O—, —S—, —CO—, —CO—O—, —O—CO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —C≡C—, —Si(CH$_3$)$_2$—, a trans 1,4-cyclohexylene group, a 1,4-phenylene group, or a naphthalene-2,6-diyl group; and one or two or more of hydrogen atoms in R$^1$ may each independently be substituted with a fluorine atom, a chlorine atom, or a cyano group, R$^2$, R$^3$, R$^4$, and R$^5$ each independently represent an alkyl group having 1 to 8 carbon atoms, -G$^1$-G$^2$- is a group represented by:

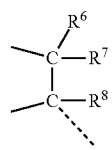

(wherein the broken line represents a bond to U in General Formula (I), and R$^6$, R$^7$, and R$^8$ each independently represent a hydrogen atom), U represents a group represented by General Formula (U-1):

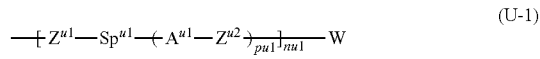

(U-1)

(wherein Z$^{u1}$ represents —CH$_2$O—, —COO— or —CH$_2$—OCO—, Z$^{u2}$ represents —O—, —S—, —CH$_2$O—, —CH$_2$CH$_2$—, —CO—, —COO—, —CO—S—, —O—CO—O—, —CO—NH—, —NH—CO—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, A$^{u1}$ represents a group selected from the group consisting of:

(a) a 1,4-cyclohexylene group (one —CH$_2$— or two or more non-adjacent (—CH$_2$—)'s present in this group may be substituted with —O—);

(b) a 1,4-phenylene group (one —CH= or two or more non-adjacent (—CH=)'s present in this group may be substituted with —N=);

(c) a naphthalene-2,6-diyl group, a 1,2,3,4-tetrahydronaphthalene-2,6-diyl group, or a decahydronaphthalene-2,6-diyl group (one —CH= or two or more non-adjacent —CH= present in the naphthalene-2,6-diyl group or the 1,2,3,4-tetrahydronaphthalene-2,6-diyl group may be substituted with —N=); and the group (a), the group (b), and the group (c) may each independently be substituted with a fluorine atom, a chlorine atom, a bromine atom, an iodine atom, a pentafluorosulfuranyl group, a nitro group, a cyano group, an isocyano group, an amino group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, and one —CH$_2$— or two or more non-adjacent (—CH$_2$—)'s present in the alkyl group may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, Sp$^{u1}$ represents a single bond or an alkylene group having 1 to 10 carbon atoms; and one —CH$_2$— or two or more non-adjacent (—CH$_2$—)'s present in the alkylene group, except for —CH$_2$— directly bonded to Z$^{u1}$ adjacent to Sp$^{u1}$, may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, W represents a monovalent to decavalent organic group; provided that the valency of W is the same as a number represented by n in General Formula (I), pu1 represents an integer from 0 to 8, and nu1 represents an integer of 1 to 4, provided that when nu1 represents 1 or 2 and pu1 is 0, Sp$^{u1}$ represents an alkylene group having 2 to 10 carbon atoms in which one or two or more non-adjacent (—CH$_2$—)'s present in the alkylene group, except for —CH$_2$— directly bonded to Z$^{u1}$ adjacent to Sp$^{u1}$, each independently are substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, and if any, plural Z$^{u1}$'s may be the same or different; plural Z$^{u2}$'s may be the same or different; plural Sp$^{u1}$'s may be the same or different; and plural A$^{u1}$'s may be the same or different), m1 and m2 each independently represent an integer of 1, and n represents an integer of 1 to 4, provided that when n=1;

W is a hydrogen atom, a fluorine atom, a chlorine atom, a bromine atom, an iodine atom, a pentafluorosulfuranyl group, a nitro group, an amino group, a hydroxyl group, a mercapto group, or an alkyl group having 1 to 12 carbon atoms, and one —CH$_2$— or two or more non-adjacent (—CH$_2$—)'s present in the alkyl group may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, provided that when W represents a hydrogen atom or an alkyl group, pu1 is an integer of 1 or more, when n=2;

W represents an alkylene group having 1 to 10 carbon atoms, and one —CH$_2$— or two or more non-adjacent (—CH$_2$—)'s present in the alkylene group may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, or W represents a group selected from the group consisting of:

(a) a 1,4-cyclohexylene group (one —CH$_2$— or two or more non-adjacent (—CH$_2$—)'s present in this group may be substituted with —O—), (b) a 1,4-phenylene group (one —CH= or two or more non-adjacent —CH= present in this group may be substituted with —N=), (c) a naphthalene-2,6-diyl group, a 1,2,3,4-tetrahydronaphthalene-2,6-diyl group, or a decahydronaphthalene-2,6-diyl group (one —CH= or two or more non-adjacent —CH= present in the naphthalene-2,6-diyl group or the 1,2,3,4-tetrahydronaphthalene-2,6-diyl group may be substituted with —N=), and the group (a), the group (b), and the group (c) may each independently be substituted with a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, and one —CH$_2$— or two or more non-adjacent (—CH$_2$—)'s present in the alkyl group may each independently be substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, when n=3;

W is a group selected from the group consisting of (W3-1) to (W3-12):

(W3-1)

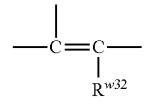

(W3-2)

(W3-3)

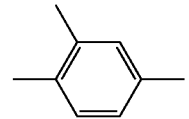

(W3-4)

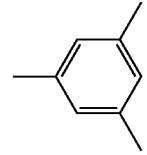

(W3-5)

-continued (W3-6)
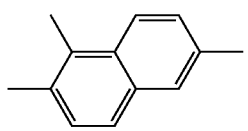

(W3-7)
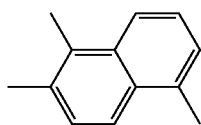

(W3-8)
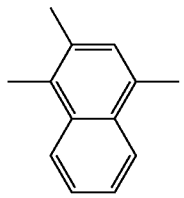

(W3-9)
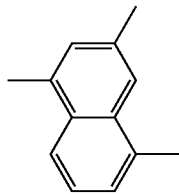

(W3-10)
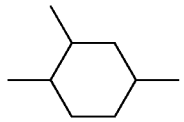

(W3-11)

(W3-12)

wherein $R^{w31}$ and $R^{w32}$ represent a hydrogen atom, a hydroxyl group, or an alkyl group having 1 to 10 carbon atoms, and one or two or more (—$CH_2$—)'s present in the alkyl group may each independently be substituted with —O—, —S—, —CH=CH—, —C≡C—, —CO—O—, or —O—CO—, and any arbitrary hydrogen atom in a cyclic structure may be substituted with a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms in which one —$CH_2$— or two or more non-adjacent (—$CH_2$—)'s present in the alkyl group may each independently be substituted with —O—, —S—, —CO—, —COO—, —OCO—, —CO—S—, —S—CO—, —O—CO—O—, —CO—NH—, —NH—

CO—, —CH=CH—COO—, —CH=CH—OCO—, —COO—CH=CH—, —OCO—CH=CH—, —CH=CH—, —CF=CF—, —OCF$_2$—CF$_2$O—, or —C≡C—, and when n=4;

W is a group selected from the group consisting of (W4-1) to (W4-21):

(W4-1)

(W4-2)
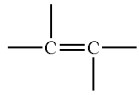

(W4-3)
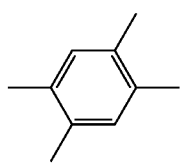

(W4-4)
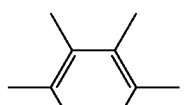

(W4-5)
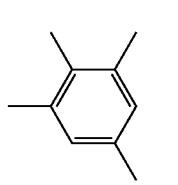

(W4-6)
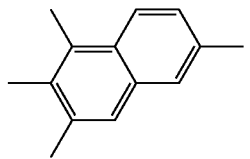

(W4-7)
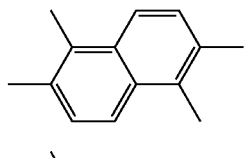

(W4-8)
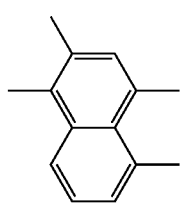

(W4-9)
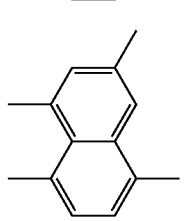

(W4-10) 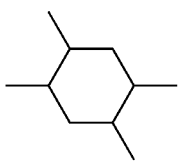

(W4-11) 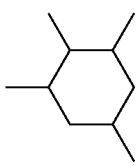

(W4-12) 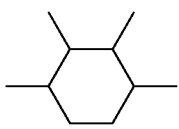

(W4-13) 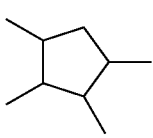

(W4-14) 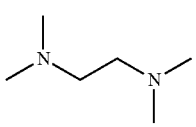

(W4-15) 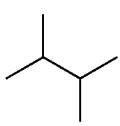

(W4-16) 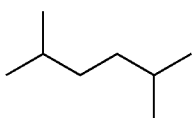

(W4-17) 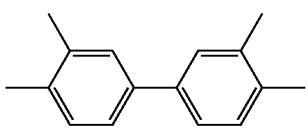

(W4-18) 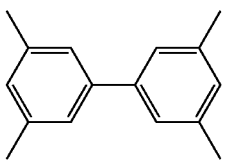

(W4-19) 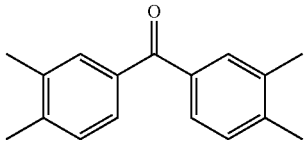

(W4-20) 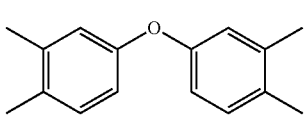

(W4-21) 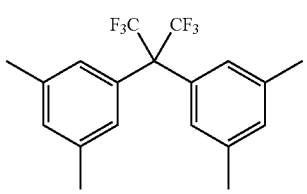

provided that, if any, plural $R^1$'s are the same or different, plural -$G^1$-$G^2$-'s are the same or different, plural $Z^{u1}$'s are the same or different, plural $Z^{u2}$'s are the same or different, plural $Sp^{u1}$'s are the same or different, plural $A^{u1}$'s are the same or different, and plural nu1's are the same or different.

2. The compound according to claim 1, wherein pu1 in General Formula (I) represents an integer of 1 to 8.

3. The compound according to claim 1, wherein nu1 in General Formula (I) represents 1.

4. The compound according to claim 1, wherein nu1 in General Formula (I) represents an integer of 2.

5. The compound according to claim 1, wherein nu1 in General Formula (I) represents an integer of 3 or 4.

6. A composition comprising:
one or two or more of compounds according to claim 1; and
a host compound.

* * * * *